US011107994B2

(12) United States Patent
Joosten et al.

(10) Patent No.: US 11,107,994 B2
(45) Date of Patent: *Aug. 31, 2021

(54) MATERIALS FOR ORGANIC ELECTROLUMINESCENT DEVICES

(71) Applicant: Merck Patent GmbH, Darmstadt (DE)

(72) Inventors: Dominik Joosten, Frankfurt am Main (DE); Anna Hayer, Mainz (DE); Florian Maier-Flaig, Weinheim (DE); Rouven Linge, Darmstadt (DE); Holger Heil, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 776 days.

This patent is subject to a terminal disclaimer.

(21) Appl. No.: 15/319,506

(22) PCT Filed: May 22, 2015

(86) PCT No.: PCT/EP2015/001059
§ 371 (c)(1),
(2) Date: Dec. 16, 2016

(87) PCT Pub. No.: WO2015/192939
PCT Pub. Date: Dec. 23, 2015

(65) Prior Publication Data
US 2017/0324044 A1    Nov. 9, 2017

(30) Foreign Application Priority Data
Jun. 18, 2014 (EP) .................................... 14002104

(51) Int. Cl.
| | | |
|---|---|---|
| *H01L 51/00* | (2006.01) |
| *C07D 209/96* | (2006.01) |
| *C07D 405/14* | (2006.01) |
| *C07D 403/04* | (2006.01) |
| *C07D 403/10* | (2006.01) |
| *C07D 403/14* | (2006.01) |
| *C07D 209/80* | (2006.01) |
| *H01L 51/50* | (2006.01) |

(52) U.S. Cl.
CPC ........ *H01L 51/0072* (2013.01); *C07D 209/80* (2013.01); *C07D 209/96* (2013.01); *C07D 403/04* (2013.01); *C07D 403/10* (2013.01); *C07D 403/14* (2013.01); *C07D 405/14* (2013.01); *H01L 51/006* (2013.01); *H01L 51/0061* (2013.01); *H01L 51/5016* (2013.01); *H01L 51/5012* (2013.01)

(58) Field of Classification Search
CPC .. C07D 209/96; C07D 487/10; C07D 491/20; C09K 11/06; H01L 51/0071; H01L 51/0072
See application file for complete search history.

(56) References Cited

U.S. PATENT DOCUMENTS

| | | | |
|---|---|---|---|
| 9,417,269 B2 | 8/2016 | Sakai et al. | |
| 9,444,064 B2 | 9/2016 | Kaiser et al. | |
| 9,559,309 B2 | 1/2017 | Min et al. | |
| 10,121,973 B2 | 11/2018 | Hong et al. | |
| 10,227,528 B2 * | 3/2019 | Jatsch | C07D 487/10 |
| 2012/0097899 A1 | 4/2012 | Parham et al. | |
| 2013/0032787 A1 | 2/2013 | Kim et al. | |
| 2013/0256645 A1 * | 10/2013 | Min | C09K 11/06 257/40 |
| 2014/0332787 A1 | 11/2014 | Hong et al. | |
| 2015/0337197 A1 | 11/2015 | Jatsch et al. | |
| 2017/0062732 A1 * | 3/2017 | Jatsch | C07D 401/04 |

FOREIGN PATENT DOCUMENTS

| | | | | |
|---|---|---|---|---|
| CN | 102471602 A | 5/2012 | | |
| CN | 104024373 A | 9/2014 | | |
| EP | 2799515 | 11/2014 | | |
| JP | 2012521643 A | 9/2012 | | |
| KR | 20120060611 A * | 6/2012 | ......... | H01L 51/0072 |
| WO | WO-2011108901 A2 | 9/2011 | | |
| WO | WO-2012074210 A2 | 6/2012 | | |
| WO | WO-201301789 A1 | 1/2013 | | |
| WO | WO-2013100467 A1 | 7/2013 | | |
| WO | WO-2014038867 A1 | 3/2014 | | |
| WO | WO-2014094963 A1 | 6/2014 | | |
| WO | WO-2014129846 A1 * | 8/2014 | .......... | C07B 59/002 |
| WO | WO-2014129869 A1 * | 8/2014 | ............ | C09K 11/06 |
| WO | WO-2015124255 A1 | 8/2015 | | |

OTHER PUBLICATIONS

International Search Report for PCT/EP2015/001059 dated Aug. 12, 2015.
Kowshik, S., et al., "Ensuring Code Safety Without Runtime Checks for Real-Time Control Systems", CASES 2002 Proceedings of the International Conference on Compilers, Architecture, and Synthesis for Embedded Systems, Grenoble, France, Oct. 8-11, 2002, pp. 288-297; Association for Computing Machinery: New York, 2002.
Written Opinion of the International Searching Authority for PCT/EP2015/001059 dated Aug. 12, 2015.

* cited by examiner

*Primary Examiner* — Jennifer A Boyd
*Assistant Examiner* — Sean M DeGuire
(74) *Attorney, Agent, or Firm* — Faegre Drinker Biddle & Reath LLP

(57) ABSTRACT

The present invention relates to compounds which are suitable for use in electronic devices, and to electronic devices, in particular organic electroluminescent devices, comprising these compounds.

19 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2015/001059, filed May 22, 2015, which claims benefit of European Application No. 14002104.9, filed Jun. 18, 2014, both of which are incorporated herein by reference in their entirety.

The present invention relates to materials for use in electronic devices, in particular in organic electroluminescent devices, and to electronic devices, in particular organic electroluminescent devices, comprising these materials.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence. For quantum-mechanical reasons, an up to four-fold increase in the energy and power efficiency is possible using organometallic compounds as phosphorescence emitters. In general, however, there is still a need for improvement in the case of OLEDs, in particular also in the case of OLEDs which exhibit triplet emission (phosphorescence), for example with respect to efficiency, operating voltage and lifetime.

The properties of phosphorescent OLEDs are not only determined by the triplet emitters employed. In particular, the other materials used, such as matrix materials, Improvements in these materials and their charge-transport properties can thus also result in significant improvements in the OLED properties.

In accordance with the prior art, indolocarbazole derivatives, for example in accordance with WO 2007/063754 or WO 2008/056746, indenocarbazole derivatives, for example in accordance with WO 2010/136109, or fluorene or spirobifluorene derivatives, for example in accordance with WO 2012/074210, inter alfa, are employed as matrix materials for phosphorescent emitters in organic electroluminescent devices. Further improvements are desirable here, in particular with respect to the efficiency, the lifetime and the film formation of the materials.

The object of the present invention is the provision of compounds which are suitable for use in an OLED, in particular as matrix material for phosphorescent emitters. A further object of the present invention is to provide further organic semiconductors for organic electroluminescent devices so as to provide the person skilled in the art with a greater possible choice of materials for the production of OLEDs.

Surprisingly, it has been found that certain compounds described in greater detail below achieve this object, are highly suitable for use in OLEDs and result in improvements in the organic electroluminescent device. The improvements here relate, in particular, to the lifetime and/or the efficiency. In addition, these compounds have improved film-formation properties in the case of processing from solution, since they simultaneously have a high glass transition temperature and high solubilities, which enables processing from solution and subsequent drying by heating. The present invention therefore relates to these compounds and to electronic devices, in particular organic electroluminescent devices, which comprise compounds of this type.

The present invention relates to a compound of the formula (1) or formula (2),

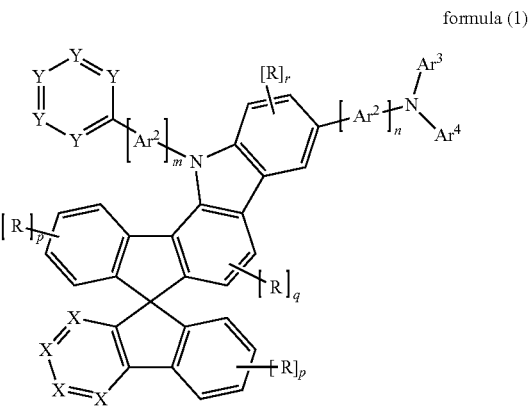

formula (1)

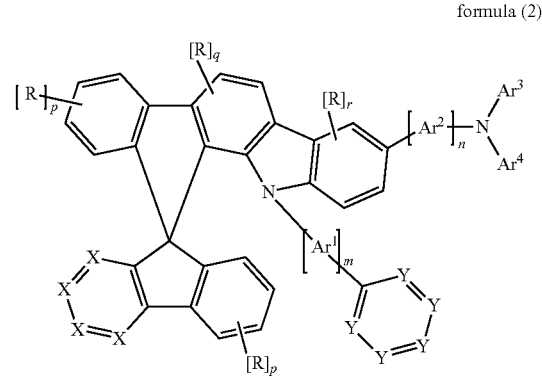

formula (2)

where the following applies to the symbols and indices used:

Y is on each occurrence, identically or differently, CR or N, with the proviso that at least one group Y stands for N;

X is on each occurrence, identically or differently, CR or N, where a maximum of two groups X stand for N; or two adjacent X stand for a group of the following formula (3) or (4) and the other X stand, identically or differently, for CR or N,

formula (3)

formula (4)

where ^ indicates the corresponding adjacent groups X in formula (1) or formula (2);

V is on each occurrence, identically or differently, NR, $C(R)_2$, O, S, BR, $Si(R)_2$ or C=O;

Z is on each occurrence, identically or differently, CR or N, where a maximum of two groups Z stand for N;

$Ar^1$ is an aromatic or heteroaromatic ring system having 5 to 40 aromatic ring atoms, which may be substituted by one or more radicals R;

Ar², Ar³, Ar⁴ are on each occurrence, identically or differently, an aromatic or heteroaromatic ring system having 5 to 40 aromatic ring atoms, which may be substituted by one or more radicals R; Ar² and Ar³ and/or Ar³ and Ar⁴ here may also be connected to one another by a single bond or by a group selected from C(R¹)₂, C(R¹)₂—C(R¹)₂, NR¹, O or S;

R is selected on each occurrence, identically or differently, from the group consisting of H, D, F, Cl, Br, I, CN, NO₂, N(Ar⁵)₂, N(R¹)₂, N(R¹¹)₂, C(=O)Ar⁵, C(=O)R¹, P(=O)(Ar⁵)₂, P(Ar⁵)₂, B(Ar⁵)₂, Si(Ar⁵)₃, Si(R¹)₂, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R¹, where one or more non-adjacent CH₂ groups may be replaced by R¹C=CR¹, C≡C, Si(R¹)₂, C=O, C=S, C=NR¹, P(=O)(R¹), SO, SO₂, NR¹, O, S or CONR¹ and where one or more H atoms may be replaced by D, F, Cl, Br, I, CN or NO₂, an aromatic or heteroaromatic ring system having 5 to 40 aromatic ring atoms, which may in each case be substituted by one or more radicals R¹, an aryloxy or heteroaryloxy group having 5 to 40 aromatic ring atoms, which may be substituted by one or more radicals R¹; two adjacent substituents R here may optionally form a monocyclic or polycyclic, aliphatic, aromatic or heteroaromatic ring system, which may be substituted by one or more radicals R¹;

Ar⁵ is on each occurrence, identically or differently, an aromatic or heteroaromatic ring system having 5 to 30 aromatic ring atoms, which may be substituted by one or more non-aromatic radicals R¹; two radicals Ar⁵ here which are bonded to the same N, P, B or Si atom may also be bridged to one another by a single bond or a bridge selected from N(R¹), C(R¹)₂, C(R¹)₂—C(R¹)₂, O or S;

R¹ is selected on each occurrence, identically or differently, from the group consisting of H, D, F, CN, an aliphatic hydrocarbon radical having 1 to 20 C atoms, or an aromatic or heteroaromatic ring system having 5 to 30 aromatic ring atoms, in which one or more H atoms may be replaced by D, F, CN or an alkyl group having 1 to 10 C atoms, where two or more adjacent substituents R¹ may form a mono- or polycyclic, aliphatic ring system with one another;

R¹¹ is selected on each occurrence, identically or differently, from the group consisting of H, D, F, CN, an aliphatic hydrocarbon radical having 1 to 20 C atoms, or an alkyl group having 1 to 10 C atoms;

m is 0 or 1;

n is 0 or 1;

p is on each occurrence, identically or differently, 0, 1, 2, 3 or 4;

q is 0, 1 or 2;

r is 0, 1, 2 or 3;

the following compound is excluded from the invention:

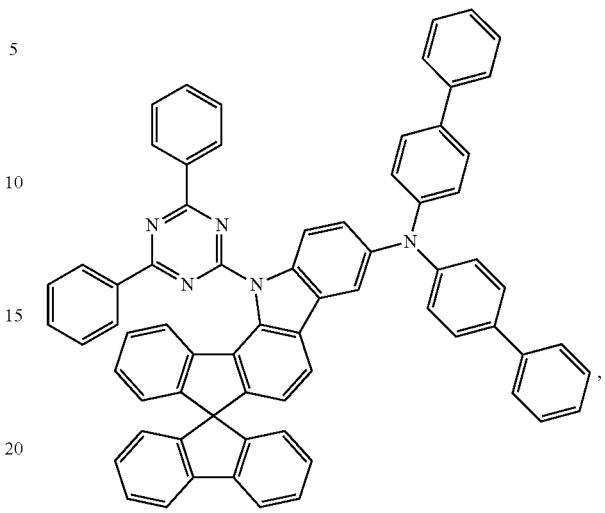

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. The heteroaryl group here preferably contains a maximum of three heteroatoms, a maximum of one of which is selected from O or S and the other heteroatoms are N. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl of bipyridine, are, by contrast, not referred to as aryl or heteroaryl group, but instead as aromatic or heteroaromatic ring system.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. The heteroaromatic ring system here preferably contains a maximum of three heteroatoms, a maximum of one of which is selected from O or S and the other heteroatoms are N, per heteroaryl group which is present in the ring system. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a short alkyl group.

For the purposes of the present invention, an aliphatic hydrocarbon radical or an alkyl group or an alkenyl or alkynyl group, which may contain 1 to 40 C atoms and in which, in addition, individual H atoms or CH₂ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octenylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-60 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from a combination of these systems.

Adjacent radicals or adjacent substituents in the sense of the present application are taken to mean substituents which are bonded to C atoms which are in turn bonded directly to one another or substituents which are bonded to the same C, Si, P, N or B atom.

In a preferred embodiment of the invention, X stands, identically or differently on each occurrence, for CR or N, where a maximum of one group X per ring stands for N; or two adjacent groups X stand for a group of the formula (3), where Z stands, identically or differently on each occurrence, for CR and V stands, identically or differently on each occurrence, for NR, $C(R)_2$, O or S, preferably for NR or $C(R)_2$, and the remaining X stand for CR. X particularly preferably stands, identically or differently on each occurrence, for $CR^1$.

Preferred embodiments of the compounds of the formula (1) are the compounds of the following formulae (5), (6) and (7), and preferred embodiments of the compounds of the formula (2) are the compounds of the following formulae (8), (9) and (10),

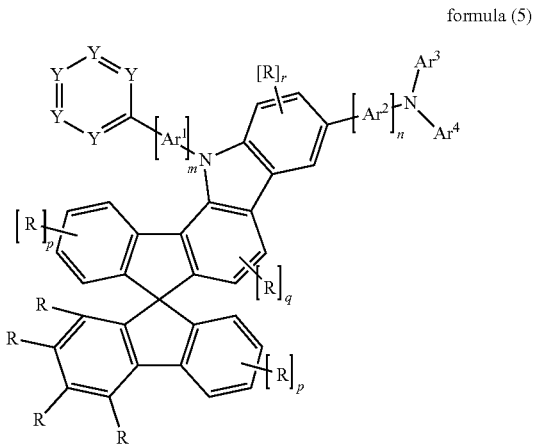

formula (5)

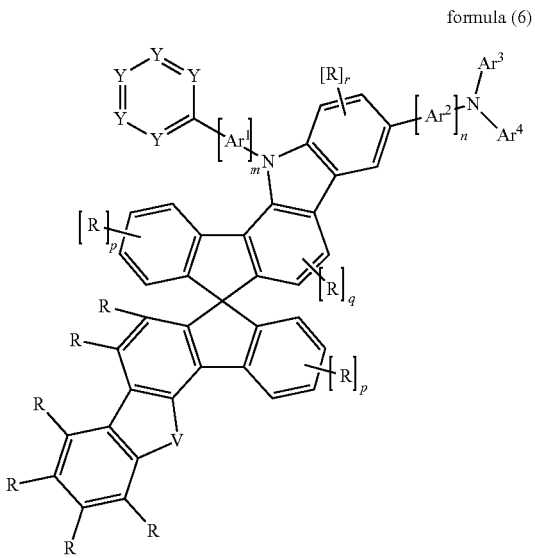

formula (6)

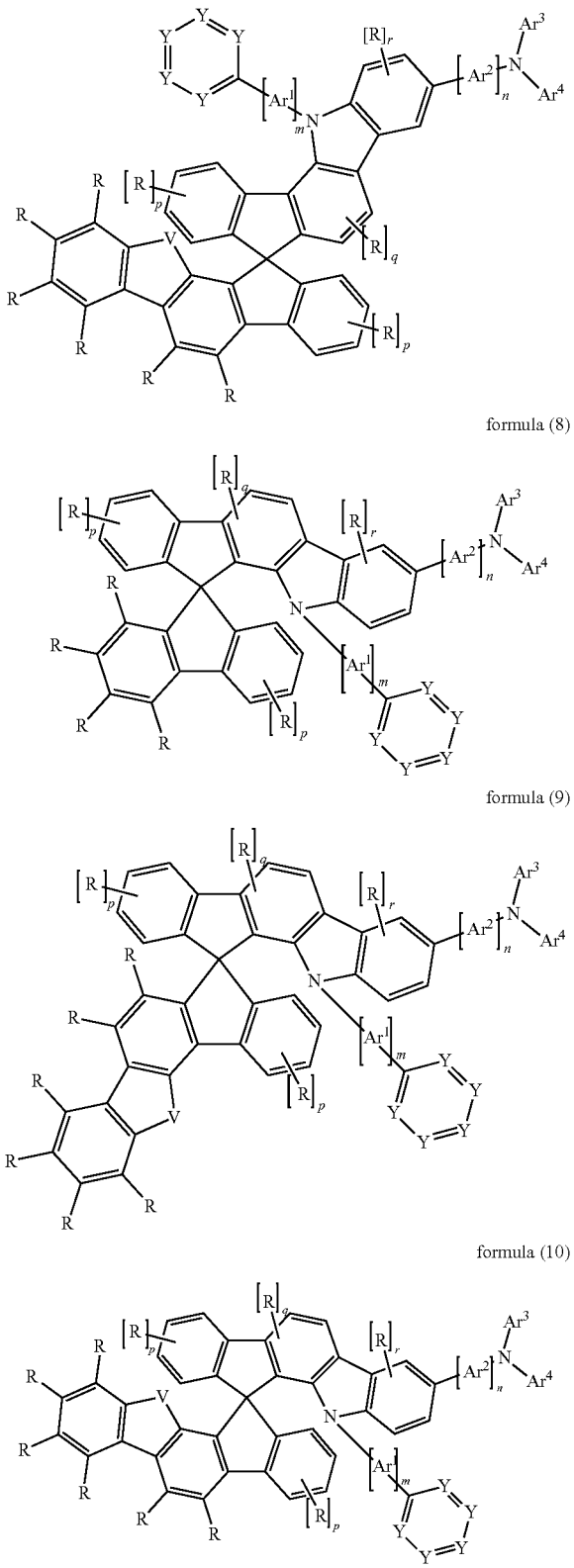

V=C(R)₂, the two radicals R form a ring with one another and thus form a Spiro system.

In a preferred embodiment of the invention, p is on each occurrence, identically or differently, 0, 1 or 2, particularly preferably 0 or 1 and very particularly preferably equal to 0.

Furthermore preferably, q is equal to 0 or 1, particularly preferably equal to 0.

Furthermore preferably, r is equal to 0 or 1, particularly preferably equal to 0.

Preferred embodiments of the structures of the formulae (5) to (10) are the structures of the formulae (5a) to (10a), where the symbols and indices used have the meanings given above. V here preferably stands for NR, C(R)₂, O or S, particularly preferably for NR. It may be preferred if, for formula (8a)
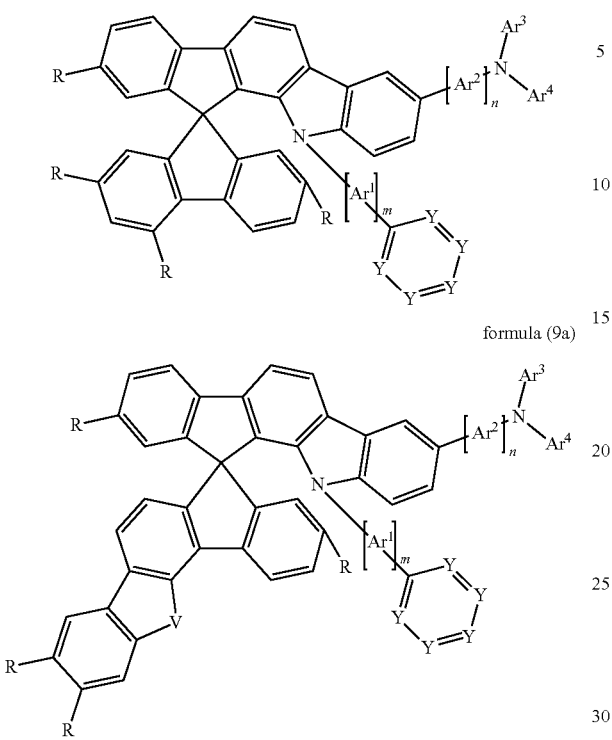
formula (9a)
formula (10a)
where the symbols and indices used have the meanings given above.
Particularly preferred embodiments of the structures of the formulae (5) to (10) are the structures of the formulae (5b) to (10b),
formula (5b)
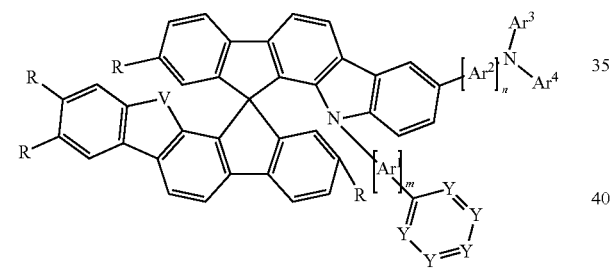
formula (6b)
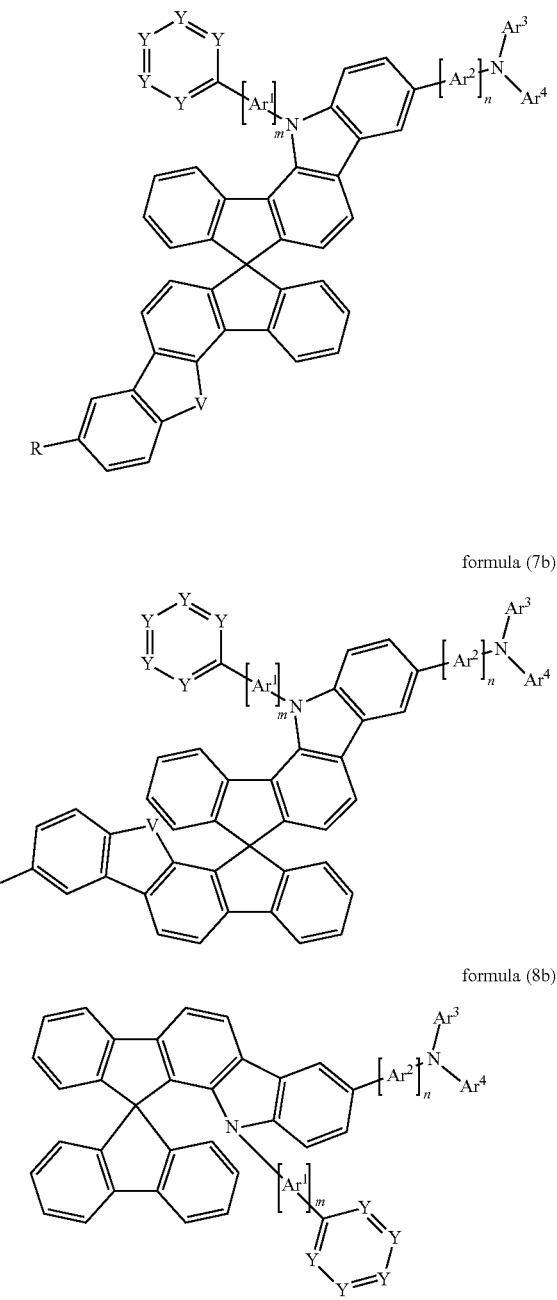
formula (7b)
formula (8b)
formula (9b)
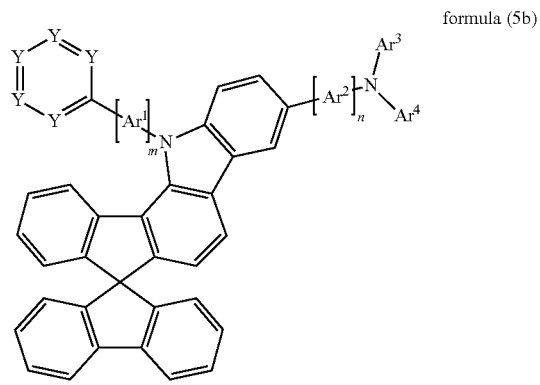

formula (10b)

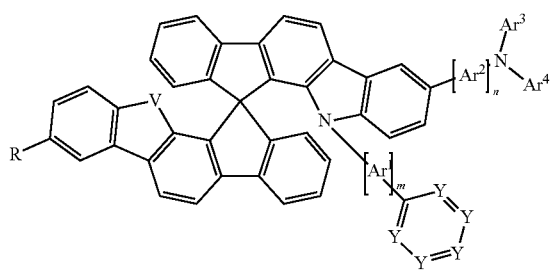

where the symbols and indices used have the meanings given above.

In a further preferred embodiment of the invention, R is selected, identically or differently on each occurrence, from the group consisting of H, D, F, CN, $N(Ar^5)_2$, $C(=O)Ar^5$, $P(=O)(Ar^5)_2$, straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which may be substituted by one or more radicals $R^1$, where one or more non-adjacent $CH_2$ groups may be replaced by O and where one or more H atoms may be replaced by D or F, or an aromatic or heteroaromatic ring system having 5 to 30 aromatic ring atoms, which may in each case be substituted by one or more radicals $R^1$. R is particularly preferably selected, identically or differently on each occurrence, from the group consisting of H, $N(Ar^5)_2$, a straight-chain alkyl group having 1 to 6 C atoms, in particular having 1 to 4 C atoms, or a branched or cyclic alkyl group having 3 to 8 C atoms, in particular having 3 to 6 C atoms, each of which may be substituted by one or more radicals $R^1$, but is preferably unsubstituted, or an aromatic or heteroaromatic ring system having 5 to 24 aromatic ring atoms, which may in each case be substituted by one or more radicals $R^1$.

If R stands for an aromatic or heteroaromatic ring system, this radical R is then preferably selected, identically or differently on each occurrence, from the same groups as indicated below as suitable groups for $Ar^1$ to $Ar^4$.

In compounds which are processed by vacuum evaporation, the alkyl groups preferably have not more than five C atoms, particularly preferably not more than 4 C atoms, very particularly preferably not more than 1 C atom. For compounds which are processed from solution, suitable compounds are also those which are substituted by alkyl groups, in particular branched alkyl groups, having up to 10 C atoms or which are substituted by oligoarylene groups, for example ortho-, meta-, para- or branched terphenyl or quaterphenyl groups.

In an embodiment of the invention, n=1 and m=0. In a further embodiment of the invention, n=0 and m=1. In still a further embodiment of the invention, n=m=1. In still a further embodiment of the invention, n=m=0.

In accordance with the invention, the compounds of the formulae (1) and (2) contain a six-membered heteroaryl ring group of the following formula, which is abbreviated to (Het-Ar) below:

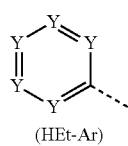

(HEt-Ar)

This group is bonded to $Ar^1$ for m=1 or to the nitrogen for m=0. At least one group Y in the group (Het-Ar) stands for N. In a preferred embodiment of the invention, one, two or three symbols Y stand for N and the other symbols Y stand for CR.

Preferred embodiments are the groups of the following formulae (Het-Ar-1) to (Het-Ar-10),

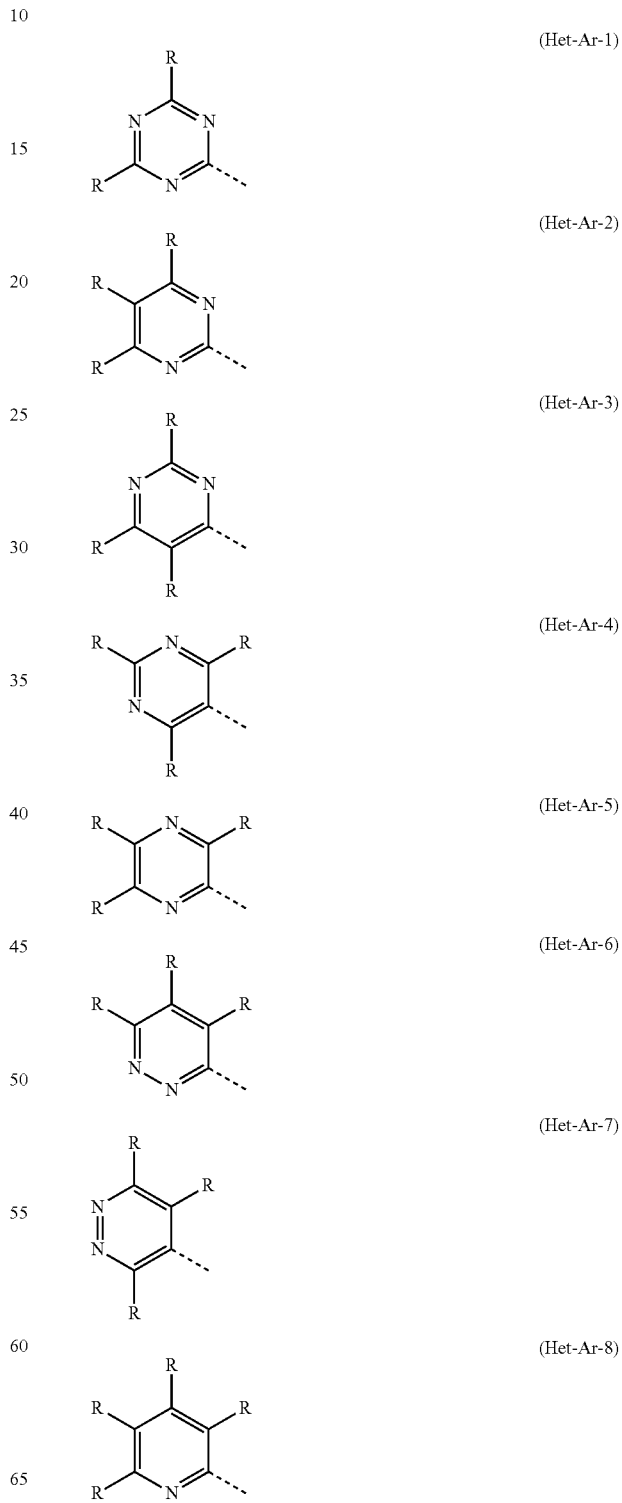

-continued

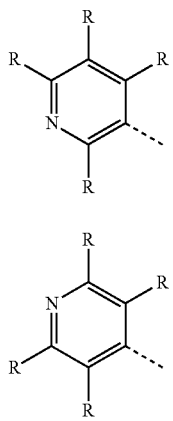
(Het-Ar-9)

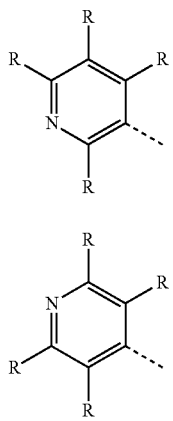
(Het-Ar-10)

where the dashed bond represents the bond to Ar¹ or, for m=0, the bond to the nitrogen, and R has the meanings given above.

Particular preference is given to the groups of the following formulae (Het-Ar-1a) to (Het-Ar-10b),

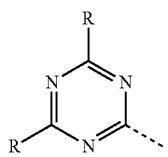
(Het-Ar-1a)

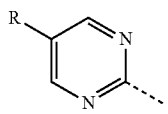
(Het-Ar-2a)

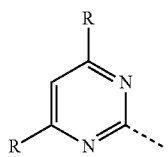
(Het-Ar-2b)

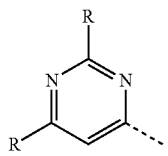
(Het-Ar-3a)

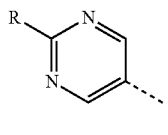
(Het-Ar-4a)

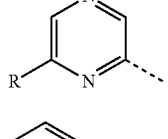
(Het-Ar-5a)

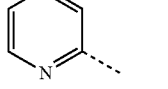
(Het-Ar-8a)

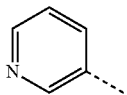
(Het-Ar-9a)

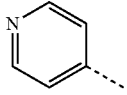
(Het-Ar-10a)

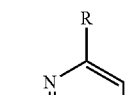
(Het-Ar-10b)

where the dashed bond represents the bond to Ar¹ or, for m=0, the bond to the nitrogen, and the symbols used have the meanings given above.

Very particular preference is given to the groups (Het-Ar-1a), (Het-Ar-2a) and (Het-Ar-2b).

In the groups (Het-Ar-1) to (Het-Ar-10), R preferably stands, identically or differently on each occurrence, for H, D or an aromatic or heteroaromatic ring system having 5 to 24 aromatic ring atoms, which may be substituted by one or more radicals $R^1$, in particular for H or for phenyl, biphenyl, in particular ortho-, meta- or para-biphenyl, terphenyl, in particular ortho-, meta-, para- or branched terphenyl, quaterphenyl, in particular ortho-, meta-, para- or branched quaterphenyl, fluorenyl, in particular 1-, 2-, 3- or 4-fluorenyl, spirobifluorenyl, in particular 1-, 2-, 3- or 4-spirobifluorenyl, dibenzofuranyl, in particular 1-, 2-, 3- or 4-dibenzofuranyl, or carbazolyl, in particular 1-, 2-, 3- or 4-carbazolyl, each of which may be substituted by one or more radicals $R^1$, but are preferably unsubstituted.

In the groups (Het-Ar-1a) to (Het-Ar-10a), the substituents R preferably stand for an aromatic or heteroaromatic ring system having 5 to 24 aromatic ring atoms, which may be substituted by one or more radicals $R^1$, in particular for phenyl, biphenyl, in particular ortho-, meta- or para-biphenyl, terphenyl, in particular ortho-, meta-, para- or branched terphenyl, quaterphenyl, in particular ortho-, meta-, para- or branched quaterphenyl, fluorenyl, in particular 1-, 2-, 3- or 4-fluorenyl, spirobifluorenyl, in particular 1-, 2-, 3- or 4-spirobifluorenyl, dibenzofuranyl, in particular 1-, 2-, 3- or 4-dibenzofuranyl, or carbazolyl, in particular 1-, 2-, 3- or 4-carbazolyl, each of which may be substituted by one or more radicals $R^1$, but are preferably unsubstituted.

In a preferred embodiment of the invention, m=1 and Ar¹ is an aromatic or heteroaromatic ring system having 5 to 24 aromatic ring atoms, preferably an aromatic ring system having 6 to 24 aromatic ring atoms, particularly preferably having 6 to 12 aromatic ring atoms, which may in each case be substituted by one or more radicals R. Suitable groups Ar¹ are selected from phenylene, in particular ortho-, meta- or para-phenylene, biphenyl, in particular ortho-, meta- or para-biphenyl, terphenyl, in particular ortho-, meta-, para- or branched terphenyl, quaterphenyl, in particular ortho-, meta-, para- or branched quaterphenyl, fluorene, in particular 2,7-linked fluorene, spirobifluorene, in particular 2,7- or 2,2'- or 4,4'-linked spirobifluorene, naphthalene, in particular 1,4- or 2,6-linked naphthalene, indole, benzofuran, benzothiophene, carbazole, in particular 2,7- or 3,6-linked carbazole, dibenzofuran, dibenzothiophene, indenocarbazole, indolocarbazole, pyridine, pyrimidine, pyrazine, pyridazine, triazine, phenanthrene, triphenylene or combinations of two or three of these groups, each of which may be substituted by one or more radicals R. $Ar^1$ particularly preferably stands for an aromatic ring system selected from the group consisting of phenylene, in particular ortho-, meta- or para-phenylene, biphenyl, in particular ortho-, meta- or para-biphenyl, or terphenyl, in particular ortho-, meta-, para- or branched terphenyl. The group (Het-Ar) here is bonded to $Ar^1$ at any desired site.

In a further preferred embodiment of the invention, m=0, and the group $Ar^1$ is not present.

In a further preferred embodiment of the invention, the aromatic groups in the group $Ar^1$ are not para-linked, i.e. they are preferably not paraphenylene, para-biphenyl, para-terphenyl or para-quaterphenyl, but instead, for example, the respective ortho- or meta-linked structures.

In accordance with the invention, the compounds of the formulae (1) and (2) contain a group of the formula $-[Ar^2]_n-N(Ar^3)(Ar^4)$ in the para-position to the nitrogen atom of the spirocarbazole unit.

$Ar^2$ and $Ar^3$ here may be connected to one another for n=1 and/or $Ar^3$ and $Ar^4$ may also be connected to one another by a single bond or by a group selected from $C(R^1)_2$, $C(R^1)_2-C(R^1)_2$, $NR^1$, O or S, preferably by a single bond. The linking of $Ar^2$ and $Ar^3$ to one another or of $Ar^3$ and $Ar^4$ to one another preferably in each case takes place ortho to the position of the link to the nitrogen atom.

In an embodiment of the invention, n=1, and $Ar^2$ and $Ar^3$ are connected to one another by a single bond. In a further embodiment of the invention, n=0 or 1, and $Ar^3$ and $Ar^4$ are connected to one another by a single bond. In still a further embodiment of the invention, n=0 or 1, and none of the groups $Ar^2$, $Ar^3$ and $Ar^4$ are connected to one another.

Particularly preferably, n=1, and $Ar^2$ and $Ar^3$ are connected to one another by a single bond.

$Ar^2$ is preferably an aromatic or heteroaromatic ring system having 6 to 24 aromatic ring atoms, preferably having 6 to 12 aromatic ring atoms, which may in each case be substituted by one or more radicals R. $Ar^2$ is particularly preferably selected from the group consisting of phenylene, in particular ortho-, meta- or para-phenylene, or biphenyl, in particular ortho-, meta- or para-biphenyl, each of which may be substituted by one or more radicals R, but are preferably unsubstituted. $Ar^2$ is very particularly preferably an unsubstituted phenylene group. This applies in particular if $Ar^2$ is connected to $Ar^3$ by a single bond.

$Ar^3$ and $Ar^4$ are preferably, identically or differently on each occurrence, an aromatic or heteroaromatic ring system having 6 to 24 aromatic ring atoms, which may in each case be substituted by one or more radicals R. Particularly preferred groups $Ar^3$ and $Ar^4$ are selected, identically or differently on each occurrence, from the group consisting of phenyl, biphenyl, in particular ortho-, meta- or para-biphenyl, terphenyl, in particular ortho-, meta-, para- or branched terphenyl, quaterphenyl, in particular ortho-, meta-, para- or branched quaterphenyl, fluorenyl, in particular 1-, 2-, 3- or 4-fluorenyl, spirobifluorenyl, in particular 1-, 2-, 3- or 4-spirobifluorenyl, naphthyl, in particular 1- or 2-naphthyl, indolyl, benzofuranyl, benzothiophenyl, carbazolyl, in particular 1-, 2-, 3- or 4-carbazolyl, dibenzofuranyl, in particular 1-, 2-, 3- or 4-dibenzofuranyl, dibenzothiophenyl, in particular 1-, 2-, 3- or 4-dibenzothiophenyl, indenocarbazolyl, indolocarbazolyl, pyridinyl, in particular 2-, 3- or 4-pyridinyl, pyrimidinyl, in particular 2-, 4- or 5-pyrimidinyl, pyrazinyl, pyridazinyl, triazinyl, phenanthrenyl, triphenylenyl or combinations of two, three or four of these groups, each of which may be substituted by one or more radicals R. $Ar^3$ and $Ar^4$ particularly preferably stand, identically or differently on each occurrence, for an aromatic ring system having 6 to 24 aromatic ring atoms, which may be substituted by one or more radicals R, in particular selected from the group consisting of benzene, biphenyl, in particular ortho-, meta- or para-biphenyl, terphenyl, in particular ortho-, meta-, para- or branched terphenyl, quaterphenyl, in particular ortho-, meta-, para- or branched quaterphenyl, fluorenyl, in particular 1-, 2-, 3- or 4-fluorenyl, or spirobifluorenyl, in particular 1-, 2-, 3- or 4-spirobifluorenyl.

Particularly preferred groups of the formula $-[Ar^2]_n-N(Ar^3)(Ar^4)$ are those in which n=1 and $Ar^2$ stands for a phenyl group which is connected to $Ar^3$ by a single bond. This results in the formation of a carbazole or a carbazole derivative.

Particularly preferred groups of the formula $-[Ar^2]_n-N(Ar^3)(Ar^4)$ are the groups of the following formula (GARB),

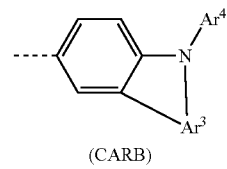

(CARB)

where $Ar^3$ and $Ar^4$ have the meanings given above and in particular the preferred meanings given above and the dashed bond represents the bond from the group (CARB) to the spirocarbazole skeleton in formula (1) or formula (2).

Preferred embodiments of the formula (CARB) are the groups of the following formulae (CARB-1) to (CARB-5),

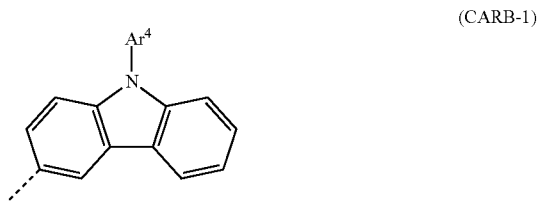

(CARB-1)

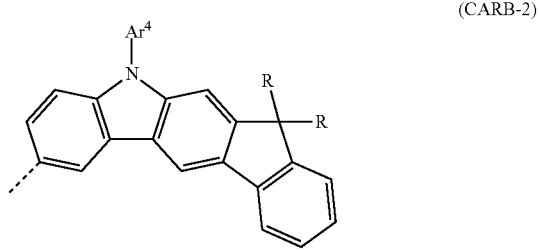

(CARB-2)

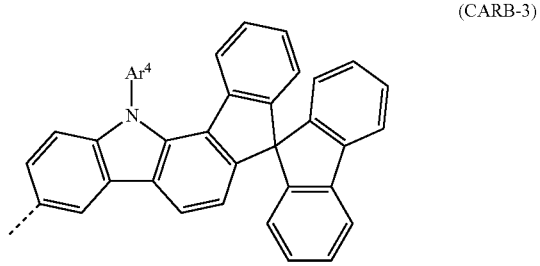

(CARB-3)

(CARB-4)

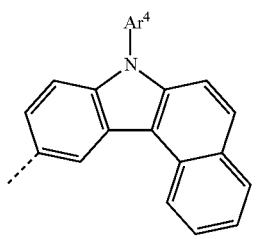

(CARB-5)

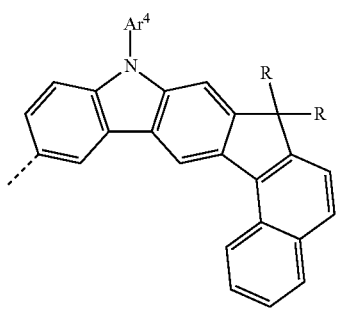

where Ar$^4$ has the meanings given above and the structures may be substituted by one or more radicals R.

The radicals R explicitly drawn in in formulae (CARB-2) and (CARB-4) are preferably selected from alkyl groups having 1 to 4 C atoms or aromatic ring systems having 6 to 12 aromatic ring atoms, in particular methyl.

If the compounds of the formula (1) or (2) or the preferred embodiments are used as matrix material for a phosphorescent emitter or in a layer which is directly adjacent to a phosphorescent layer, it is furthermore preferred for the triplet energy of the compounds to be the same or higher than that of the phosphorescent emitter. This can be achieved, in particular for green- and blue-phosphorescent emitters, which have a higher triplet energy than red-phosphorescent emitters by the compound according to the invention containing no condensed aryl or heteroaryl groups in which more than two six-membered rings are condensed directly onto one another. Such compounds are therefore a further preferred embodiment of the invention. In particular, it is preferred for this use that the radicals R, R$^1$ and Ar$^1$ to Ar$^4$ contain no condensed aryl or heteroaryl groups in which two or more six-membered rings are condensed directly onto one another.

The preferred embodiments indicated above can be combined with one another as desired in a particularly preferred embodiment of the invention, the preferences indicated above occur simultaneously.

Examples of preferred compounds in accordance with the embodiments indicated above are the compounds shown in the following table.

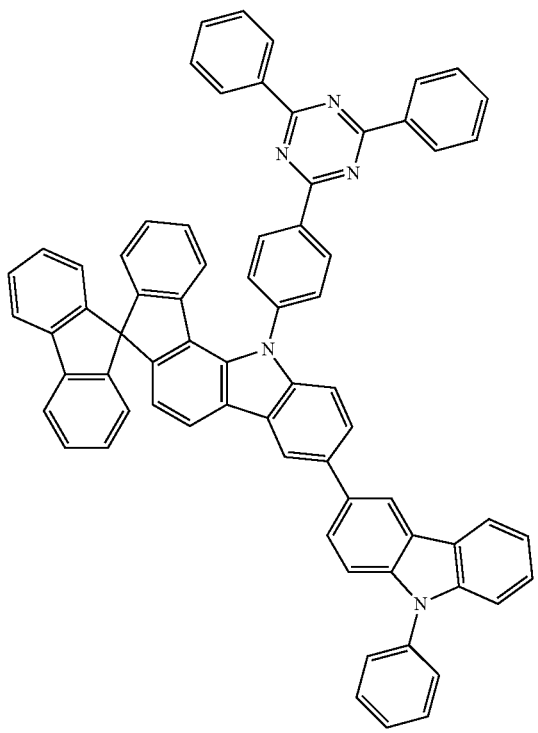 [SMILES: c1ccc(-c2nc(-c3ccccc3)nc(-c3ccc(-n4c5ccc(-c6ccc7c(c6)c6ccccc6n7-c6ccccc6)cc5c5ccc6c(c54)-c4ccccc4C64c5ccccc5-c5ccccc54)cc3)n2)cc1]

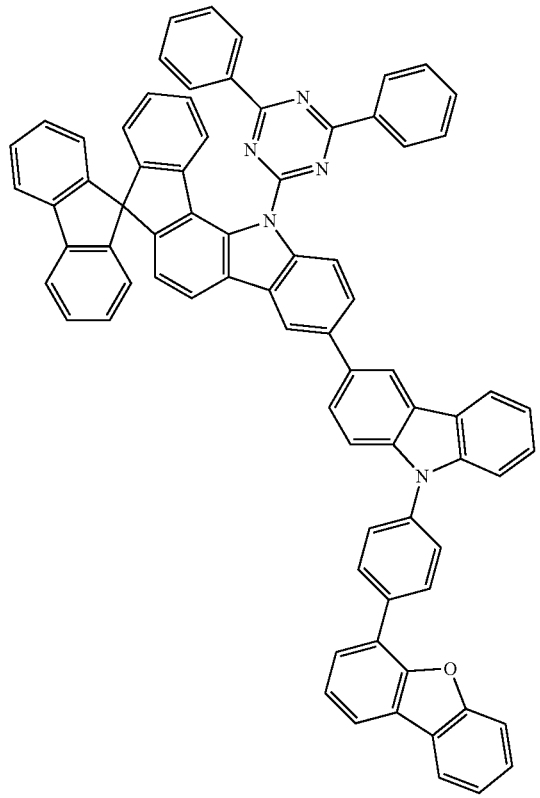 [SMILES: c1ccc(-c2nc(-c3ccccc3)nc(-n3c4ccc(-c5ccc6c(c5)c5ccccc5n6-c5ccc(-c6cccc7c6oc6ccccc67)cc5)cc4c4ccc5c(c43)-c3ccccc3C53c4ccccc4-c4ccccc43)n2)cc1]
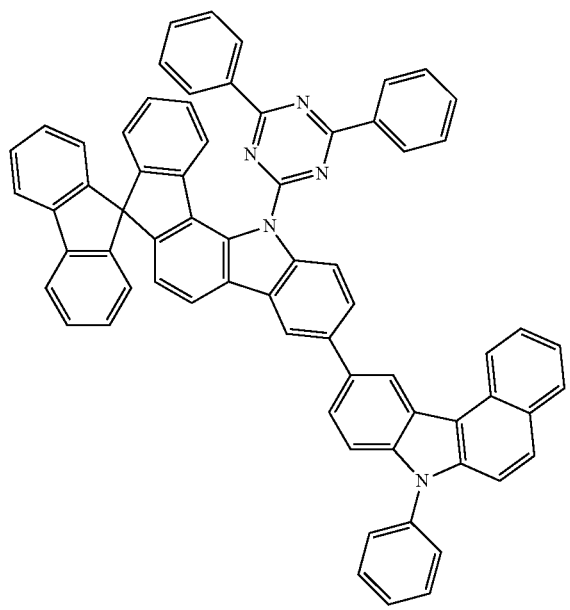 [SMILES: c1ccc(-c2nc(-c3ccccc3)nc(-n3c4ccc(-c5ccc6c(c5)c5c7ccccc7ccc5n6-c5ccccc5)cc4c4ccc5c(c43)-c3ccccc3C53c4ccccc4-c4ccccc43)n2)cc1]

-continued
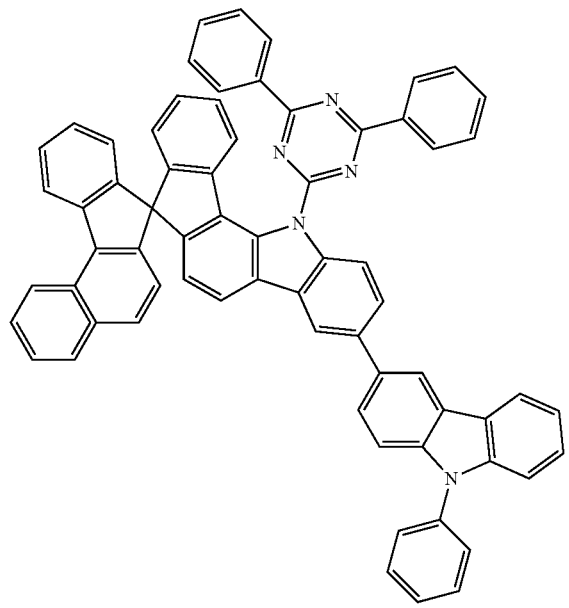
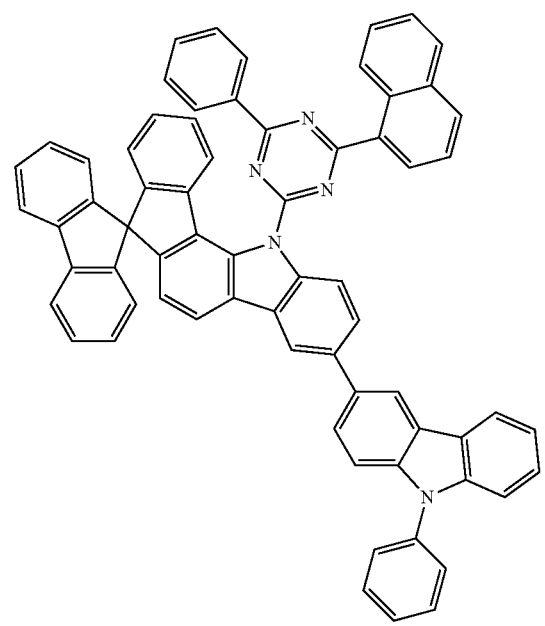 [SMILES: c1ccc(-c2nc(-c3cccc4ccccc34)nc(-n3c4ccc(-c5ccc6c(c5)c5ccccc5n6-c5ccccc5)cc4c4ccc5c(c43)-c3ccccc3C53c4ccccc4-c4ccccc43)n2)cc1]

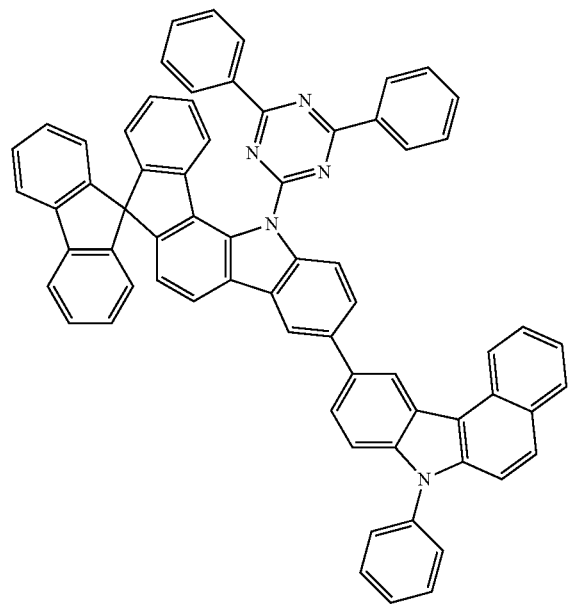 [SMILES: c1ccc(-c2nc(-c3ccccc3)nc(-n3c4ccc(-c5ccc6c(c5)c5c7ccccc7ccc5n6-c5ccccc5)cc4c4ccc5c(c43)-c3ccccc3C53c4ccccc4-c4ccccc43)n2)cc1]
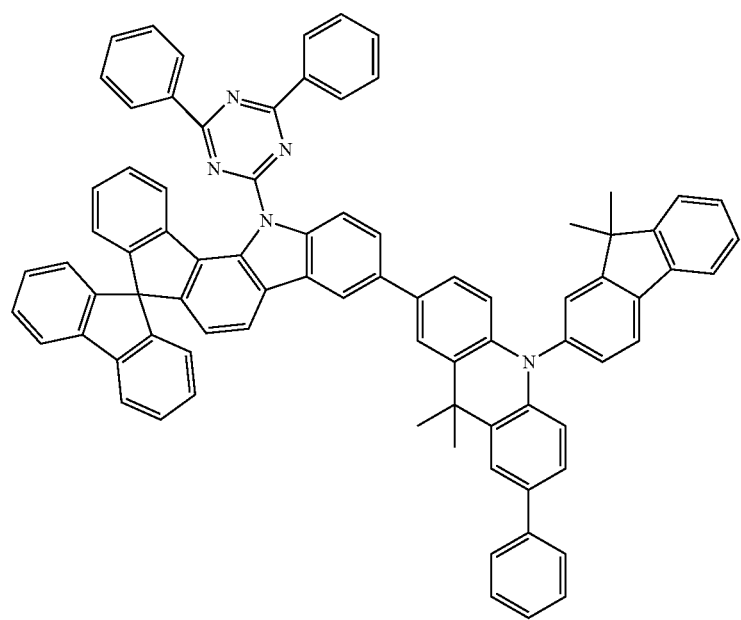 [SMILES: CC1(C)c2ccccc2-c2ccc(N3c4ccc(-c5ccccc5)cc4C(C)(C)c4cc(-c5ccc6c(c5)c5ccc7c(c5n6-c5nc(-c6ccccc6)nc(-c6ccccc6)n5)-c5ccccc5C75c6ccccc6-c6ccccc65)ccc43)cc21]

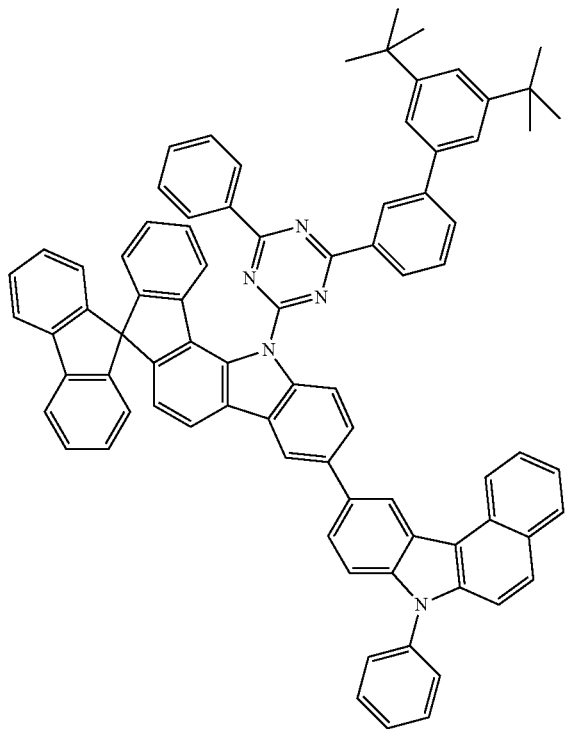 [SMILES: CC(C)(C)c1cc(-c2cccc(-c3nc(-c4ccccc4)nc(-n4c5ccc(-c6ccc7c(c6)c6c8ccccc8ccc6n7-c6ccccc6)cc5c5ccc6c(c54)-c4ccccc4C64c5ccccc5-c5ccccc54)n3)c2)cc(C(C)(C)C)c1]
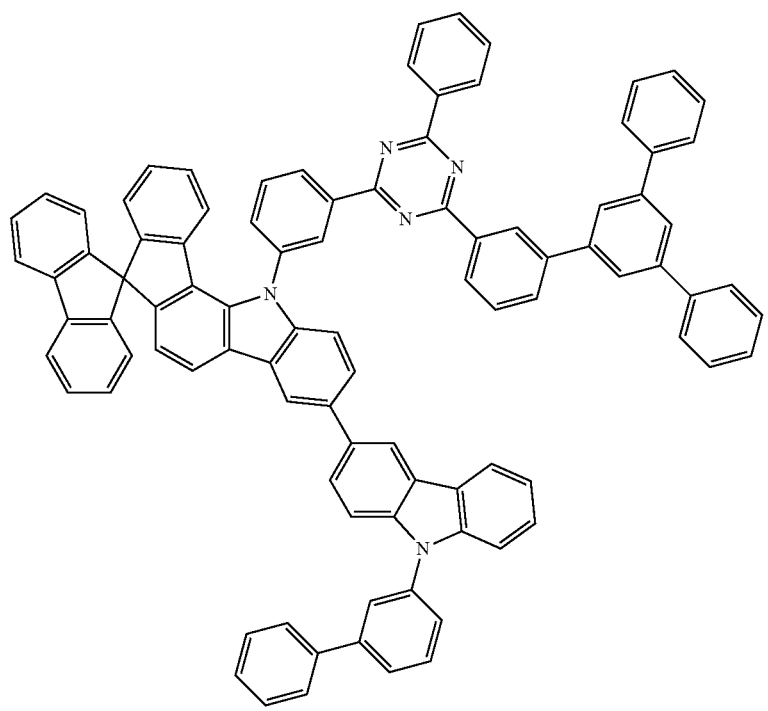 [SMILES: c1ccc(-c2cc(-c3ccccc3)cc(-c3cccc(-c4nc(-c5ccccc5)nc(-c5cccc(-n6c7ccc(-c8ccc9c(c8)c8ccccc8n9-c8cccc(-c9ccccc9)c8)cc7c7ccc8c(c76)-c6ccccc6C86c7ccccc7-c7ccccc76)c5)n4)c3)c2)cc1]

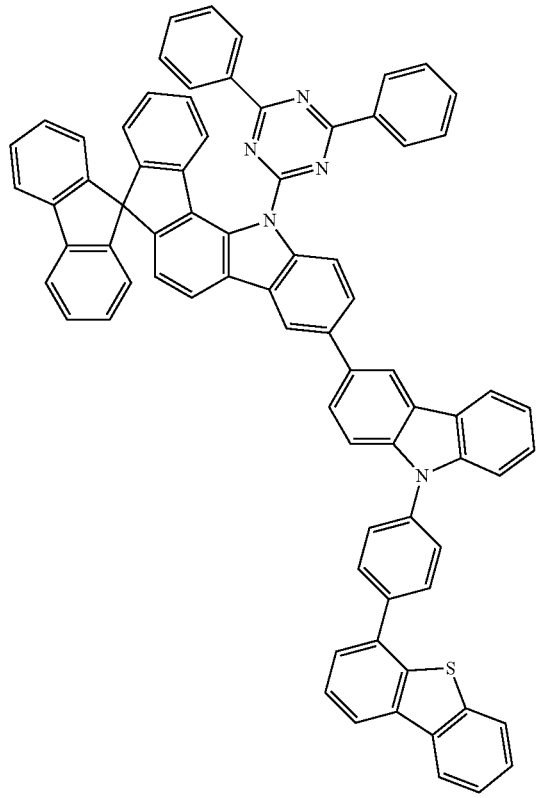
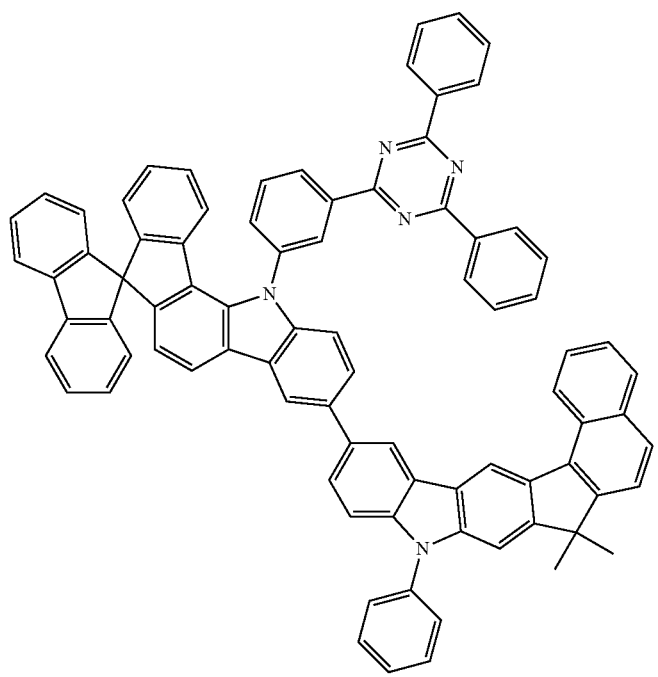 [SMILES: CC1(C)c2cc3c(cc2-c2c1ccc1ccccc21)c1cc(-c2ccc4c(c2)c2ccc5c(c2n4-c2cccc(-c4nc(-c6ccccc6)nc(-c6ccccc6)n4)c2)-c2ccccc2C52c4ccccc4-c4ccccc42)ccc1n3-c1ccccc1]

-continued

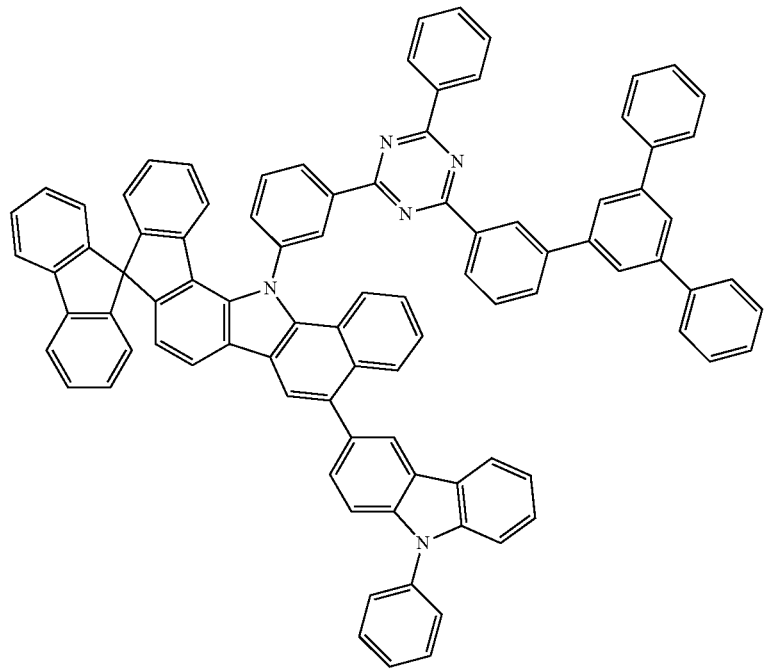 [SMILES: c1ccc(-c2cc(-c3ccccc3)cc(-c3cccc(-c4nc(-c5ccccc5)nc(-c5cccc(-n6c7c8c(ccc7c7cc(-c9ccc%10c(c9)c9ccccc9n%10-c9ccccc9)c9ccccc9c76)C6(c7ccccc7-c7ccccc76)c6ccccc6-8)c5)n4)c3)c2)cc1]
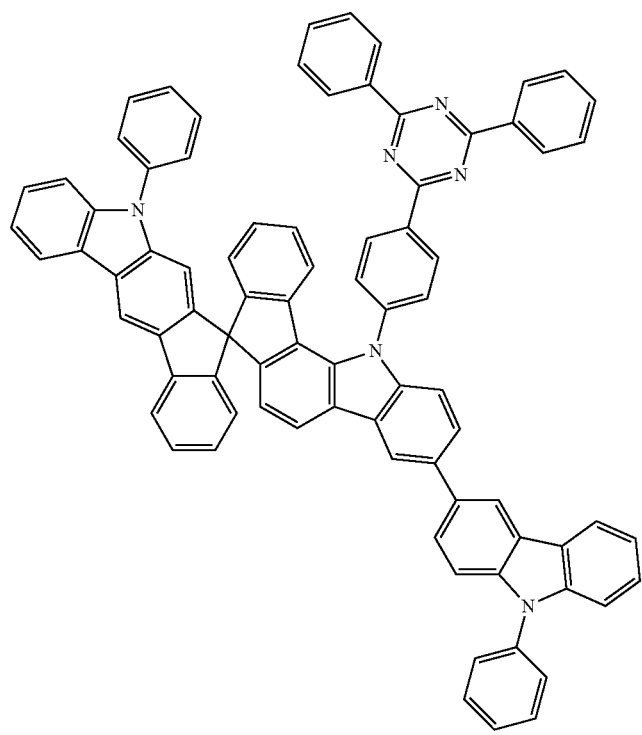 [SMILES: c1ccc(-c2nc(-c3ccccc3)nc(-c3ccc(-n4c5ccc(-c6ccc7c(c6)c6ccccc6n7-c6ccccc6)cc5c5ccc6c(c54)-c4ccccc4C64c5ccccc5-c5cc6c7ccccc7n(-c7ccccc7)c6cc54)cc3)n2)cc1]

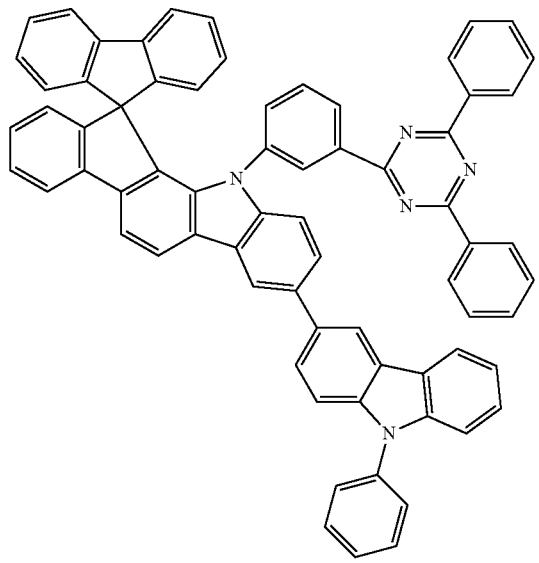 [SMILES: c1ccc(-c2nc(-c3ccccc3)nc(-c3cccc(-n4c5ccc(-c6ccc7c(c6)c6ccccc6n7-c6ccccc6)cc5c5ccc6c(c54)C4(c5ccccc5-c5ccccc54)c4ccccc4-6)c3)n2)cc1]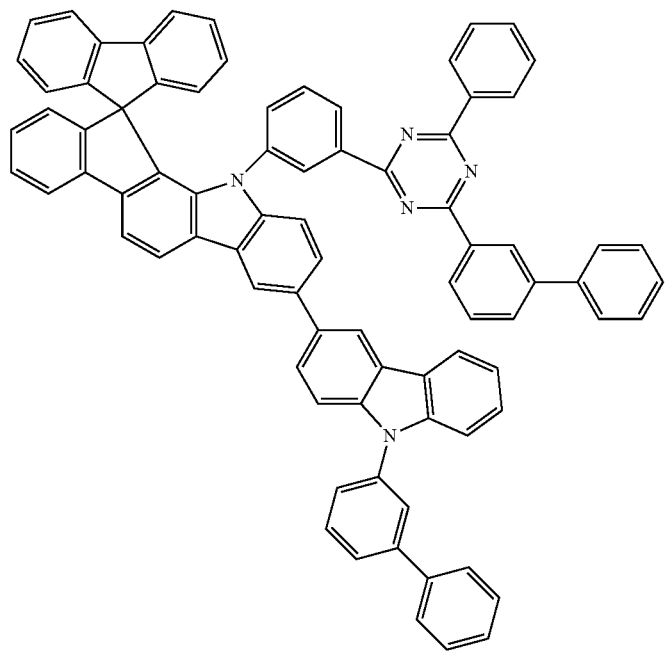 [SMILES: c1ccc(-c2cccc(-c3nc(-c4ccccc4)nc(-c4cccc(-n5c6ccc(-c7ccc8c(c7)c7ccccc7n8-c7cccc(-c8ccccc8)c7)cc6c6ccc7c(c65)C5(c6ccccc6-c6ccccc65)c5ccccc5-7)c4)n3)c2)cc1]

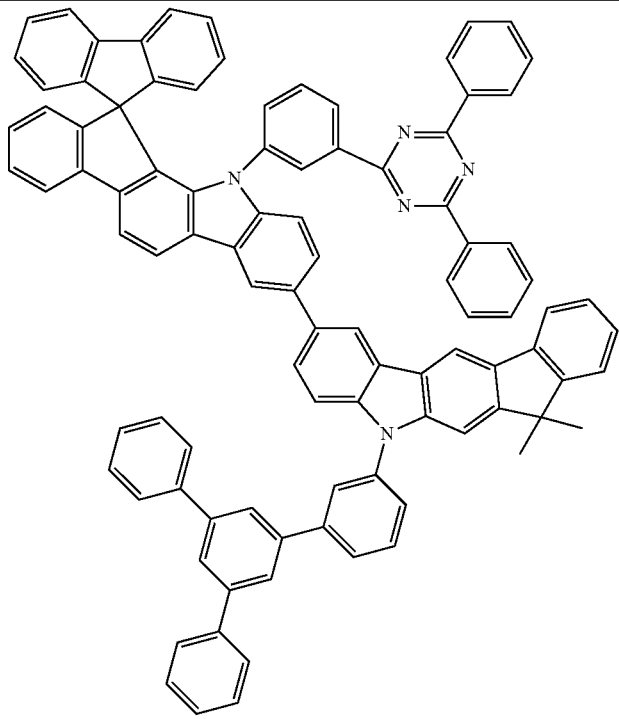
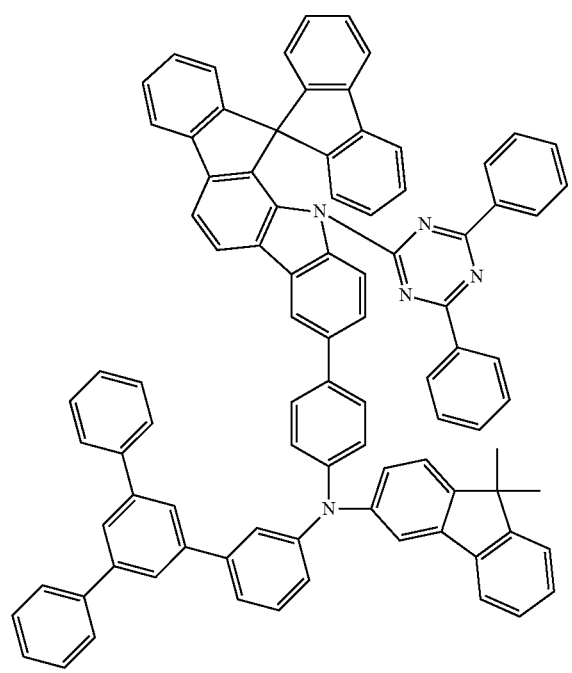 [SMILES: CC1(C)c2ccccc2-c2cc(N(c3ccc(-c4ccc5c(c4)c4ccc6c(c4n5-c4nc(-c5ccccc5)nc(-c5ccccc5)n4)C4(c5ccccc5-c5ccccc54)c4ccccc4-6)cc3)c3cccc(-c4cc(-c5ccccc5)cc(-c5ccccc5)c4)c3)ccc21]

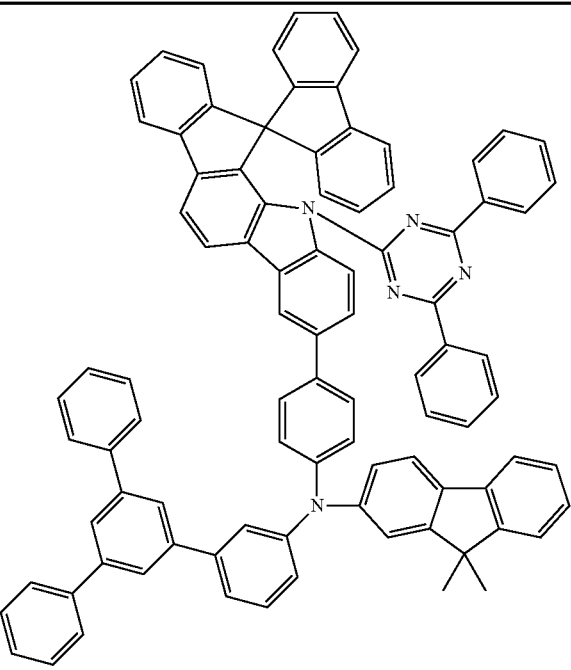
The basic structures of the compounds according to the invention can be prepared by routes outlined in Schemes 1a and 1b. Further derivatisation can be carried out in accordance with Schemes 2 and/or 3.
Scheme 1a
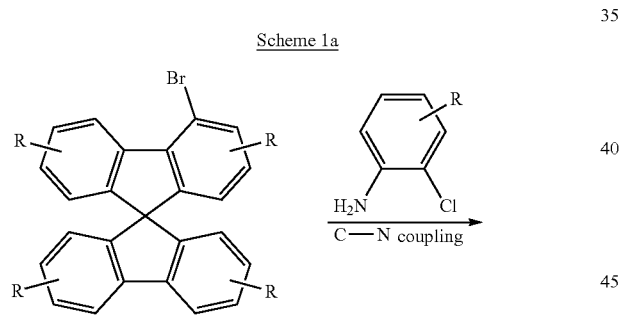
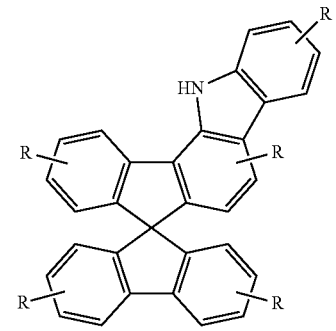
-continued
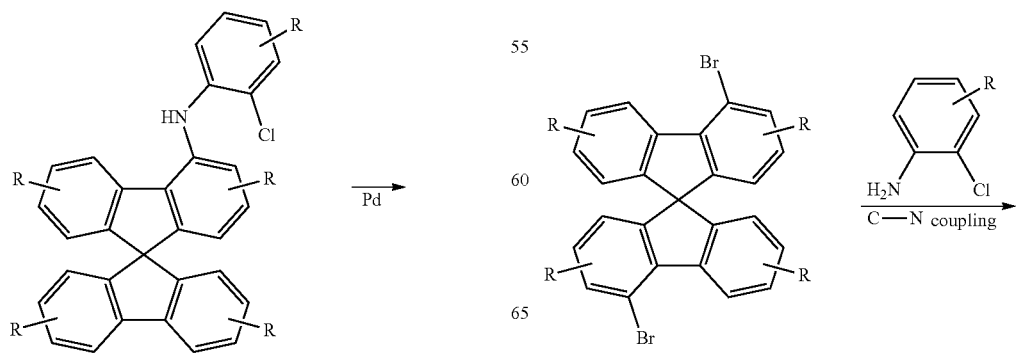

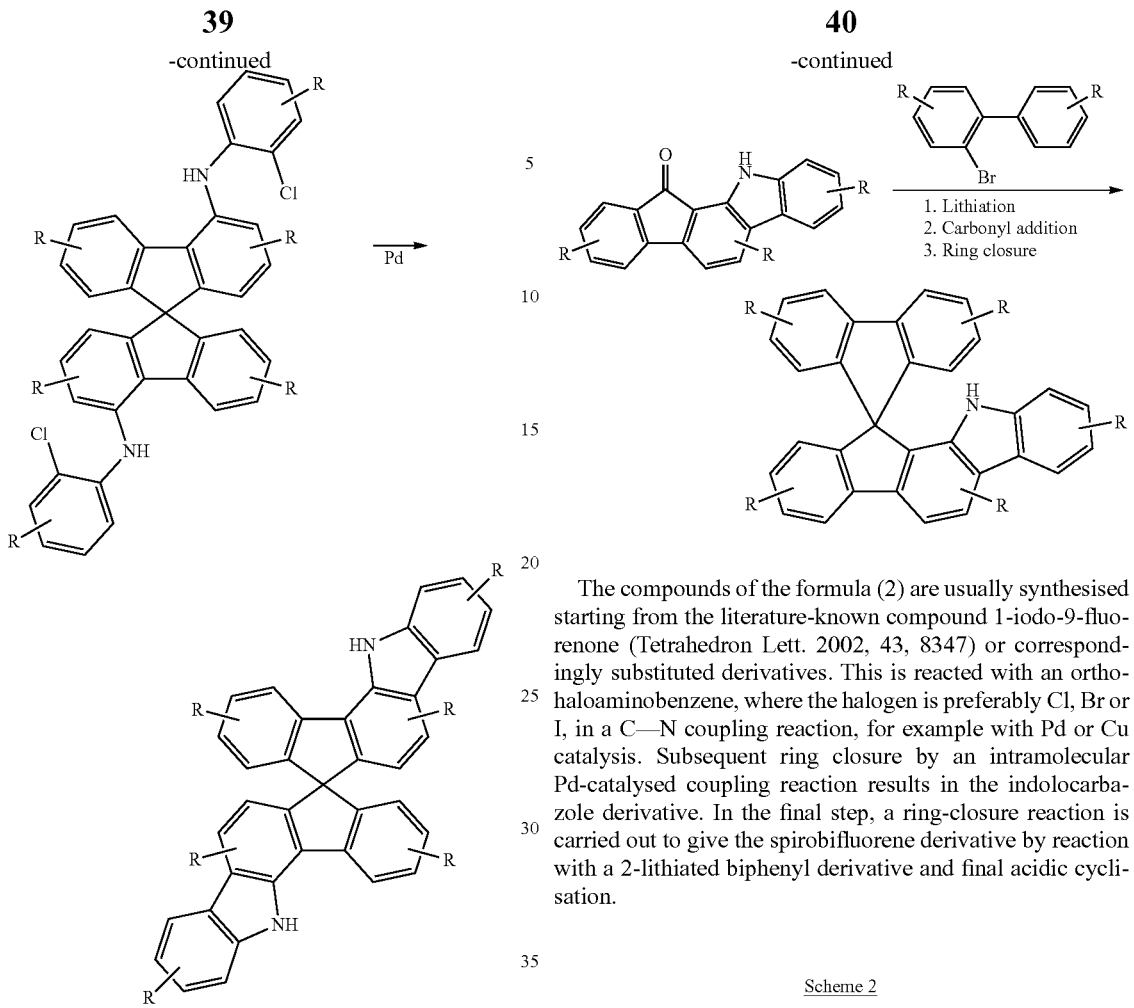

The compounds of the formula (2) are usually synthesised starting from the literature-known compound 1-iodo-9-fluorenone (Tetrahedron Lett. 2002, 43, 8347) or correspondingly substituted derivatives. This is reacted with an ortho-haloaminobenzene, where the halogen is preferably Cl, Br or I, in a C—N coupling reaction, for example with Pd or Cu catalysis. Subsequent ring closure by an intramolecular Pd-catalysed coupling reaction results in the indolocarbazole derivative. In the final step, a ring-closure reaction is carried out to give the spirobifluorene derivative by reaction with a 2-lithiated biphenyl derivative and final acidic cyclisation.

The compounds of the formula (1) are usually synthesised starting from the literature-known compounds 4-bromo-9,9'-spirobifluorene (Org. Lett. 2009, 11, 2607) or 4,4'-dibromo-9,9'-spirobifluorene (Org. Lett. 2010, 12, 5648) or correspondingly substituted derivatives. These are reacted with an orthohaloaminobenzene, where the halogen is preferably Cl, Br or I, in a C—N coupling reaction, for example with Pd or Cu catalysis. Subsequent ring closure by an intramolecular Pd-catalysed coupling reaction results in compounds of the formula (1).

Scheme 1b

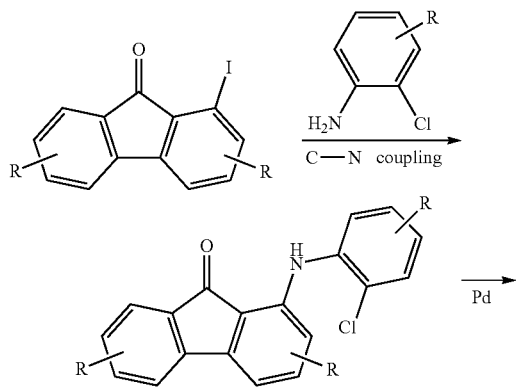

Scheme 2

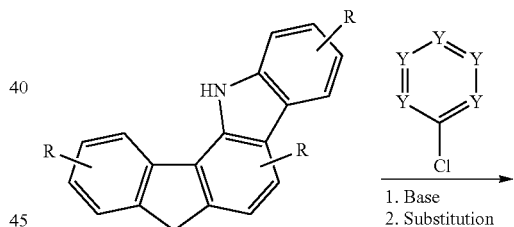

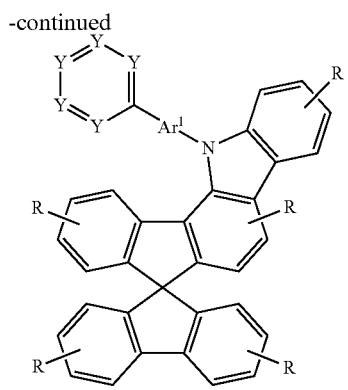

Precursors of the compounds of the formula (1) where m=0 which do not yet contain an amino or carbazole group as substituent are obtained by nucleophilic aromatic substitution by a group (Het-Ar)-Hal, where the halogen as leaving group is preferably Cl or Br.

Precursors of the compounds of the formula (1) where m=1 which do not yet contain an amino or carbazole group as substituent are obtained by C—N coupling reactions with a group (Het-Ar)—$Ar^1$-Hal, for example Hartwig-Buchwald coupling or Ullmann coupling, where the halogen is preferably Br or I.

The reactions described in Scheme 2 can also be carried out analogously with indolocarbazole derivatives in accordance with Scheme 1b and result in the corresponding precursors of the compounds of the formula (2).

Scheme 3

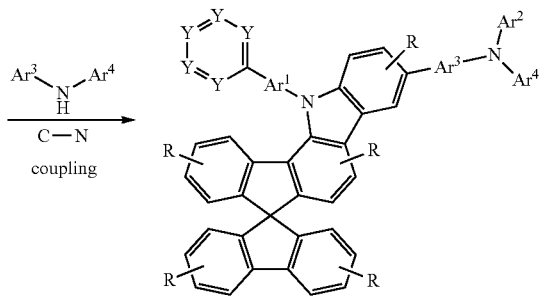

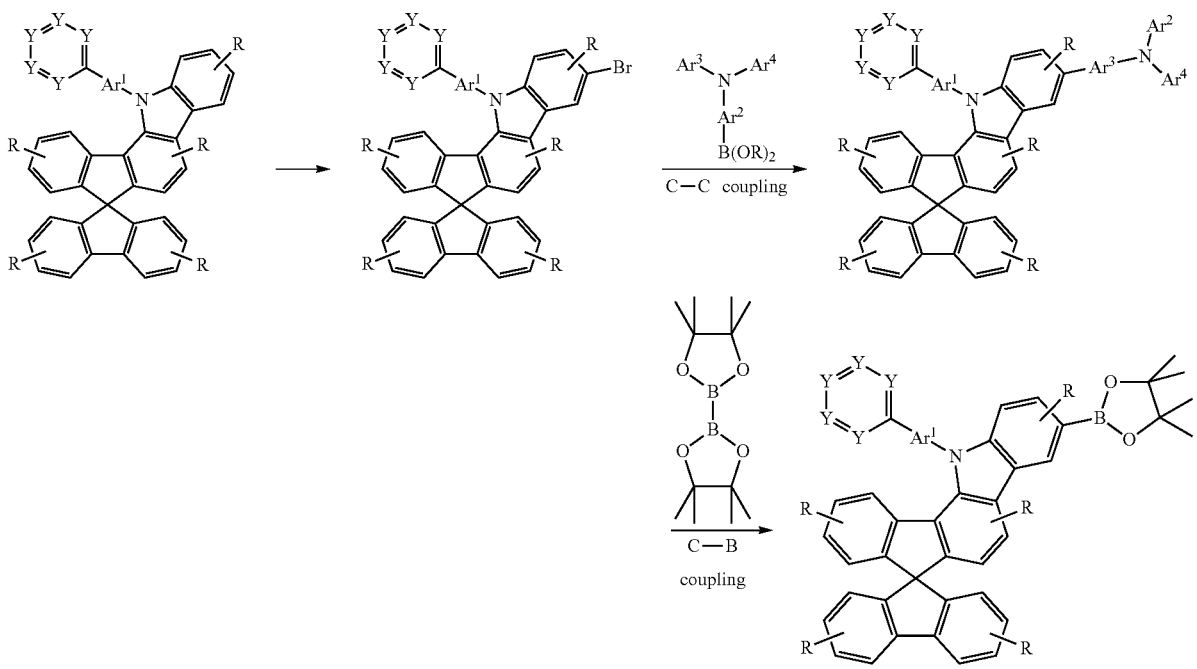

The further derivatisation can be carried out by bromination of the carbazole derivatives, for example by reaction with N-bromosuccinimide or elemental bromine. Subsequent Pd-catalysed C—N coupling reactions, for example Hartwig-Buchwald or Ullmann coupling, or C—C coupling reactions, for example Suzuki, Negishi, Yamamoto, Grignard-Cross or Stifle coupling, result in compounds of the formula (1) according to the invention where n=0 or n=1. A reaction with a boronic acid derivative of an unsubstituted carbazole, i.e., for example, with a compound $Ar^3$—NH—$Ar^2$—$B(OR)_2$, can also be carried out analogously, where the proton on the carbazole is substituted in a further step. Furthermore, a Pd-catalysed reaction of the bromide with, for example, bis(pinacolato)diborane enables the preparation of corresponding boronic acid esters, which can be reacted in a C—C coupling reaction.

The bromination described and subsequent reaction to give boronic acid esters can also be carried out analogously in the absence of the group Het-Ar—$Ar^1$ or Het-Ar, so that this group can also not be introduced until the final step.

The reactions described can also be carried out analogously with derivatives in accordance with Scheme 1b or N-substituted derivatives thereof in accordance with Scheme 2, where C—N or C—C coupling reactions give the compounds of the formula (2) according to the invention.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)-ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound and/or a further matrix material. Suitable emitting compounds and further matrix materials are indicated below in connection with the organic electroluminescent device. This further compound may also be polymeric.

The compounds according to the invention are suitable for use in an electronic device, in particular in an organic electroluminescent device.

The present invention therefore furthermore relates to the use of a compound according to the invention in an electronic device, in particular in an organic electroluminescent device.

The present invention still furthermore relates to an electronic device comprising at least one compound according to the invention.

An electronic device in the sense of the present invention is a device which comprises at least one layer which comprises at least one organic compound. The component may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised organic solar cells (DSSCs), organic optical detectors, organic photoreceptors, organic field-quench devices (O-FQDs), light-emitting electrochemical cells (LECs), organic laser diodes (O-lasers) and "organic plasmon emitting devices", but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). The organic electroluminescent device according to the invention may also be a tandem OLED, in particular also for white-emitting OLEDs.

The compound according to the invention in accordance with the embodiments indicated above can be employed in various layers, depending on the precise structure. Preference is given to an organic electroluminescent device comprising a compound of the formula (1) or the preferred embodiments indicated above as matrix material for phosphorescent in an emitting layer. The organic electroluminescent device here may comprise one emitting layer, or it may comprise a plurality of emitting layers, where at least one emitting layer comprises at least one compound according to the invention as matrix material.

If the compound according to the invention is employed as matrix material for a phosphorescent compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state >1, in particular from an excited triplet state. In the sense of this application, all luminescent complexes containing transition metals or lanthanides, in particular all iridium, platinum and copper complexes, are to be regarded as phosphorescent compounds.

The mixture of the compound according to the invention and the emitting compound comprises between 99 and 1% by weight, preferably between 98 and 10% by weight, particularly preferably between 97 and 60% by weight, in particular between 95 and 80% by weight, of the compound according to the invention, based on the entire mixture comprising emitter and matrix material. Correspondingly, the mixture comprises between 1 and 99% by weight, preferably between 2 and 90% by weight, particularly preferably between 3 and 40% by weight, in particular between 5 and 30% by weight, of the emitter, based on the entire mixture comprising emitter and matrix material.

A further preferred embodiment of the present invention is the use of the compound according to the invention as matrix material for a phosphorescent emitter in combination with a further matrix material. If the compound according to the invention is employed in combination with a further matrix material, its proportion is preferably 20 to 50% by weight, based on the entire mixture. Suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example in accordance with WO 2007/063754 or WO 2008/056746, indenocarbazole derivatives, for example in accordance with WO 2010/136109, WO 2011/000455, WO 2013/041176 or WO 2013/056776, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/35060877, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with WO 2011/042107, WO 2011/060867, WO 2011/088877 and WO 2012/143080, or triphenylene derivatives, for example in accordance with WO 2012/048781. A further phosphorescent emitter which emits at shorter wavelength than the actual emitter may likewise be present in the mixture as co-host, or a compound which does not participate in the charge transport to a significant extent, if at all, as described, for example, in WO 2010/108579.

Particularly suitable as co-matrix material in combination with the compound according to the invention are compounds which have a large band gap and do not themselves participate in the charge transport of the emitting layer, or at least only do so to an insignificant extent. Such materials are preferably pure hydrocarbons. Examples of such materials are found, for example, in WO 2009/124627 or in WO 2010/006680.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/044988, WO 2011/157339, WO 2012/007086, WO 2012/163471, WO 2013/000531 and WO 2013/020631, WO 2014/008982, WO 2014/023377. Furthermore suitable are, for example, the metal complexes disclosed in the unpublished applications EP 12008582.4, EP 13003484.6, EP 13003485.3, EP 13004552.9, EP 14000345.0 and EP 14000417.7. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

The compounds according to the invention are also suitable, in particular, as matrix materials for phosphorescent emitters in organic electroluminescent devices, as described, for example, in WO 98/24271, US 2011/0248247 and US 2012/0223633. In these multicoloured display components, an additional blue emission layer is applied by vapour deposition over the entire area to all pixels, also those having a colour other than blue. It has been found here, surprisingly, that the compounds according to the invention, when employed as matrix materials for the red and/or green pixels, continue to result in very good emission together with the vapour-deposited blue emission layer.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is the same as or similar to the metal complex in the emitting layer as hole-transport or hole-injection material directly adjacent to the emitting layer, as described, for example, in WO 2009/030981.

In the further layers of the organic electroluminescent device according to the invention, all materials can be used as are usually employed in accordance with the prior art. The person skilled in the art will therefore be able to employ all materials which are known for organic electroluminescent devices in combination with the compounds of the formula (1) according to the invention or the preferred embodiments indicated above without inventive step.

Preference is furthermore given to an organic electroluminescent device, characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished by one or more of the following surprising advantages over the prior art:
1. The compounds according to the invention, employed as matrix material for phosphorescent emitters, result in long lifetimes.
2. The compounds according to the invention result in high efficiencies. This applies, in particular, if the compounds are employed as matrix material for a phosphorescent emitter.
3. In the case of processing from solution, the compounds according to the invention have very good film-formation properties, characterised by good solubility and high glass transition temperatures.

These above-mentioned advantages are not accompanied by an impairment in the other electronic properties.

The invention is explained in greater detail by the following examples without wishing to restrict it thereby. The person skilled in the art will be able to use the descriptions to carry out the invention throughout the range disclosed and prepare further compounds according to the invention without inventive step and use them in electronic devices or apply the process according to the invention.

EXAMPLES

Synthesis Examples

The following syntheses are carried out, unless indicated otherwise, under a protective-gas atmosphere in dried solvents. The solvents and reagents can be purchased from ALDRICH or ABCR. The numbers indicated in the case of the starting materials which are not commercially available are the corresponding CAS numbers.

Example 1a: Synthesis of
N-(9,9-dimethylfluoren-2-yl)-4-aminobiphenyl

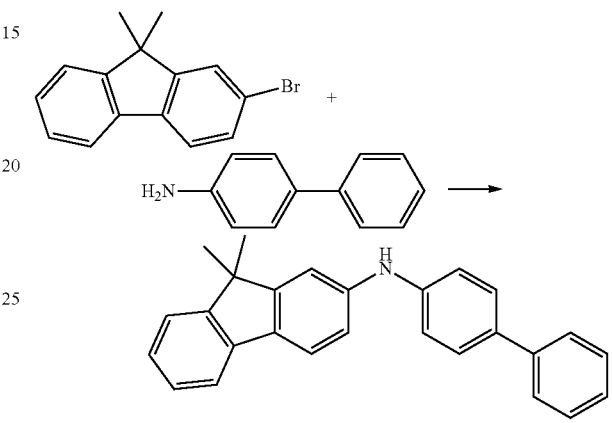

24.0 g (142 mmol) of 4-aminobiphenyl [92-67-1] and 32.0 g (117 mmol) of 2-bromo-9,9'-dimethylfluorene [28320-31-2] are initially introduced in 950 ml of toluene. The mixture is flushed with argon for 30 minutes with vigorous stirring. 1.0 g (1.8 mmol) of 1,1'-bis(diphenylphosphino)ferrocene [12150-46-8], 355 mg (1.6 mmol) of palladium(II) acetate and 28.8 g (300 mmol) of sodium tert-butoxide are added, and the reaction mixture is heated under reflux for 15 h. After cooling to room temperature, the reaction mixture is extended with 300 ml of toluene and 1200 ml of water. The organic phase is separated off, washed three times with 250 ml of water each time and dried over sodium sulfate. The solvent is removed in a rotary evaporator. 50 ml of ethyl acetate are added to the oil which remains, and the mixture is stirred slowly into 800 ml of a heptane/ethyl acetate mixture (20:1). The solid formed is filtered off with suction, washed twice with about 50 ml of heptane and dried in vacuo, leaving 29.2 g (80 mmol, 69% of theory) of the product having a purity of 99% according to HPLC.

The following compound can be prepared analogously:

| Ex. | Starting material | Product | Yield |
|---|---|---|---|
| 1b | ![Br-phenyl-dibenzofuran structure] [955959-84-9] | ![dibenzofuran-phenyl-NH-biphenyl product structure] | 74% |

Example 2a: Synthesis of N-(biphenyl-2-yl)-N-(biphenyl-4-yl)-4-(4,4,5,5-tetramethyl-1,3,2-dioxaborolan-2-yl)phenylamine

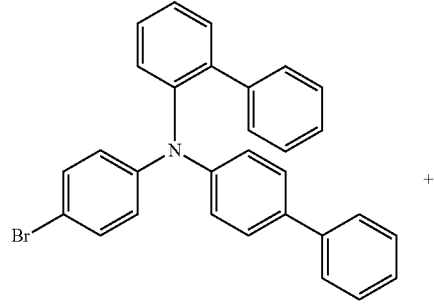

+

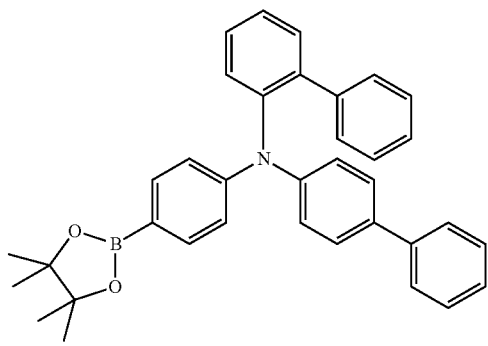

33.8 g (71 mmol) of N-(biphenyl-2-yl)-N-(biphenyl-4-yl)-N-(4-bromophenyl)-amine [1371651-92-1], 21.9 g (86 mmol) of bis(pinacolato)diborane [73183-34-3], 21.7 g (221 mmol) of potassium acetate and 1.7 g (2.1 mmol) of 1,1'-bis(diphenylphosphino)ferrocenepalladium(II) dichloride/dichloromethane adduct [95464-26-4] are heated under reflux in 1000 ml of anhydrous dioxane for 16 h. After cooling to room temperature, the organic phase is extended with 750 ml of ethyl acetate, washed three times with 300 ml of water each time and dried over sodium sulfate. The solvent is removed in a rotary evaporator, and the residue is recrystallised twice from heptane, leaving 22.6 g (43 mmol, 61% of theory) of the product as a pale-yellow solid having a purity of about 99% according to $^1$H-NMR.

Example 3a: Synthesis of 2-(biphenyl-3-yl)-4-chloro-6-phenyl-1,3,5-triazine

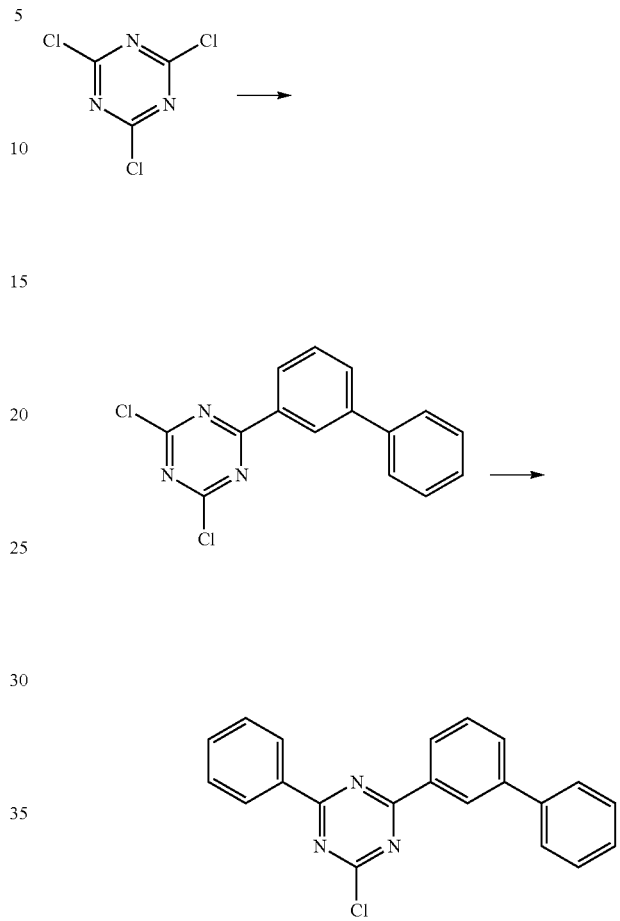

11.6 g (477 mmol) of magnesium are activated using a grain of iodine. 30 ml of a solution of 100 g (429 mmol) of 3-bromobiphenyl [2113-57-7] in 800 ml of THF are added; the reaction is initiated using a hair dryer. After commencement of the reaction, the remaining solution is added dropwise at such a rate that the reflux is maintained by the heat of reaction. When the addition is complete, the reaction mixture is heated under reflux for a further 2 h.

79.1 g (429 mmol) of 2,4,6-trichloro-1,3,5-triazine are initially introduced in 500 ml of THF and cooled to −5° C. The above Grignard solution is added dropwise at such a rate that the internal temperature does not exceed 0° C. The cooling is removed, and the mixture is stirred for 16 h and subsequently re-cooled to −5° C., and 219 ml (438 mmol) of phenylmagnesium chloride solution (2M in THF) are added dropwise at such a rate that the internal temperature does not exceed 0° C. The cooling is removed, and the mixture is stirred for 18 h. 450 ml of 1M hydrochloric acid are slowly stirred in. After 1 h, the solid formed is filtered off with suction and dried in vacuo. Recrystallisation twice from toluene leaves 52.9 g (154 mmol, 36% of theory) of the product as a pale-brown solid having a purity of about 98% according to $^1$H-NMR.

The following compounds can be prepared analogously:

| Ex. | Starting material Step 1 | Product | Yield |
|---|---|---|---|
| 3b | [1233200-57-1] | | 31% |
| 3c | [103068-20-8] | | 37% |

Example 4a: Synthesis of 10-(3-bromophenyl)-12,12-dimethyl-10,12-dihydro-10-azaindeno[2,1-b]fluorine

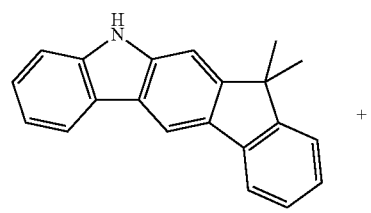

150.0 g (526 mmol) of 12,12-dimethyl-10,12-dihydro-10-azaindeno[2,1-b]-fluorene [1257220-47-5], 184.0 g (1.05 mol) of 1-bromo-3-fluorobenzene [1073-06-9] and 334.7 g (1.58 mol) of potassium phosphate are initially introduced in 2 l of dimethylacetamide and heated under reflux for 14 h. After cooling to room temperature, the solvent is removed as far as possible in a rotary evaporator, leaving a dark-brown oil. After vigorous rubbing of the flask wall with a glass rod, the product can be precipitated by slowly stirring in 750 ml of ethanol. The solid formed is filtered off with suction, washed four times with 250 ml of ethanol each time, dried in vacuo and finally sublimed at a pressure of about $10^{-5}$ mbar and 220° C., leaving 152.2 g (347 mmol, 66% of theory) of the product as yellow glass-like solid having a purity of about 99% according to $^1$H-NMR.

Example 5a: Synthesis of (2-chlorophenyl)-(spiro-9,9'-bifluoren-4-yl)-amine

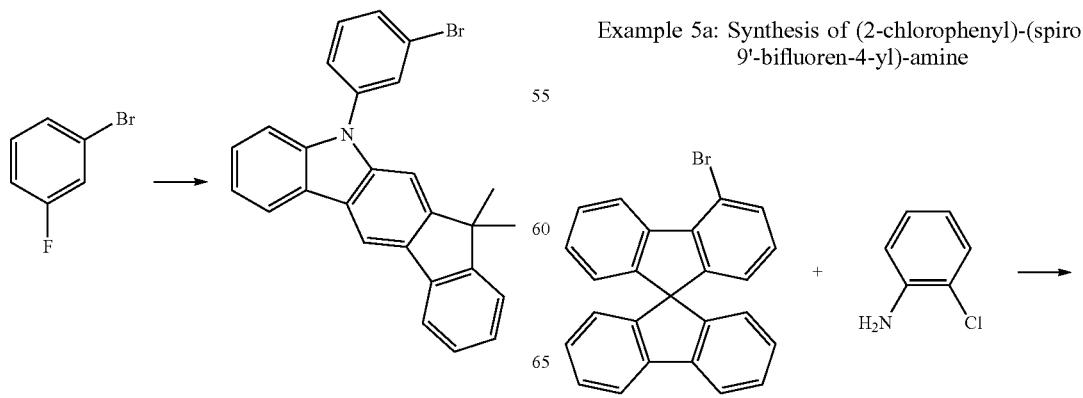

-continued

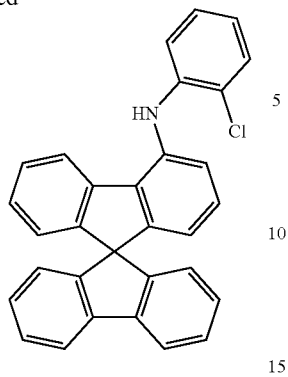

54.1 g (137 mmol) of 4-bromospiro-9,9'-bifluorene [1161009-88-6], 17.9 g (140 mmol) of 2-chloroaniline [95-51-2], 68.2 g (710 mmol) of sodium tortbutoxide, 613 mg (2.7 mmol) of palladium(II) acetate and 3.03 g (5.5 mmol) of 1,1'-bis(diphenylphosphino)ferrocene are initially introduced in 1300 ml of toluene and heated under reflux for 5 h. After cooling to room temperature, the reaction mixture is extended with 700 ml of toluene and filtered through Celite. The solvent is removed in a rotary evaporator, and the residue is recrystallised from a toluene/heptane mixture (1:2). Drying in vacuo leaves 52.2 g (118 mmol, 86% of theory) of the product as pale-yellow solid.

The following compound can be prepared analogously:

| Ex. | Starting material | Product | Yield |
|---|---|---|---|
| 5b | | | 72% |

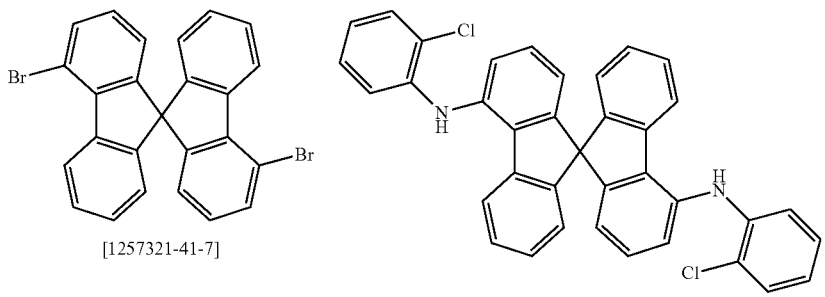

[1257321-41-7]

Example 6a: 1-(2-Chlorophenylamine)fluoren-9-one

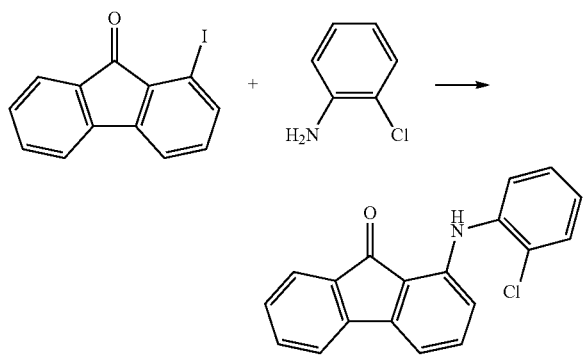

52 g (166 mmol) of 1-iodofluoren-9-one [52086-21-2], 19.0 ml (171 mmol) of 2-chloroaniline [95-51-2], 59.8 g (432 mmol) of potassium carbonate, 3.85 g (6.6 mmol) of 1,1'-(9,9-dimethyl-9H-xanthene-4,5-diyl)bis(1,1-diphenyl) phosphine [161265-03-8] and 746 mg (3.3 mmol) of palladium(II) acetate are initially introduced in 400 ml of toluene and heated under reflux for 15 h. After cooling to room temperature, the mixture is extended with 200 ml of toluene and 500 ml of water, and the organic phase is separated off, washed twice with 200 ml of 3M hydrochloric acid each time and twice with 200 ml of water each time and filtered through a thin layer of aluminium oxide (basic, activity grade 1). The solvent is removed in a rotary evaporator. Drying in vacuo leaves 48.0 g (157 mmol, 95% of theory) of the product as orange solid having a purity of about 97% according to $^1$H-NMR.

Example 7a: Synthesis of spiro[9H-fluorene-9,7' (1'H)-indeno[1,2-a]-carbazole]

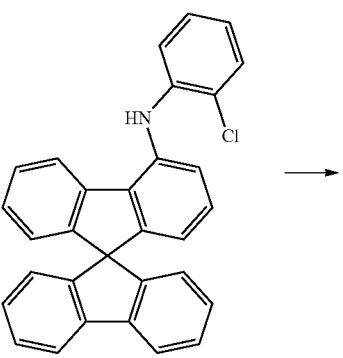

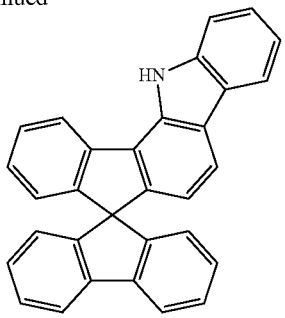

45.0 g (102 mmol) of (2-chlorophenyl)-(spiro-9,9'-bifluoren-4-yl)amine (from Ex. 5a), 56.0 g (405 mmol) of potassium carbonate, 4.5 g (12 mmol) of tricyclohexylphosphonium tetrafluoroborate and 1.38 g (6 mmol) of palladium(II) acetate are suspended in 500 ml of dimethylacetamide and heated under reflux for 6 h. After cooling to room temperature, the reaction mixture is extended with 600 ml of dichloromethane and 300 ml of water and stirred for 30 minutes. The organic phase is separated off and freed from solvent in a rotary evaporator. The residue is extracted with 250 ml of hot toluene via a bed of aluminium oxide (basic, activity grade 1) and finally recrystallised once from toluene, leaving 32.5 g (80 mmol, 78% of theory) of the product as beige solid having a purity of about 98% according to $^1$H-NMR.

The following compounds can be prepared analogously:

| Ex. | Starting material | Product | Yield |
|---|---|---|---|
| 7b | | | 68% |
| 7c | | | 87% |

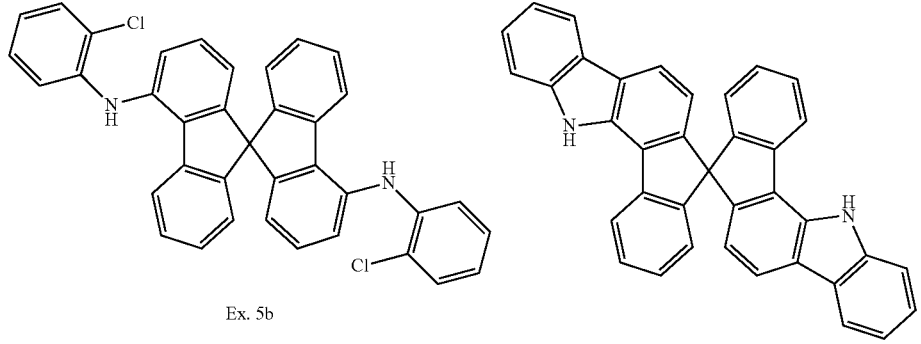

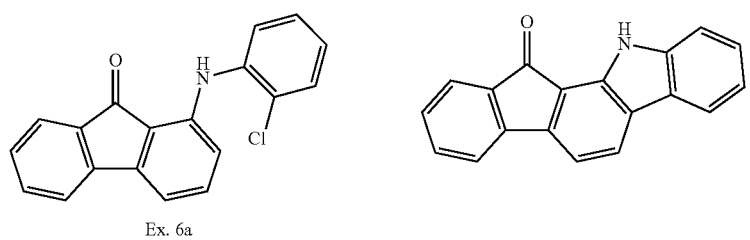

Example 8a: Synthesis of N-phenylspiro[9H-fluorene-9,7'(1'H)-indeno[1,2-a]carbazole]

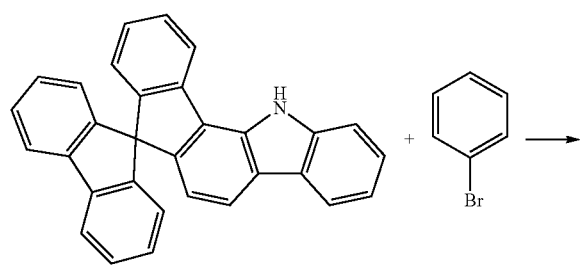

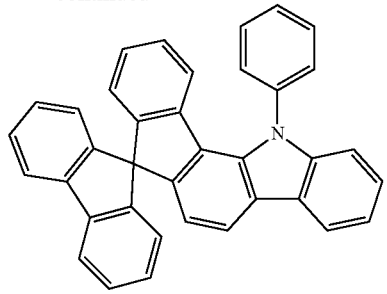

43.0 g (106 mmol) of spiro[9H-fluorene-9,7'(1'H)-indeno[1,2-a]carbazole] (from Ex. 7a), 17.9 g (114 mmol) of bromobenzene, 30.5 g (317 mmol) of sodium tert-butoxide, 0.5 g (2.2 mmol) of palladium(II) acetate and 4.2 ml of tri-tert-butylphosphine solution (1M in toluene) are initially introduced in 1500 ml of p-xylene and heated under reflux for 16 h. After cooling to room temperature, the organic phase is separated off from solid constituents, washed three times with 200 ml of water each time and subsequently freed from solvent in a rotary evaporator. The residue is extracted with about 300 ml of hot toluene via aluminium oxide (basic, activity grade 1) and finally recrystallised twice from toluene, leaving 37.6 g (78 mmol, 74% of theory) of the product as pale-yellow solid having a purity of about 99% according to $^1$H-NMR.

The following compounds can be prepared analogously:

| Ex. | Starting material 1 | Starting material 2 |
|---|---|---|
| 8b | [1257220-47-5] | [108-86-1] |
| 8c | [86-74-8] | [1233200-57-1] |

-continued
8d
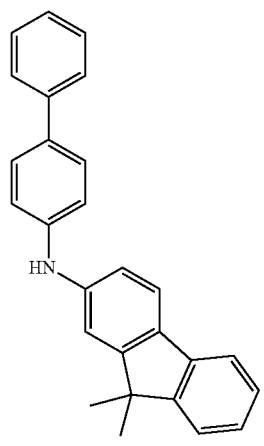
Ex. 1a
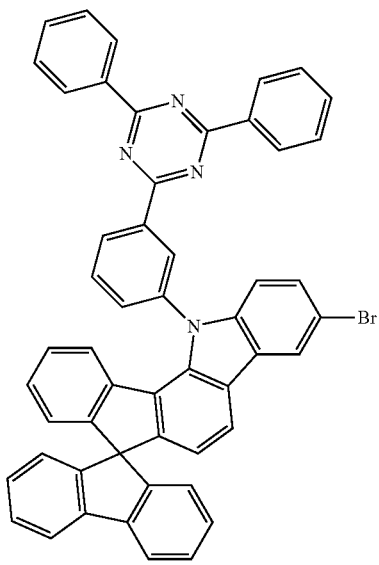
Ex. 10f
8e
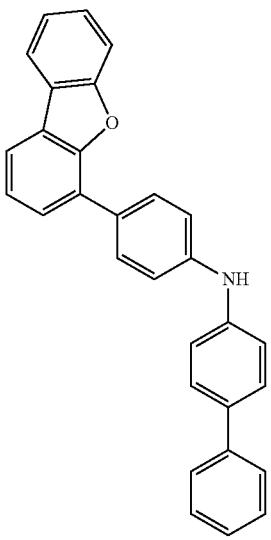
Ex. 1b
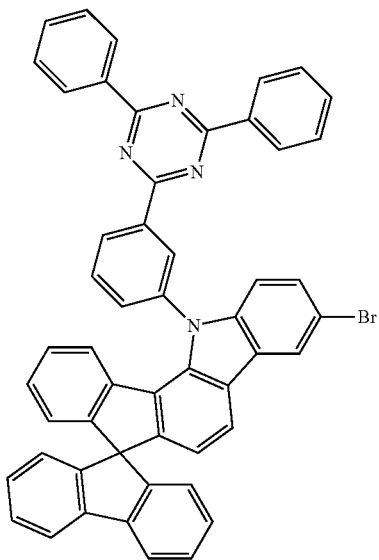
Ex. 10f
8f
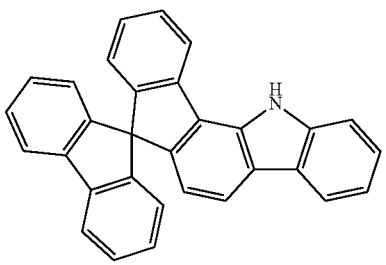
Ex. 7a
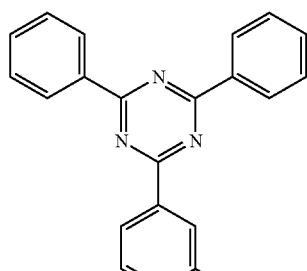
[864377-31-1]

| | | |
|---|---|---|
| 8g | 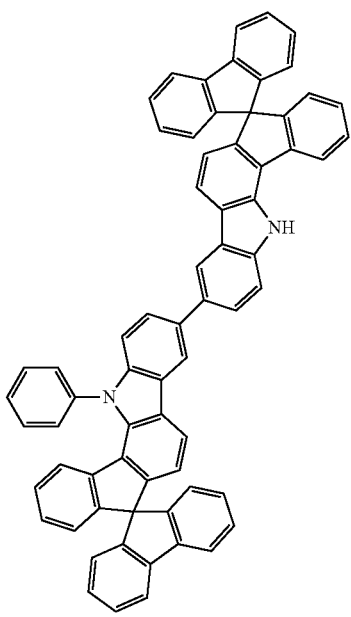<br>Ex. 12d | 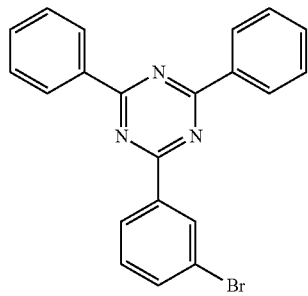<br>[864377-31-1] |
| 8h | | 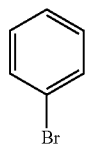<br>[108-86-1] |
| | 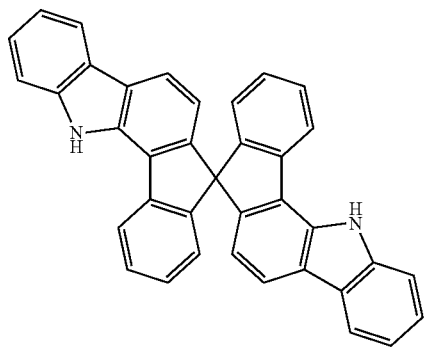 [SMILES: c1ccc2c(c1)-c1c(ccc3c1[nH]c1ccccc13)C21c2ccccc2-c2c1ccc1c2[nH]c2ccccc21]<br>Ex. 7b | |
| 8i | 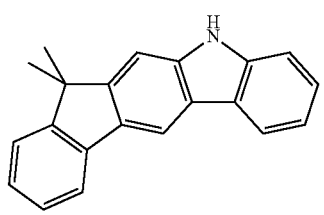<br>[1257220-47-5] | 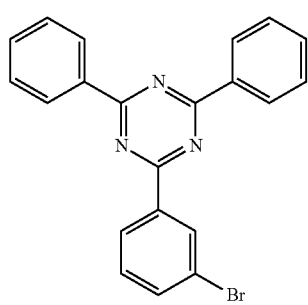<br>[864377-31-1] |

-continued
8j 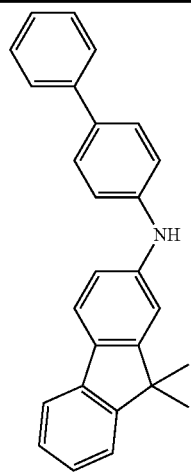
Ex. 1a
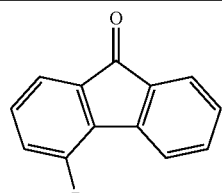
[4269-17-4]
8k 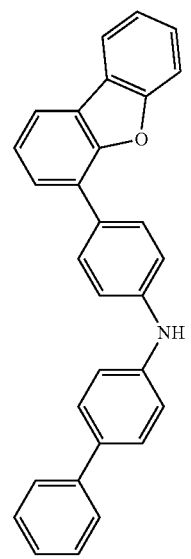
Ex. 1b
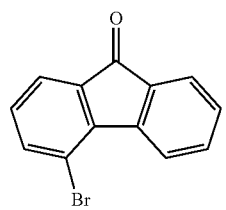
[4269-17-4]
| Ex. | Product | Yield |
|---|---|---|
| 8b | 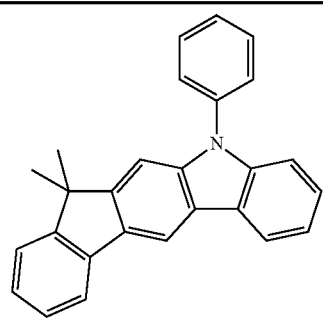 | 83% |

-continued
| | | |
|---|---|---|
| 8c | 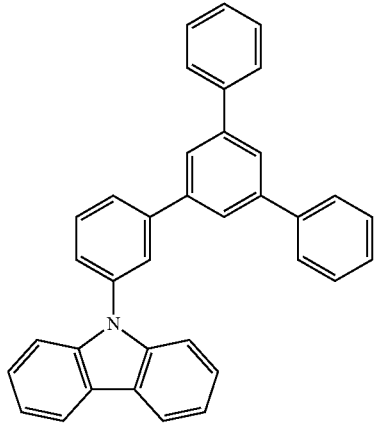 [SMILES: c1ccc(-c2cc(-c3ccccc3)cc(-c3cccc(-n4c5ccccc5c5ccccc54)c3)c2)cc1] | 77% |
| 8d | 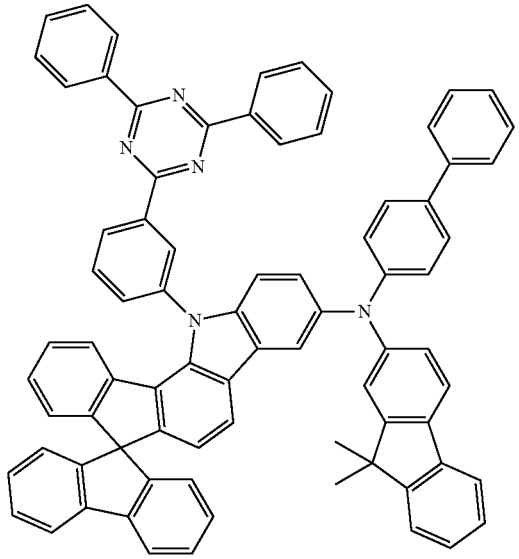 [SMILES: CC1(C)c2ccccc2-c2ccc(N(c3ccc(-c4ccccc4)cc3)c3ccc4c(c3)c3ccc5c(c3n4-c3cccc(-c4nc(-c6ccccc6)nc(-c6ccccc6)n4)c3)-c3ccccc3C53c4ccccc4-c4ccccc43)cc21] | 51% |
| 8e | 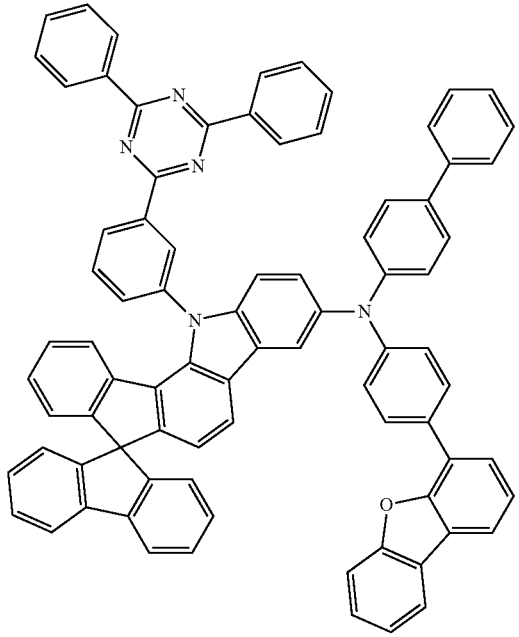 [SMILES: c1ccc(-c2ccc(N(c3ccc(-c4cccc5c4oc4ccccc45)cc3)c3ccc4c(c3)c3ccc5c(c3n4-c3cccc(-c4nc(-c6ccccc6)nc(-c6ccccc6)n4)c3)-c3ccccc3C53c4ccccc4-c4ccccc43)cc2)cc1] | 54% |

-continued
| | | |
|---|---|---|
| 8f | 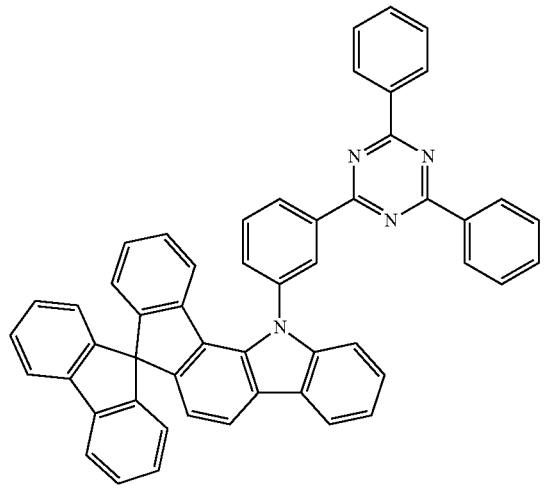 [SMILES: c1ccc(-c2nc(-c3ccccc3)nc(-c3cccc(-n4c5ccccc5c5ccc6c(c54)-c4ccccc4C64c5ccccc5-c5ccccc54)c3)n2)cc1] | 53% |
| 8g | 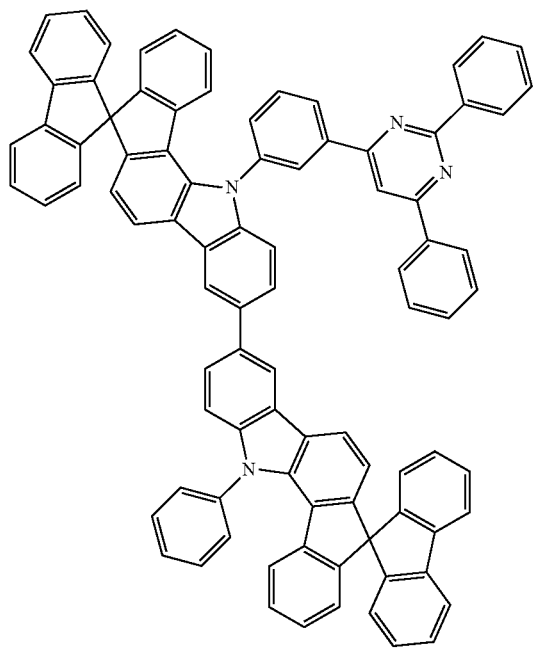 [SMILES: c1ccc(-c2cc(-c3cccc(-n4c5ccc(-c6ccc7c(c6)c6ccc8c(c6n7-c6ccccc6)-c6ccccc6C86c7ccccc7-c7ccccc76)cc5c5ccc6c(c54)-c4ccccc4C64c5ccccc5-c5ccccc54)c3)nc(-c3ccccc3)n2)cc1] | 61% |
| 8h | 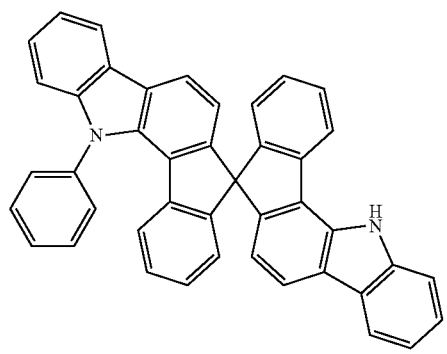 [SMILES: c1ccc(-n2c3ccccc3c3ccc4c(c32)-c2ccccc2C42c3ccccc3-c3c2ccc2c3[nH]c3ccccc32)cc1] | 82% |

| | | |
|---|---|---|
| 8i | 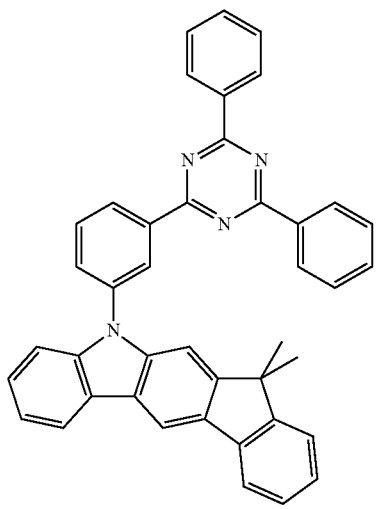 [SMILES: CC1(C)c2ccccc2-c2cc3c4ccccc4n(-c4cccc(-c5nc(-c6ccccc6)nc(-c6ccccc6)n5)c4)c3cc21] | 58% |
| 8j | 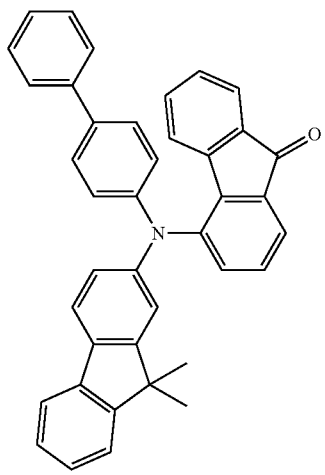 [SMILES: CC1(C)c2ccccc2-c2ccc(N(c3ccc(-c4ccccc4)cc3)c3cccc4c3-c3ccccc3C4=O)cc21] | 77% |
| 8k | 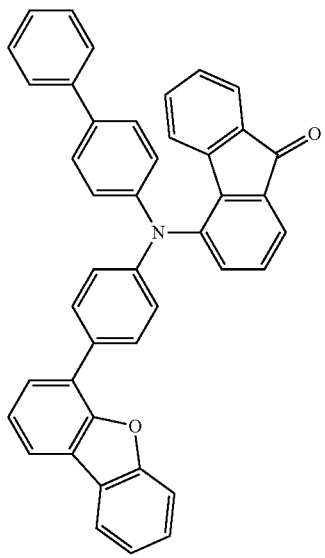 [SMILES: O=C1c2ccccc2-c2c1cccc2N(c1ccc(-c2ccccc2)cc1)c1ccc(-c2cccc3c2oc2ccccc23)cc1] | 67% |

Example 9a: Synthesis of N-(4'-bromospiro-9,9'bifluoren-4-yl)-N-(9,9'-dimethylfluoren-2-yl)-4-aminobiphenyl

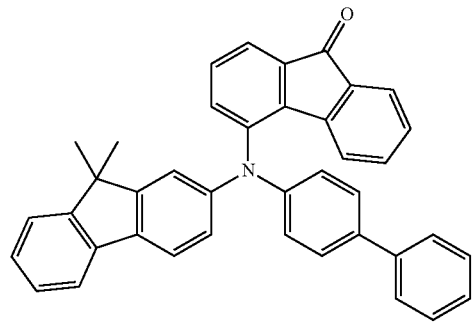

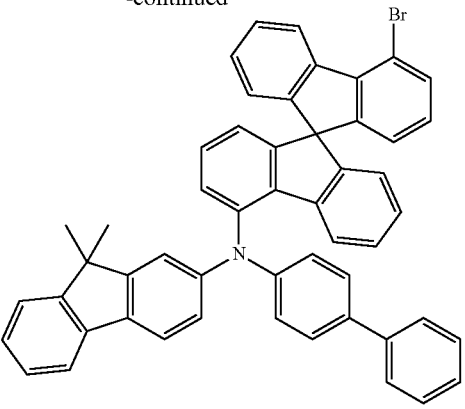

24.6 g (79 mmol) of 2,2'-dibromobiphenyl [13029-09-9] in 200 ml of THF are cooled to −78° C. 32 ml of n-butyl-lithium (2.5M in hexane) are added dropwise at such a rate that the internal temperature does not exceed −70° C. The reaction mixture is stirred for 2 h. A suspension of 26.9 g (50 mmol) of N-(9,9-dimethylfluoren-2-yl)-N-(fluorenon-4-yl)-4-aminobiphenyl (from Ex. 8j) is then added at such a rate that the internal temperature does not exceed −70° C. The cooling is removed, and the mixture is stirred for a further 14 h. After addition of 100 ml of water, the mixture is stirred for 15 minutes, and the organic phase is separated off and freed from solvent in a rotary evaporator. The residue is suspended in 500 ml of glacial acetic acid, 0.5 ml of concentrated sulfuric acid is added, and the mixture is stirred at 100° C. for 2 h. After cooling to room temperature, the solid formed is filtered off with suction, washed with 100 ml of glacial acetic acid and washed three times with 100 ml of ethanol each time and finally recrystallised from dioxane. Drying in vacuo leaves 25.5 g (34 mmol, 68% of theory) of the product as pale-red solid having a purity of about 98% according to $^1$H-NMR.

The following compounds can be prepared analogously:

| Ex. | Starting material | Product | Yield |
|---|---|---|---|
| 9b | | | 69% |

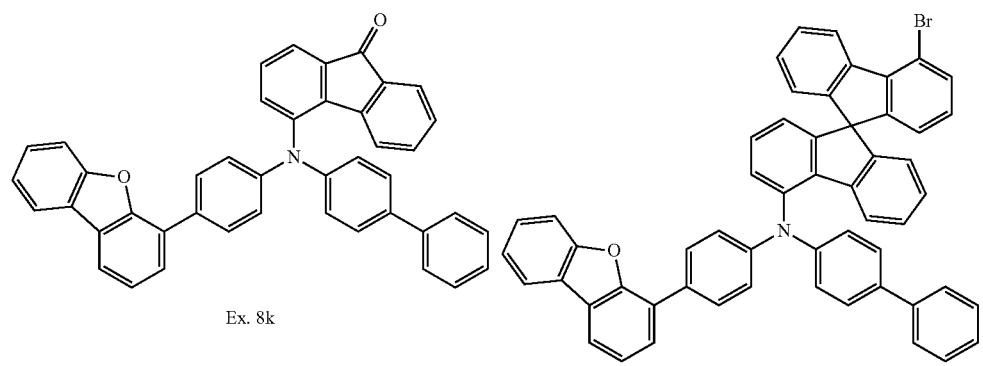

Ex. 8k

-continued
| Ex. | Starting material | Product | Yield |
|---|---|---|---|
| 9c | | | 83% |
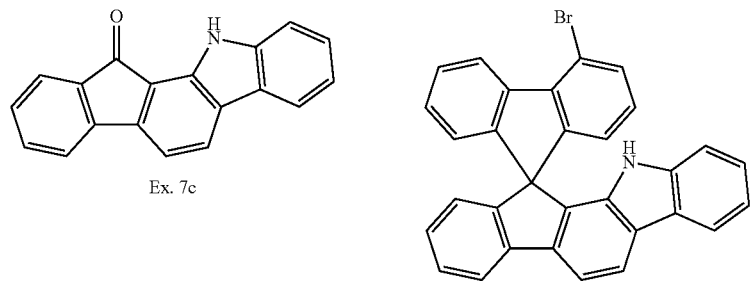
Ex. 7c
20
The following compounds can be prepared analogously by lithiation of 2-bromobiphenyl [2052-07-5] in the first step:
| Ex. | Starting material | Product | Yield |
|---|---|---|---|
| 9d | | | 74% |
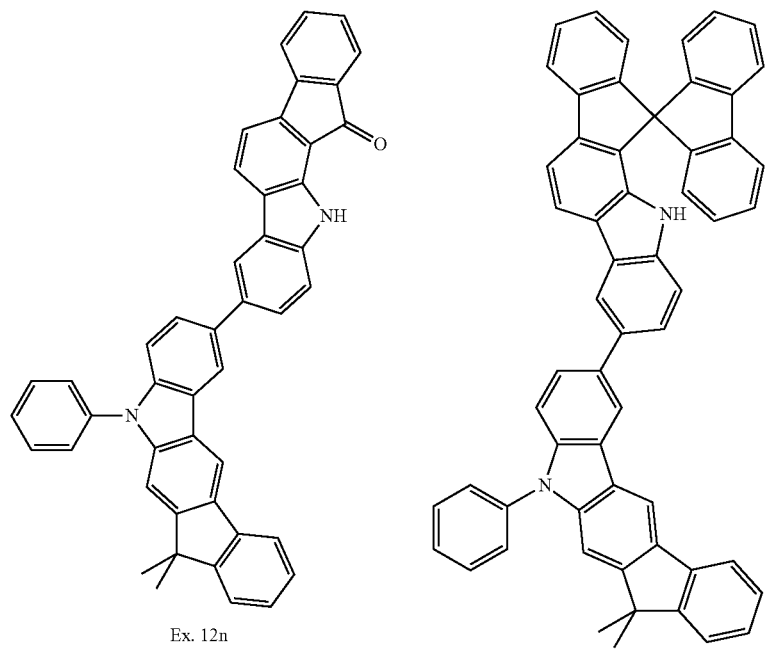
Ex. 12n

| Ex. | Starting material | Product | Yield |
|---|---|---|---|
| 9e | | | 70% |

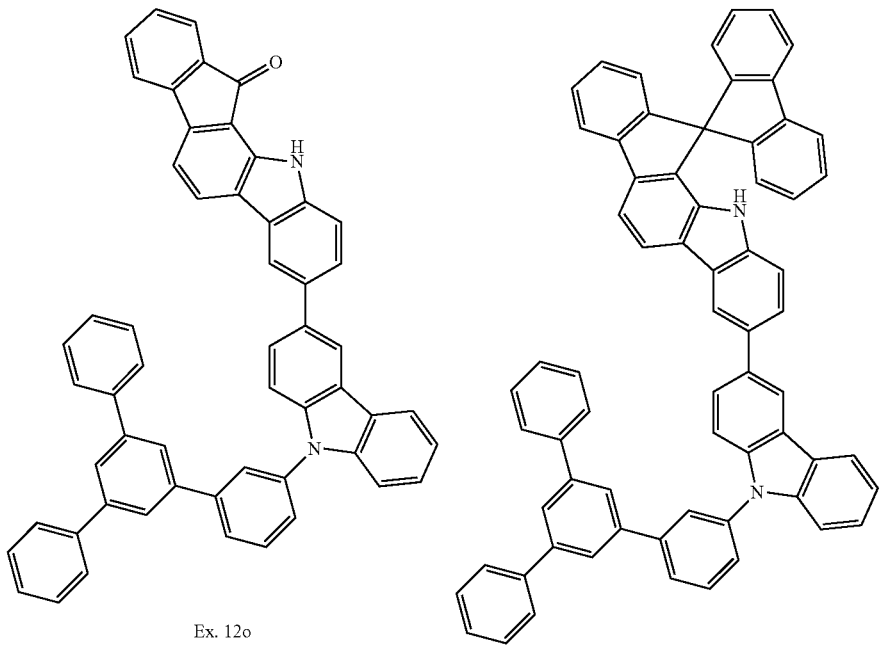

Ex. 12o

Example 10a: Synthesis of N-phenylspiro[9H-fluorene-6'-bromo-9,7'(1'H-indeno[1,2-a]carbazole]

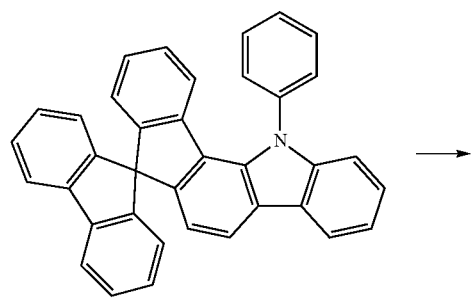

→

-continued

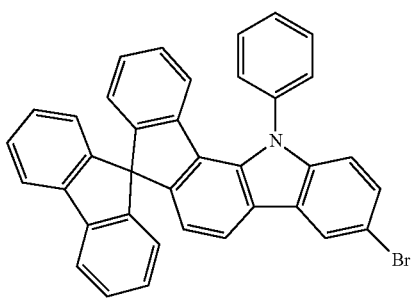

85.2 g (177 mmol) of N-phenylspiro[9H-fluorene-9,7' (1'H)-indeno[1,2-a]-carbazole] (from Ex. 8a) are initially introduced in 1500 ml of THF. The reaction mixture is cooled to 0° C., and 31.5 g (177 mmol) of N-bromosuccinimide are added in portions over the course of 30 minutes. The cooling is removed, and the mixture is stirred for 14 h and subsequently concentrated to about 250 ml. 1000 ml of water are added with vigorous stirring, and the solid formed is filtered off with suction and washed by boiling twice with 800 ml of ethanol each time. Drying in vacuo leaves 87.1 g (155 mmol, 88% of theory) of the product as colourless solid having a purity of about 98% according to ¹H-NMR.

The following compounds can be prepared analogously:

| Ex. | Starting material | Product | Yield |
|---|---|---|---|
| 10b | Ex. 7a | | 60% |
| 10c | [1257220-47-5] | | 65% |
| 10d | Ex. 8b | | 81% |
| 10e | Ex. 8c | | 81% |

-continued

| Ex. | Starting material | Product | Yield |
|---|---|---|---|
| 10f | Ex. 8f | | 49% |
| 10g | Ex. 7b | | 52% |
| 10h | Ex. 7b | | 61% |

-continued

| Ex. | Starting material | Product | Yield |
|---|---|---|---|
| 10i | Ex. 8h | | 12% after column chromatography |
| 10j | Ex. 8i | | 68% |

| Ex. | Starting material | Product | Yield |
|---|---|---|---|
| 10k | Ex. 7c | | 90% |
| 10l | Ex. 12p | | 51% |

Example 11a: Synthesis of N-phenylspiro[9H-fluorene-6'-(4,4,5,5-tetramethyl-1,3,2-dioxaborolan-2-yl)-9,7'(1'H)-indeno[1,2-a]carbazole]

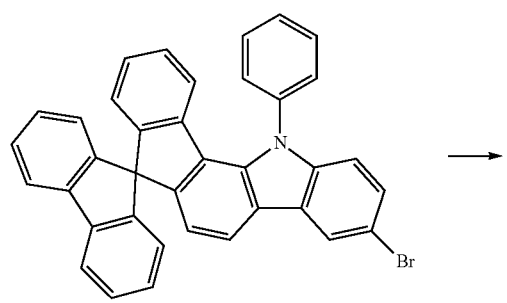

→

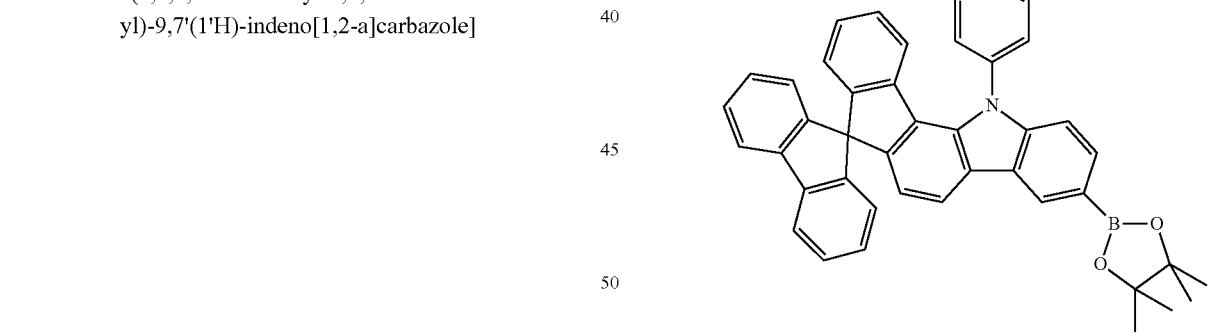

46.0 g (82 mmol) of N-phenylspiro[9H-fluorene-6'-bromo-9,7'(1'H)-indeno-[1,2-a]carbazole] (Ex. 10a), 21.9 g (86 mmol) of bis(pinacolato)diborane, 64.4 g (656 mmol) of potassium acetate and 2.0 g (2.4 mmol) of 1,1'-bis-(diphenylphosphino)ferrocenepalladium(II) dichloride/dichloromethane adduct [95464-26-4] in 1000 ml of dioxane are heated at an internal temperature of 80° C. for 22 h. After cooling to room temperature, the solvent is removed in a rotary evaporator, 700 ml of dichloromethane and 1000 ml of water are added to the residue, and the mixture is stirred for 30 minutes. The organic phase is separated off, washed twice with 250 ml of water each time, dried over sodium sulfate and concentrated to about 100 ml. 1000 ml of heptane are stirred in, and the solid formed is filtered off with suction. Drying in vacuo leaves 43.7 g (72 mmol, 88% of theory) of the product as pale-brown solid having a purity of about 96% according to $^1$H-NMR.
The following compounds can be prepared analogously:
| Ex. | Starting material | Product | Yield |
|---|---|---|---|
| 11b | 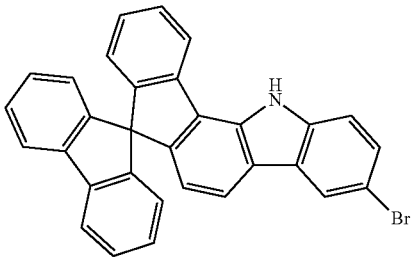 [SMILES: Brc1ccc2[nH]c3c4c(ccc3c2c1)C1(c2ccccc2-c2ccccc21)c1ccccc1-4]<br>Ex. 10b | 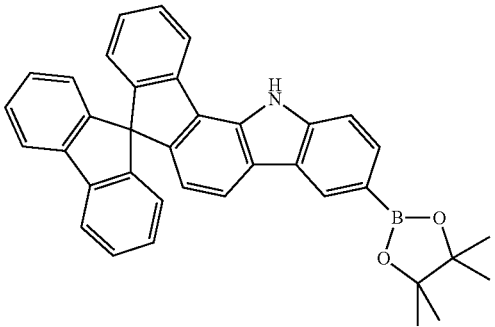 | 81% |
| 11c | 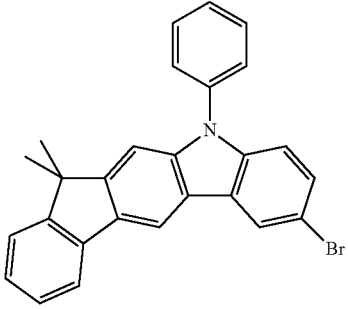 [SMILES: CC1(C)c2ccccc2-c2cc3c4cc(Br)ccc4n(-c4ccccc4)c3cc21]<br>Ex. 10d | 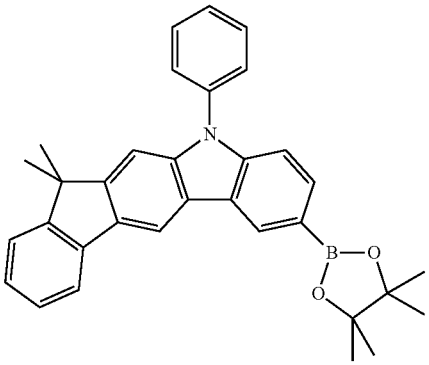 [SMILES: CC1(C)c2ccccc2-c2cc3c4cc(B5OC(C)(C)C(C)(C)O5)ccc4n(-c4ccccc4)c3cc21] | 89% |
| 11d | 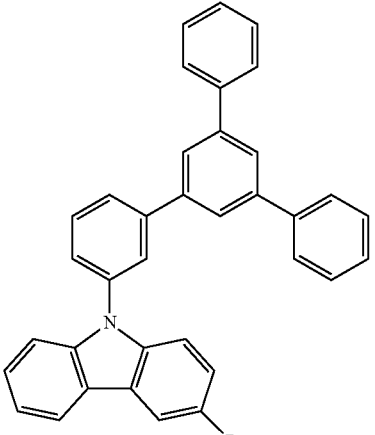<br>Ex. 10e | 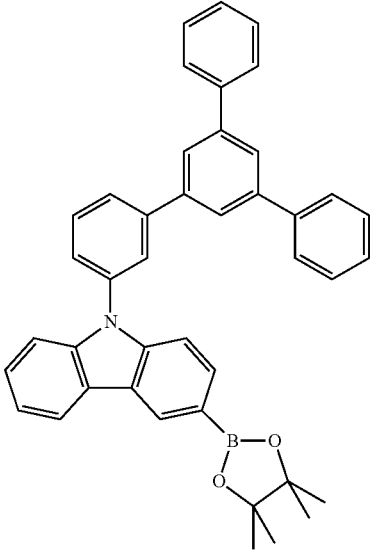 [SMILES: CC1(C)OB(c2ccc3c(c2)c2ccccc2n3-c2cccc(-c3cc(-c4ccccc4)cc(-c4ccccc4)c3)c2)OC1(C)C] | 82% |

| Ex. | Starting material | Product | Yield |
|---|---|---|---|
| 11e | Ex. 10f | | 78% |
| 11f | Ex. 4a | | 63% |
| 11g | Ex. 10k | | 61% |
Example 12a: Synthesis of spiro[9H-fluorene-6'-(N-phenylcarbazol-3-yl)-9,7'(1'H)-indeno[1,2-a]carbazole]
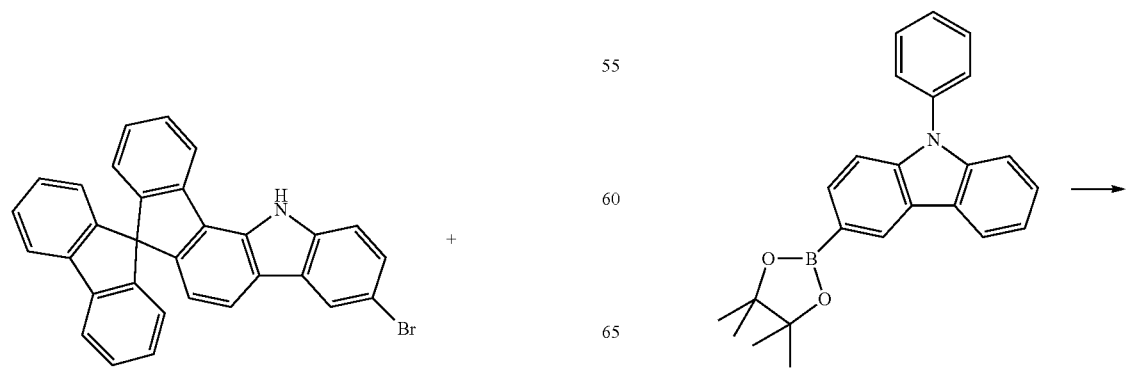

-continued

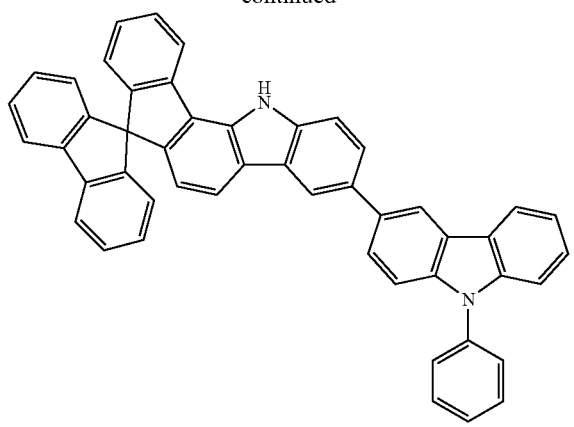

31.0 g (64 mmol) of spiro[9H-fluorene-6'-bromo-9,7'(1'H)-indeno[1,2-a]carbazole] (from Ex. 10b) and 28.4 g (76 mmol) of N-phenyl-3-(4,4,5,5-tetramethyl-1,3,2-dioxaborolan-2-yl)carbazole [1126522-69-7] are initially introduced in a mixture of 250 ml of toluene, 125 ml of dioxane and 60 ml of water and flushed with argon for 30 minutes. After addition of 32.4 g (141 mmol) of tripotassium phosphate monohydrate [27176-10-9], 359 mg (1.6 mmol) of palladium(II) acetate and 974 mg (3.2 mmol) of trio-tolyl-phosphine, the reaction mixture is heated under reflux for 18 h. After cooling to room temperature, the mixture is extended with 500 ml of water. The organic phase is separated off, washed twice with 250 ml of water each time and freed from solvent in a rotary evaporator. The residue is slurried with 150 ml of heptane, and the solid formed is filtered off with suction. The latter is extracted with about 250 ml of hot cyclohexane via aluminium oxide (basic, activity grade 1); if necessary, the extraction solution is reduced by about one third. The solid formed is filtered off with suction and dried in vacuo, leaving 21.7 g (34 mmol, 53% of theory) of the product as beige solid having a purity of about 99% according to $^1$H-NMR.

The following compounds can be prepared analogously:

| Ex. | Starting material | Product | Yield |
|---|---|---|---|
| 12b | Ex. 11d | | 56% |
| 12c | Ex. 11c | | 55% |

-continued
| Ex. | Starting material | Product | Yield |
|---|---|---|---|
| 12d | 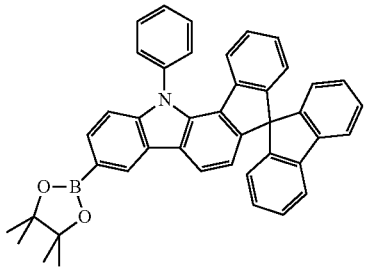<br>Ex. 11a | 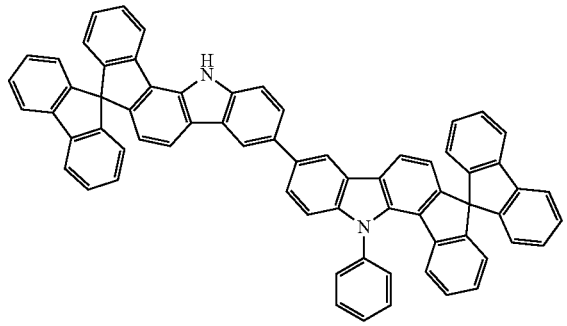 [SMILES: c1ccc(-n2c3ccc(-c4ccc5[nH]c6c7c(ccc6c5c4)C4(c5ccccc5-c5ccccc54)c4ccccc4-7)cc3c3ccc4c(c32)-c2ccccc2C42c3ccccc3-c3ccccc32)cc1] | 32% |
| 12e | 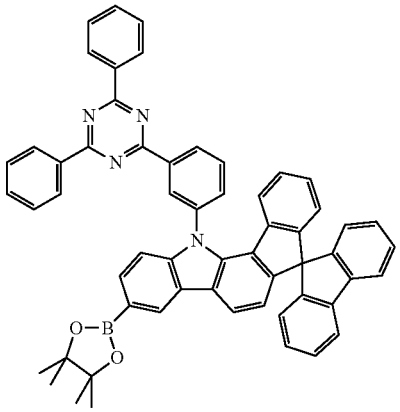<br>Ex. 11e | 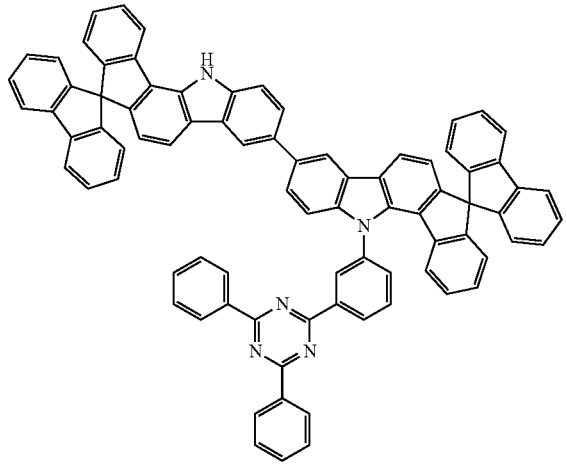 [SMILES: c1ccc(-c2nc(-c3ccccc3)nc(-c3cccc(-n4c5ccc(-c6ccc7[nH]c8c9c(ccc8c7c6)C6(c7ccccc7-c7ccccc76)c6ccccc6-9)cc5c5ccc6c(c54)-c4ccccc4C64c5ccccc5-c5ccccc54)c3)n2)cc1] | 47% |
| 12f | 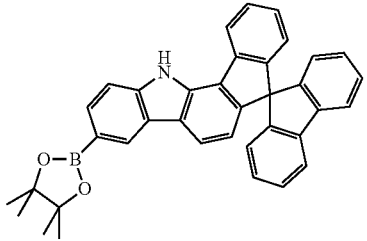<br>Ex. 11b | 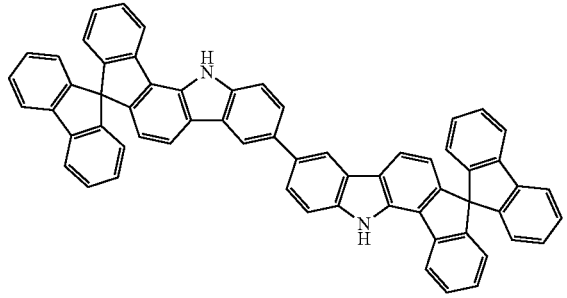 [SMILES: c1ccc2c(c1)-c1ccccc1C21c2ccccc2-c2c1ccc1c2[nH]c2ccc(-c3ccc4[nH]c5c6c(ccc5c4c3)C3(c4ccccc4-c4ccccc43)c3ccccc3-6)cc21] | 36% |
| 12g | 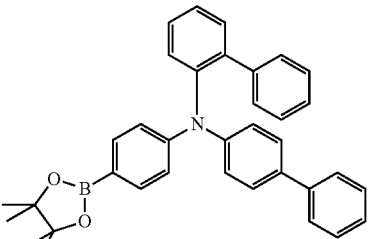<br>Ex. 2a | 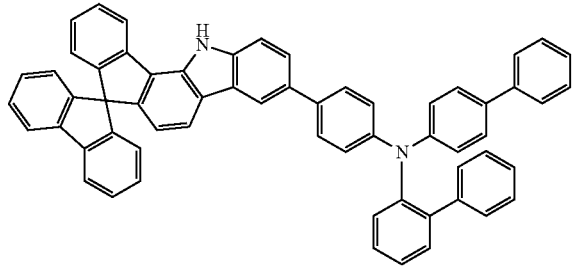 [SMILES: c1ccc(-c2ccc(N(c3ccc(-c4ccc5[nH]c6c7c(ccc6c5c4)C4(c5ccccc5-c5ccccc54)c4ccccc4-7)cc3)c3ccccc3-c3ccccc3)cc2)cc1] | 75% |

The following compounds can be prepared analogously by reaction of corresponding bromides with 12,12-dimethyl-10-phenyl-7-(4,4,5,5-tetramethyl-1,3,2-dioxaborolan-2-yl)-10,12-dihydro-10-azaindeno[2,1-b]fluorene (Ex. 11c):

| Ex. | Starting material | Product | Yield |
|---|---|---|---|
| 12h | Ex. 10g | | 50% |
| 12i | Ex. 10i | | 52% |

| Ex. | Starting material | Product | Yield |
|---|---|---|---|
| 12j | Ex. 10h | | 28% |

The following compounds can be prepared analogously by reaction of corresponding bromides with N-phenyl-3-(4,4,5,5-tetramethyl-1,3,2-dioxaborolan-2-yl)carbazole [1126522-69-7]:

| Ex. | Starting material | Product | Yield |
|---|---|---|---|
| 12k | Ex. 10j | | 69% |

-continued
| Ex. | Starting material | Product | Yield |
|---|---|---|---|
| 12l | 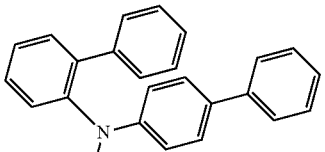<br>Ex. 101 | 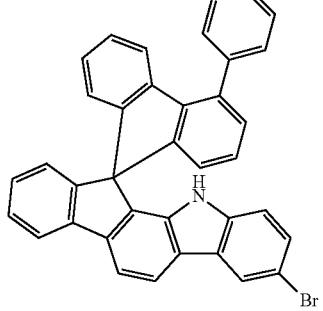 | 55% |
The following compounds can be prepared analogously:
| Ex. | Starting material 1 | Starting material 2 | Product | Yield |
|---|---|---|---|---|
| 12m | | | | 36% |
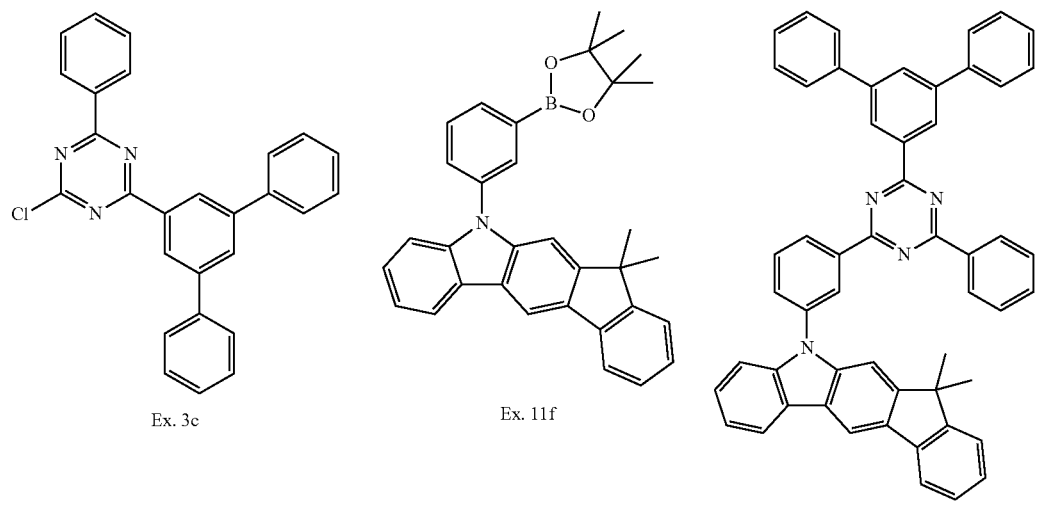
Ex. 3c     Ex. 11f -continued
| Ex. | Starting material 1 | Starting material 2 | Product | Yield |
|---|---|---|---|---|
| 12n | 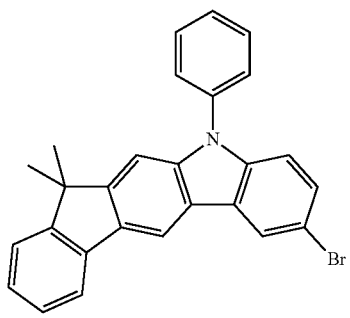<br>Ex. 10d | 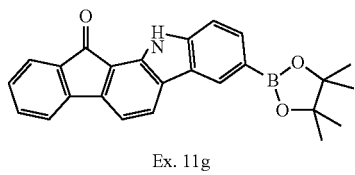 [SMILES: CC1(C)OB(c2ccc3[nH]c4c5c(ccc4c3c2)-c2ccccc2C5=O)OC1(C)C]<br>Ex. 11g | 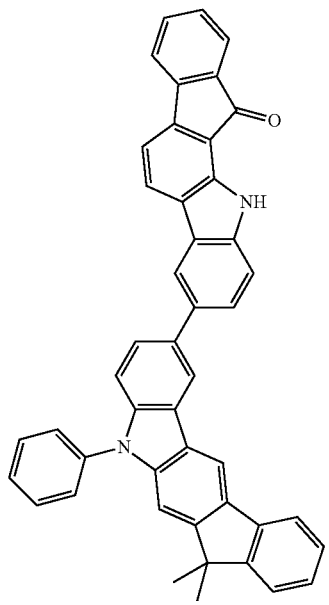 [SMILES: CC1(C)c2ccccc2-c2cc3c4cc(-c5ccc6[nH]c7c8c(ccc7c6c5)-c5ccccc5C8=O)ccc4n(-c4ccccc4)c3cc21] | 41% |
| 12o | 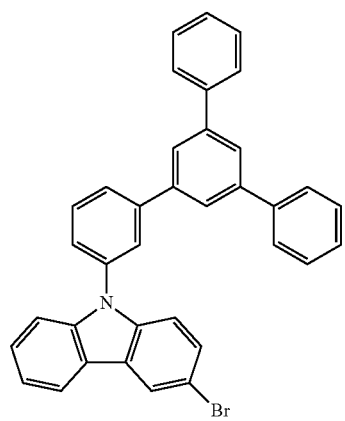<br>Ex. 10e | 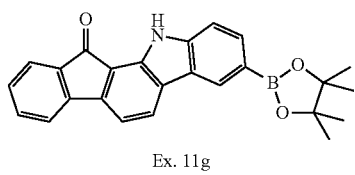 [SMILES: CC1(C)OB(c2ccc3[nH]c4c5c(ccc4c3c2)-c2ccccc2C5=O)OC1(C)C]<br>Ex. 11g | 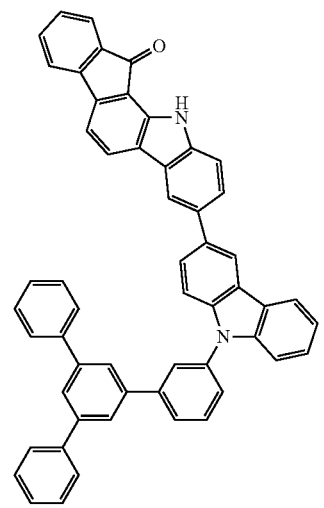 [SMILES: O=C1c2ccccc2-c2ccc3c([nH]c4ccc(-c5ccc6c(c5)c5ccccc5n6-c5cccc(-c6cc(-c7ccccc7)cc(-c7ccccc7)c6)c5)cc43)c21] | 44% |

| Ex. | Starting material 1 | Starting material 2 | Product | Yield |
|---|---|---|---|---|
| 12p | 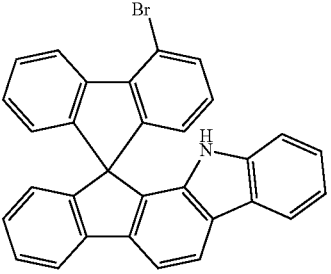 Ex.9c | 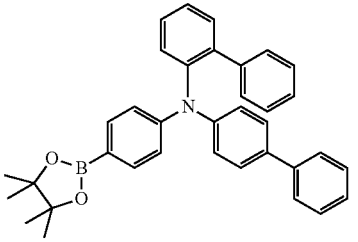 Ex. 2a | 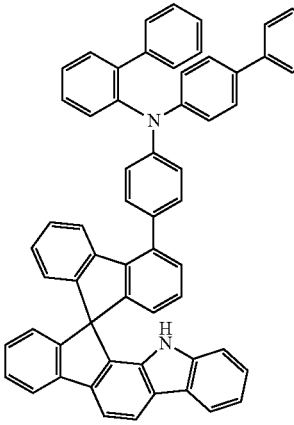 | 15% after column chromatography |

Example 13a: Synthesis of 12'-[3-(4,6-diphenyl-1,3,5-triazin-2-yl)-phenyl]-3'-(9-phenylcarbazol-3-yl)spiro[fluorine-9,7'-indeno[1,2-a]-carbazole]

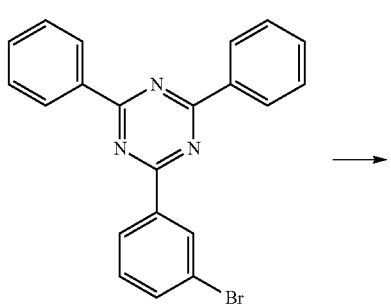

+

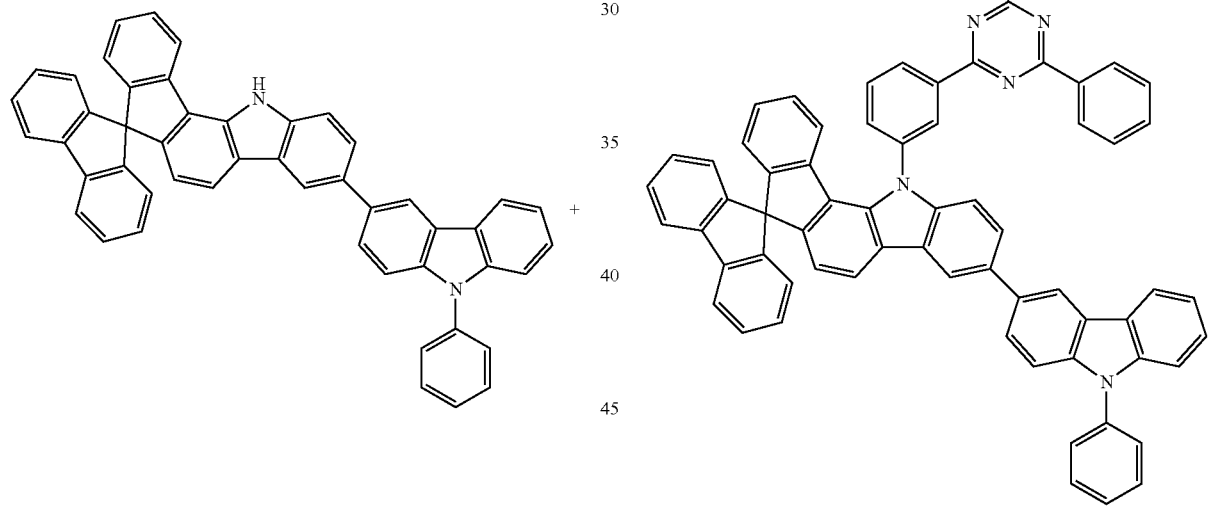

21.7 g (34 mmol) of 3-(9-phenylcarbazol-3-yl)spiro[12H-indeno[1,2-a]-carbazole-7,9'-fluorene] (from Ex. 12a) and 13.2 g (34 mmol) of 2-(3-bromophenyl)-4,6-diphenyl-1,3,5-triazine [1233200-57-1] are initially introduced in 280 ml of toluene and flushed with argon for 30 minutes. After addition of 175 mg (0.3 mmol) of bis(dibenzylideneacetone)palladium(0), 250 mg (0.6 mmol) of dicyclohexyl(2',6'-dimethoxybiphenyl-2-yl)phosphine and 4.4 g (46 mmol) of sodium tert-butoxide, the reaction mixture is heated under reflux for 45 h. After cooling to room temperature, 350 ml of water are stirred in, and the organic phase is separated off and freed from solvent. The residue is taken up in toluene, three times the volume of heptane are then stirred in, and the solid formed is filtered off with suction and recrystallised once from toluene. The product is finally purified by column chromatography through silica gel with a toluene/heptane eluent mixture (2:1). Drying in vacuo leaves 10.8 g (12 mmol, 36% of theory) of the product as pale-yellow solid having a purity of 99.8% according to HPLC.

The following compound can also be prepared analogously:

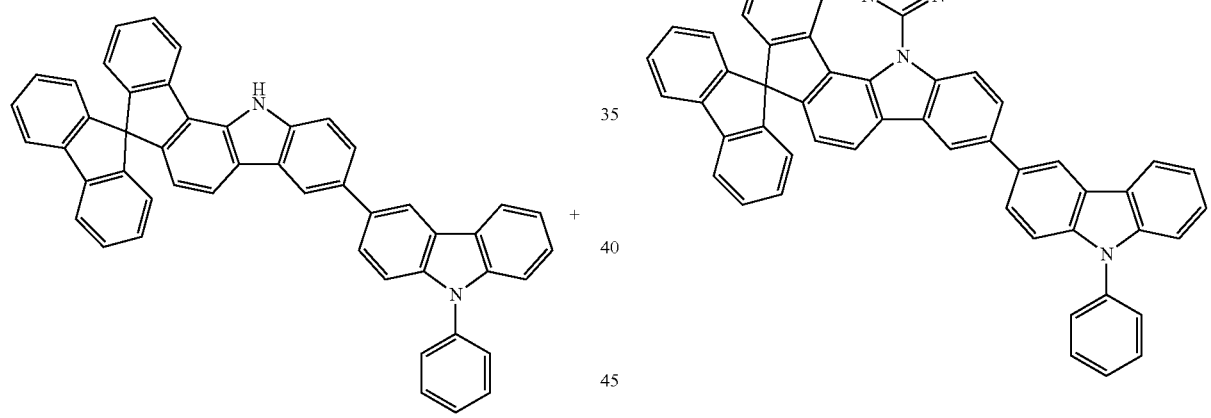

| Ex. | Starting material | Product | Yield |
|---|---|---|---|
| 13b | Ex.12c | | 39% |

Example 12a: Synthesis of 12'-(4,6-diphenyl-1,3,5-triazin-2-yl)-3'-(9-phenylcarbazol-3-yl)spiro[fluorine-9,7'-indeno[1,2-a]-carbazole]

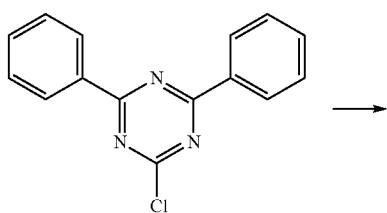

A solution of 67.9 g (105 mmol) of 3-(9-phenylcarbazol-3-yl)spiro[12H-indeno[1,2-a]carbazole-7,9'-fluorene] (Ex. 12a) in 300 ml of dimetylformamide is added dropwise with vigorous stirring to a solution of 4.2 g of sodium hydride (60% in mineral oil, 105 mmol) in 300 ml of dimethylformamide, and the mixture is stirred for 2 h. A solution of 30.0 g (112 mmol) of 2-chloro-4,6-diphenyl-1,3,5-triazine [3842-55-5] in 200 ml of THF is then slowly added dropwise, and the mixture is stirred for 18 h and subsequently poured onto about 150 g of ice. The organic phase is extended with 250 ml of toluene, separated off, washed twice with 100 ml of water and freed from solvent in a rotary evaporator. The residue which remains is extracted with hot toluene via aluminium oxide (basic, activity grade 1), the suspension formed is freed from solvent in a rotary evaporator, and the residue which remains is purified by column chromatography through silica gel with a heptane/THF eluent mixture (4:1). Removal of the solvents in a rotary evaporator and heating of the residue at 180° C. and a pressure of about $10^{-5}$ mbar for 5 h leaves 31.5 g (33 mmol, 31% of theory) of the product as colourless solid having a purity of 99.9% according to HPLC.

The following compounds can be prepared analogously:

| Ex. | Starting material 1 | Starting material 2 | Product | Yield |
|---|---|---|---|---|
| 14b | Ex. 12a | Ex. 3a | | 28% |
| 14c | Ex. 12a | Ex. 3b | | 37% |
| 14d | Ex. 12c | [3842-55-5] | | 36% |

-continued
| Ex. | Starting material 1 | Starting material 2 | Product | Yield |
|---|---|---|---|---|
| 14e | 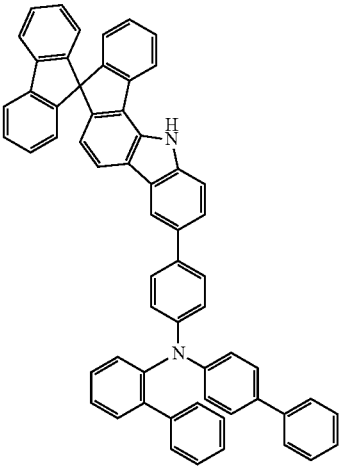<br>Ex. 12g | 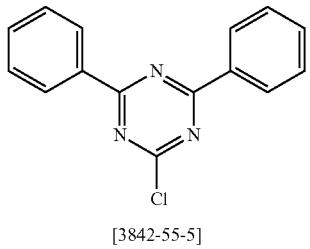 [SMILES: Clc1nc(-c2ccccc2)nc(-c2ccccc2)n1]<br>[3842-55-5] | 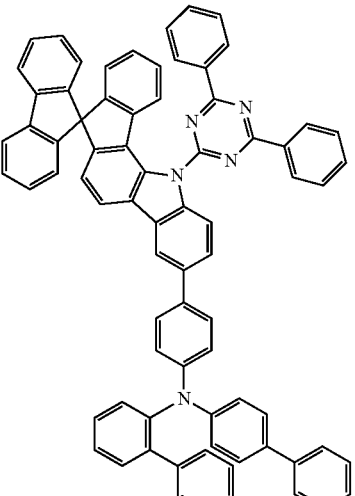 | 40% |
| 14f | 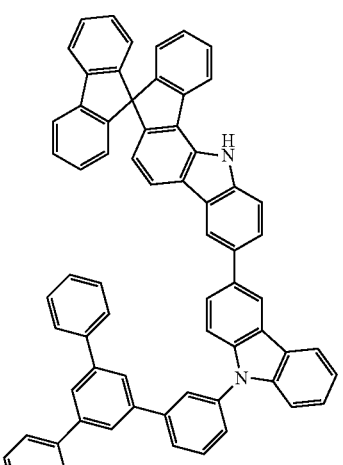<br>Ex. 12b | 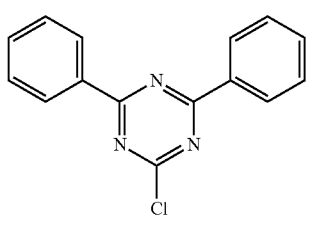<br>[3842-55-5] | 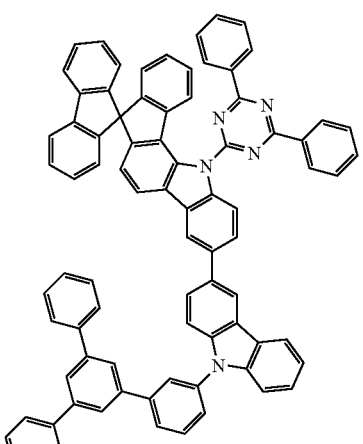 | 31% |
| 14g | 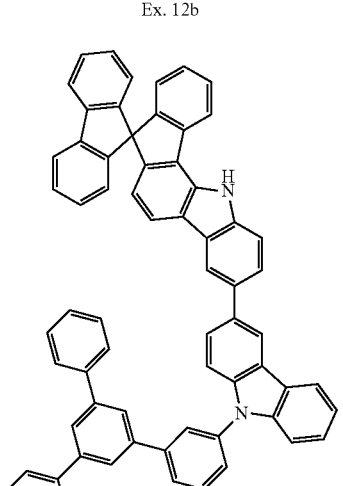<br>Ex. 12b | 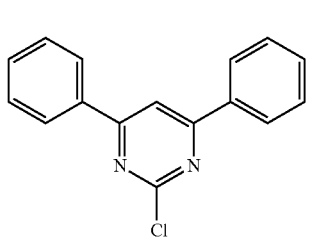<br>[2915-16-4] | 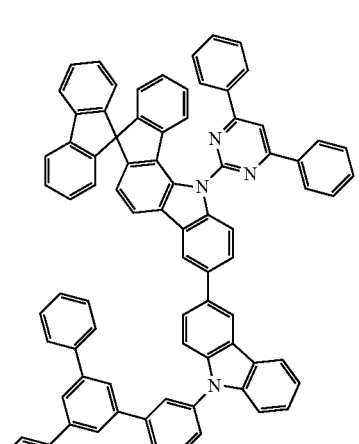 | 35% |

| Ex. | Starting material 1 | Starting material 2 | Product | Yield |
|---|---|---|---|---|
| 14h | 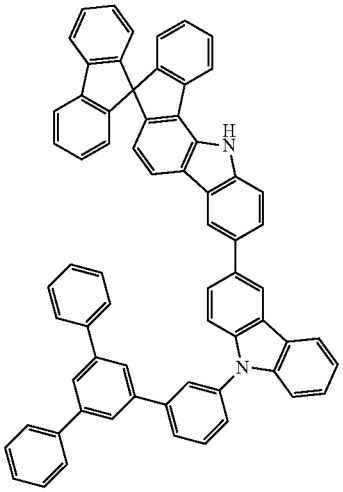 Ex. 12b | 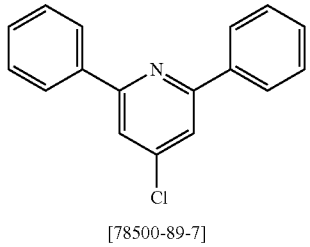 [SMILES: Clc1cc(-c2ccccc2)nc(-c2ccccc2)c1] [78500-89-7] | 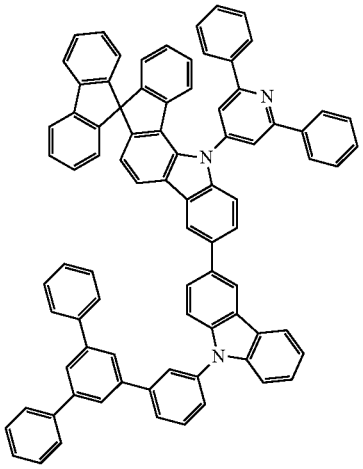 [SMILES: c1ccc(-c2cc(-c3ccccc3)cc(-c3cccc(-n4c5ccccc5c5cc(-c6ccc7c(c6)c6ccc8c(c6n7-c6cc(-c7ccccc7)nc(-c7ccccc7)c6)-c6ccccc6C86c7ccccc7-c7ccccc76)ccc54)c3)c2)cc1] | 26% |
| 14i | 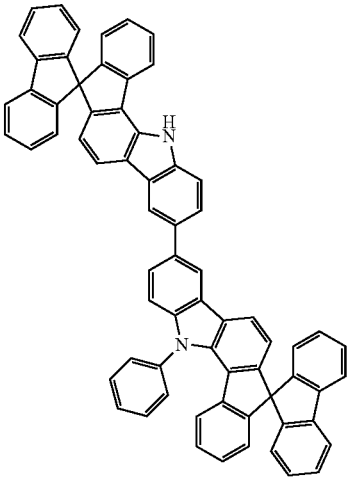 Ex. 12d | 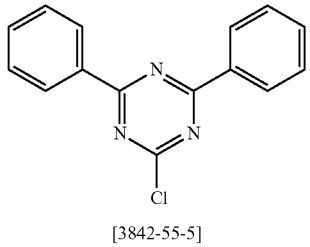 [3842-55-5] | 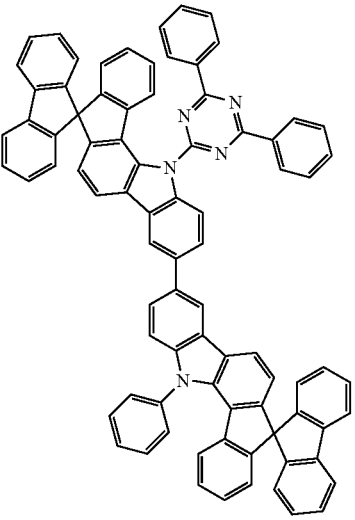 [SMILES: c1ccc(-c2nc(-c3ccccc3)nc(-n3c4ccc(-c5ccc6c(c5)c5ccc7c(c5n6-c5ccccc5)-c5ccccc5C75c6ccccc6-c6ccccc65)cc4c4ccc5c(c43)-c3ccccc3C53c4ccccc4-c4ccccc43)n2)cc1] | 30% |
| 14j | 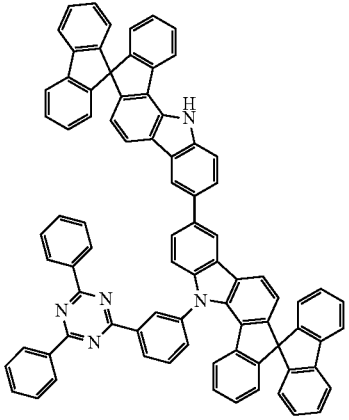 Ex. 12e | 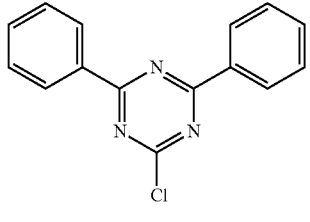 [3842-55-5] | 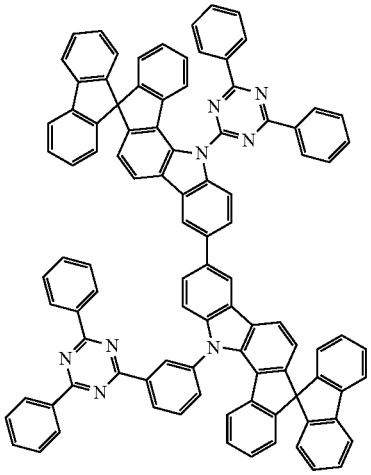 [SMILES: c1ccc(-c2nc(-c3ccccc3)nc(-c3cccc(-n4c5ccc(-c6ccc7c(c6)c6ccc8c(c6n7-c6nc(-c7ccccc7)nc(-c7ccccc7)n6)-c6ccccc6C86c7ccccc7-c7ccccc76)cc5c5ccc6c(c54)-c4ccccc4C64c5ccccc5-c5ccccc54)c3)n2)cc1] | 27% |

-continued
| Ex. | Starting material 1 | Starting material 2 | Product | Yield |
|---|---|---|---|---|
| 14k | Ex. 12f | [3842-55-5] | | 41% |
| 14l | Ex. 12h | [3842-55-5] | | 33% |
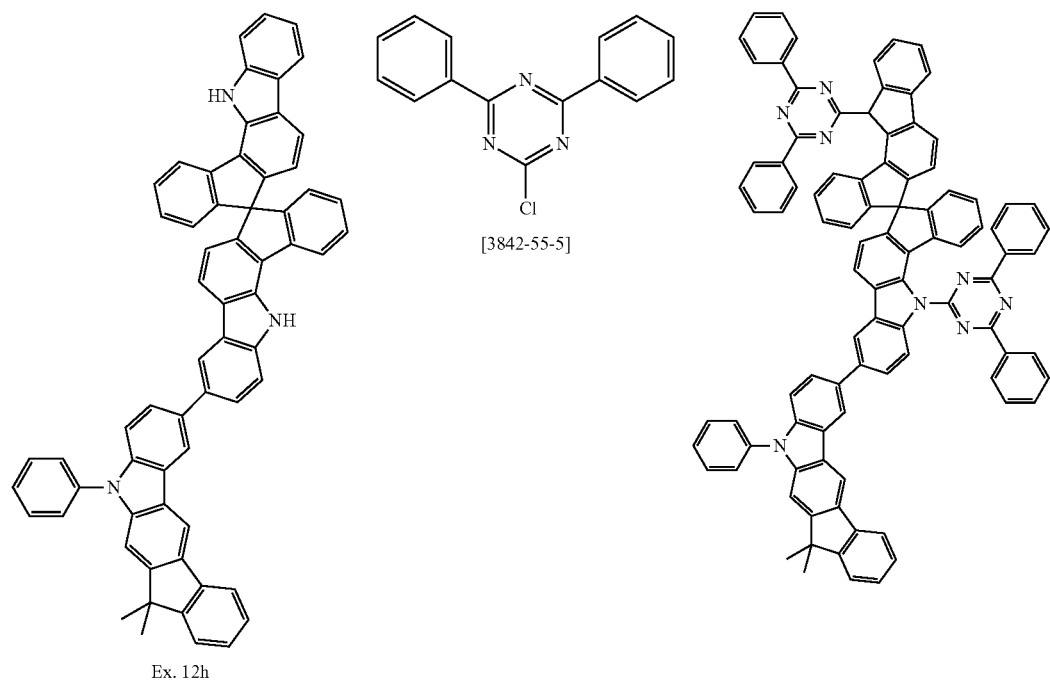

-continued
| Ex. | Starting material 1 | Starting material 2 | Product | Yield |
|---|---|---|---|---|
| 14m | 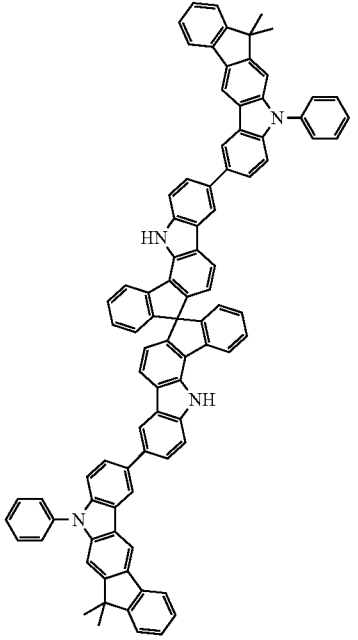\nEx. 12j | 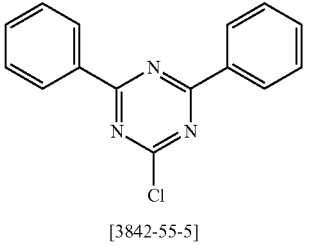\n[3842-55-5] | 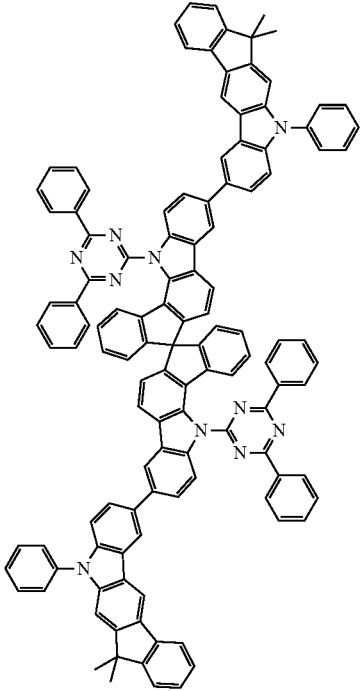 [SMILES: CC1(C)c2ccccc2-c2cc3c4cc(-c5ccc6c(c5)c5ccc7c(c5n6-c5nc(-c6ccccc6)nc(-c6ccccc6)n5)-c5ccccc5C75c6ccccc6-c6c5ccc5c7cc(-c8ccc9c(c8)c8cc%10c(cc8n9-c8ccccc8)C(C)(C)c8ccccc8-%10)ccc7n(-c7nc(-c8ccccc8)nc(-c8ccccc8)n7)c65)ccc4n(-c4ccccc4)c3cc21] | 36% |
| 14n | 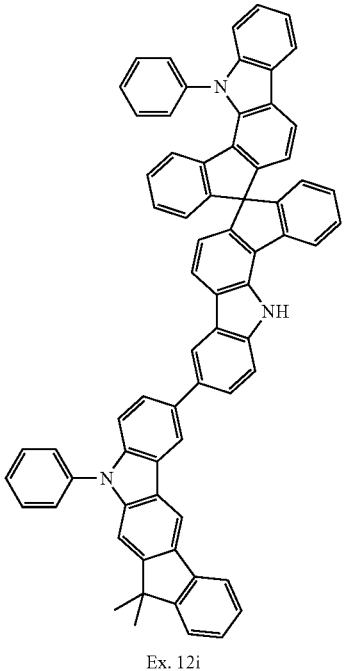 [SMILES: CC1(C)c2ccccc2-c2cc3c4cc(-c5ccc6[nH]c7c8c(ccc7c6c5)C5(c6ccccc6-8)c6ccccc6-c6c5ccc5c7ccccc7n(-c7ccccc7)c65)ccc4n(-c4ccccc4)c3cc21]\nEx. 12i | 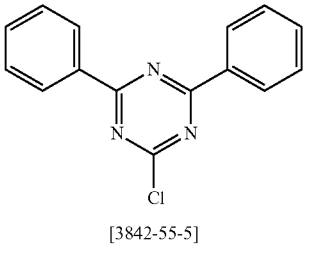 [SMILES: Clc1nc(-c2ccccc2)nc(-c2ccccc2)n1]\n[3842-55-5] | 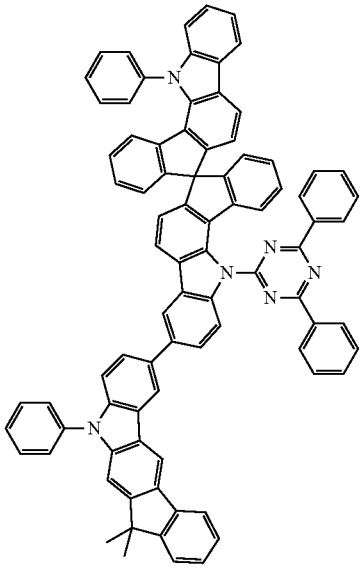 [SMILES: CC1(C)c2ccccc2-c2cc3c4cc(-c5ccc6c(c5)c5ccc7c(c5n6-c5nc(-c6ccccc6)nc(-c6ccccc6)n5)-c5ccccc5C75c6ccccc6-c6c5ccc5c7ccccc7n(-c7ccccc7)c65)ccc4n(-c4ccccc4)c3cc21] | 43% |

-continued
| Ex. | Starting material 1 | Starting material 2 | Product | Yield |
|---|---|---|---|---|
| 14o | 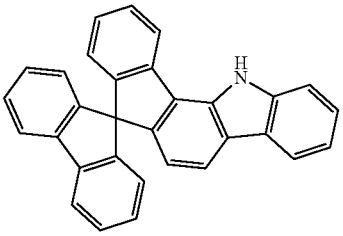<br>Ex. 7a | 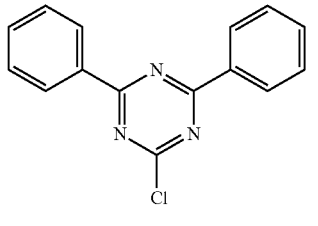<br>[3842-55-5] | 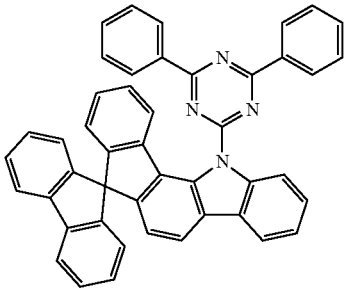 [SMILES: c1ccc(-c2nc(-c3ccccc3)nc(-n3c4ccccc4c4ccc5c(c43)-c3ccccc3C53c4ccccc4-c4ccccc43)n2)cc1] | 45% |
| 14p | 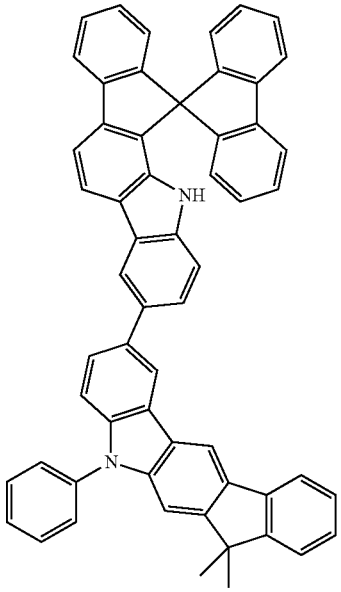<br>Ex. 9d | 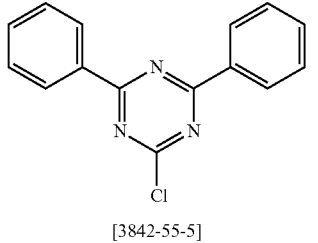 [SMILES: Clc1nc(-c2ccccc2)nc(-c2ccccc2)n1]<br>[3842-55-5] | 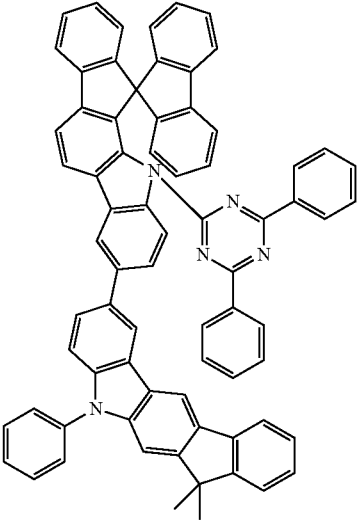 [SMILES: CC1(C)c2ccccc2-c2cc3c4cc(-c5ccc6c(c5)c5ccc7c(c5n6-c5nc(-c6ccccc6)nc(-c6ccccc6)n5)C5(c6ccccc6-c6ccccc65)c5ccccc5-7)ccc4n(-c4ccccc4)c3cc21] | 38% |
| 14q | 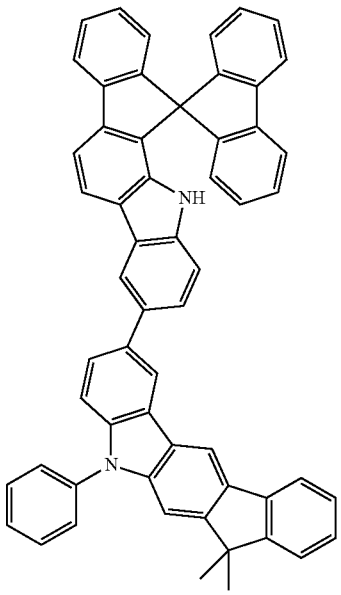<br>Ex. 9d | 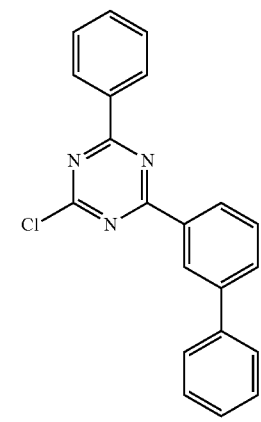<br>Ex. 3a | 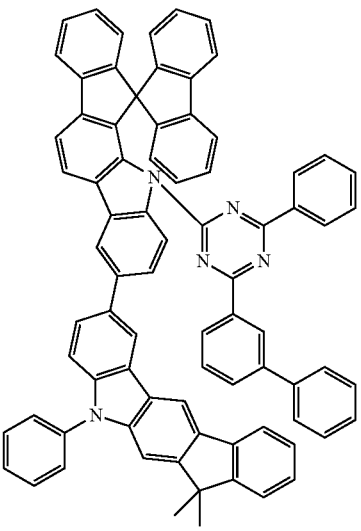 [SMILES: CC1(C)c2ccccc2-c2cc3c4cc(-c5ccc6c(c5)c5ccc7c(c5n6-c5nc(-c6ccccc6)nc(-c6cccc(-c8ccccc8)c6)n5)C5(c6ccccc6-c6ccccc65)c5ccccc5-7)ccc4n(-c4ccccc4)c3cc21] | 39% |

| Ex. | Starting material 1 | Starting material 2 | Product | Yield |
|---|---|---|---|---|
| 14r | Ex. 9e | [3842-55-5] | | 28% |
| 14s | Ex. 12l | [3842-55-5] | | 17% |

Examples AV2 and AV4

Comparative Examples AV2 and AV4 can be prepared by the processes described in DE 102008017591.

Example AV6

Comparative Example AV6 can be prepared by the processes described in WO 2011/132683.

DEVICE EXAMPLES

Device Example 1: Production of Solution-Processed OLEDs

The materials according to the invention can be processed from solution and lead, compared with vacuum-processed OLEDs, to OLEDs which can be produced significantly more simply, but nevertheless have good properties. For example, comparative materials 12m and 14o (Table 2) cannot be dissolved in toluene in a concentration of 15 mg/ml, whereas this is readily possible with materials 14a, 14g, 13b and 14e according to the invention (Table 1).

In order to check whether a solubility of 15 mg/ml or more in toluene arises for a material, the following process is followed: 30 mg of the material are initially introduced as a solid in a sample vial. 2 ml of toluene are added at room temperature. The vial is sealed, and the contents are stirred at 60° C. on a heatable magnetic stirrer for 1 h. Good thermal contact is ensured by means of an aluminium block with holes into which the vials fit accurately.

After 1 h, the vial is removed and allowed to cool to room temperature. A clear solution without relatively large particles is then present in the vial, so at least 15 mg/ml of the material are soluble in toluene.

Furthermore, the higher glass transition temperature of the matrix materials according to the invention allows drying by heating at elevated temperatures and thus offers a larger processing window than comparative materials 12m and 14o.

TABLE 1

Properties of selected matrix materials which are relevant for the processability from solution

| Compound from Ex. | Solubility in toluene >15 mg/ml | Tg >175° C. |
|---|---|---|
| 12m | no | no |
| 14o | no | no |
| 14a | yes | yes |
| 14g | yes | yes |
| 13b | yes | yes |
| 14e | yes | yes |

The production of fully solution-based OLEDs has already been described many times in the literature, for example in WO 2004/037887. The production of vacuum-based OLEDs has likewise been described many times, inter alia in WO 2004/058911. In the examples discussed below, layers applied on a solution basis and on a vacuum basis are combined within an OLED, so that the processing up to and including the emission layer was carried out from solution and the processing in the subsequent layers (hole-blocking layer and electron-transport layer) was carried out from vacuum. The general processes described above are for this purpose adapted to the circumstances described here (layer-thickness variation, materials) and combined as follows:

The structure is as follows:
substrate,
ITO (50 nm)
PEDOT:PSS (20 or 60 nm for green or red components respectively)
hole-transport layer (HTL) (20 nm)
emission layer (EML) (60 nm)
hole-blocking layer (HBL) (10 nm)
electron-transport layer (ETL) (40 nm)
cathode.

The substrate used is a glass plate coated with structured ITO (indium tin oxide) in a thickness of 50 nm. For better processing, these are coated with PEDOT:PSS (poly(3,4-ethylenedioxy-2,5-thiophene): polystyrene sulfonate, purchased from Heraeus Precious Metals GmbH & Co. KG, Germany). PEDOT:PSS is applied by spin coating from water in air and is subsequently dried by heating at 180° C. in air for 10 minutes in order to remove residual water. The interlayer and the emission layer are applied to these coated glass plates. The hole-transport layer used is crosslinkable. A polymer of the structure shown below, which can be synthesised in accordance with WO2010/097155, is used.

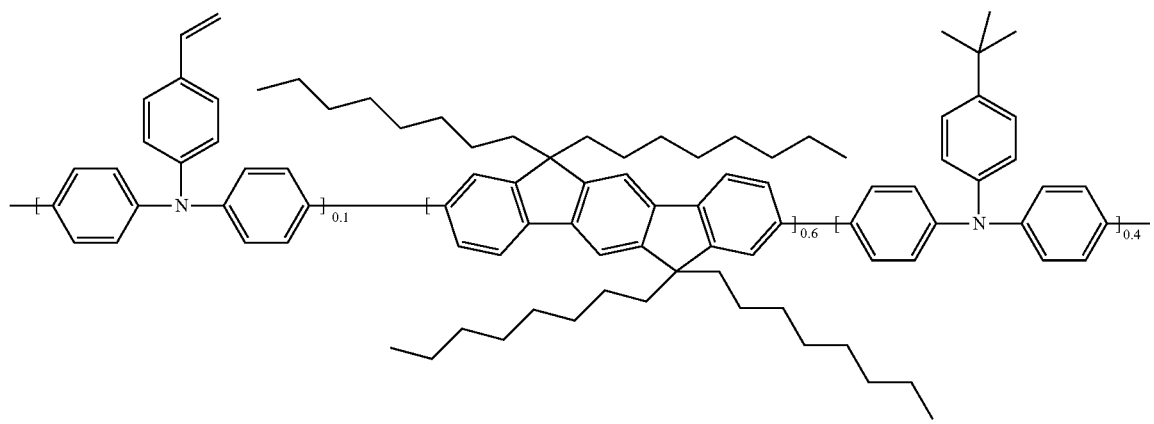

The hole-transport polymer is dissolved in toluene. The typical solids content of such solutions is about 5 g/l if, as here, the typical layer thickness of 20 nm for a device is to be achieved by means of spin coating. The layers are applied by spin coating in an inert-gas atmosphere, in the present case argon, and dried by heating at 180° C. for 60 minutes.

The emission layer is always composed of at least one matrix material (host material) and an emitting dopant (emitter). Furthermore, mixtures of a plurality of matrix materials and co-dopants may occur. An expression such as TMM-A (92%): dopant (8%) here means that material TMM-A is present in the emission layer in a proportion by weight of 92% and the dopant is present in the emission layer in a proportion by weight of 8%. The mixture for the emission layer is dissolved in toluene or optionally chlorobenzene. The typical solids content of such solutions is about 18 g/l if, as here, the typical layer thickness of 60 nm for a device is to be achieved by means of spin coating. The layers are applied by spin coating in an inert-gas atmosphere, in the present case argon, and dried by heating at 160° C. for 10 minutes. Matrix materials used are shown in Table 2—these are both compounds according to the invention and also comparative examples.

TABLE 2

Structures of matrix materials according to the invention and comparative matrices

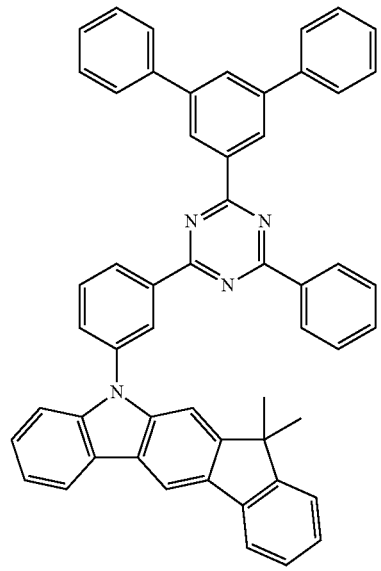

12m (SdT)

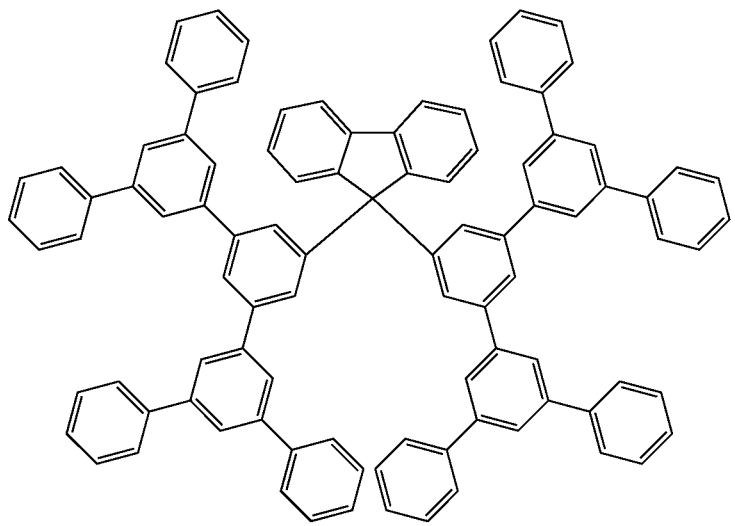

AV2

TABLE 2-continued
Structures of matrix materials according to the invention and comparative matrices
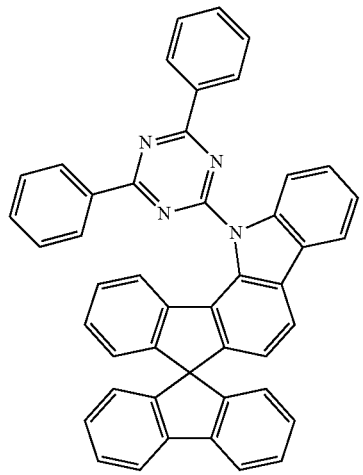
14o
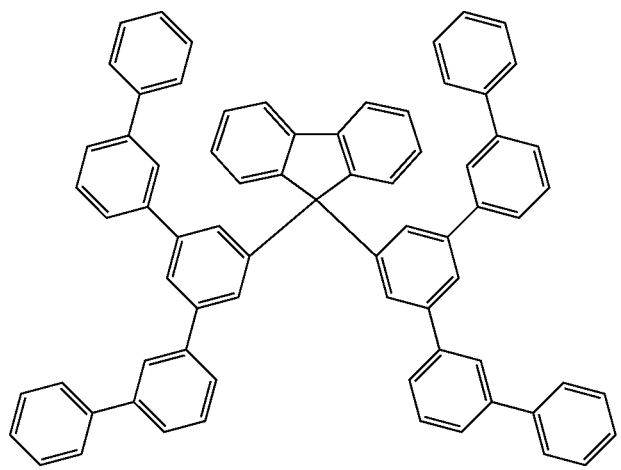
AV4

TABLE 2-continued
Structures of matrix materials according to the invention and comparative matrices
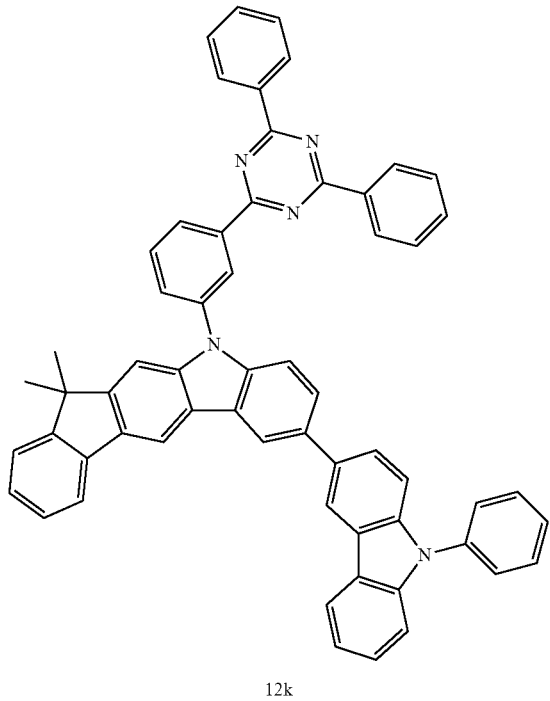 [SMILES: CC1(C)c2ccccc2-c2cc3c4cc(-c5ccc6c(c5)c5ccccc5n6-c5ccccc5)ccc4n(-c4cccc(-c5nc(-c6ccccc6)nc(-c6ccccc6)n5)c4)c3cc21]
12k
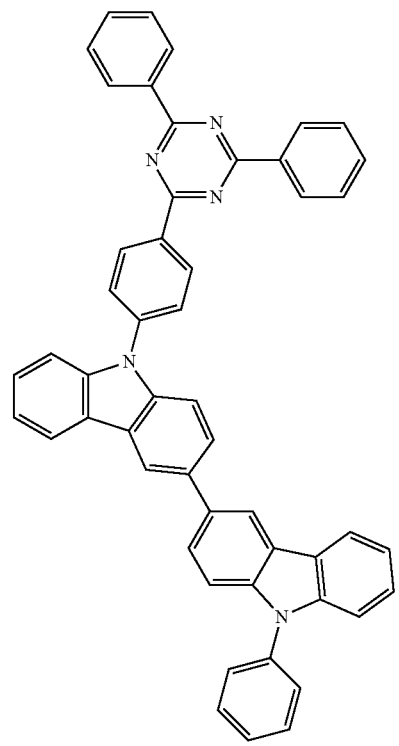
AV6

TABLE 2-continued
Structures of matrix materials according to the invention and comparative matrices
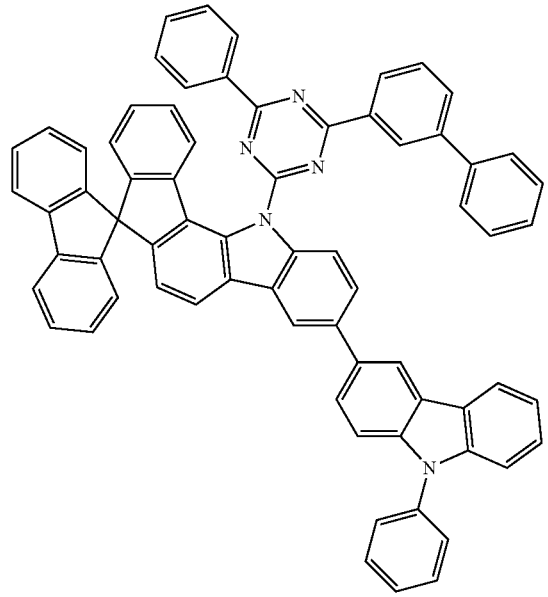
14b
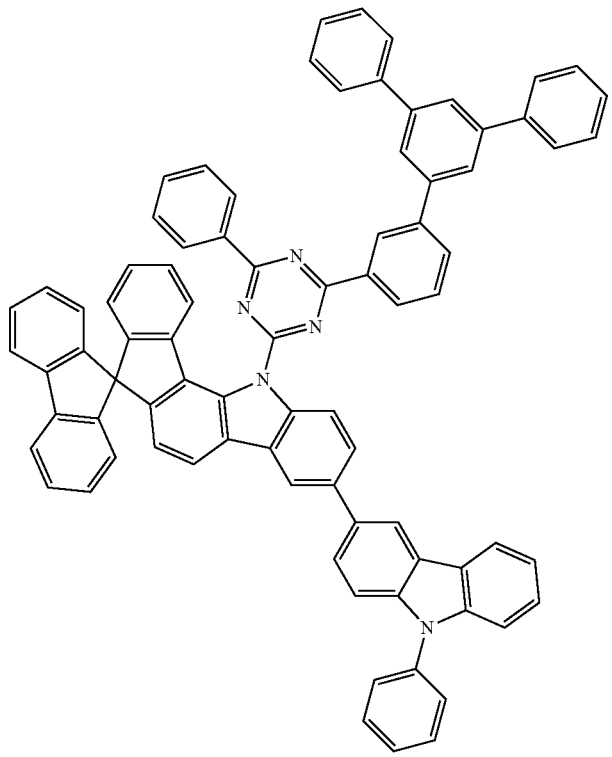
14c TABLE 2-continued
Structures of matrix materials according to the invention and comparative matrices
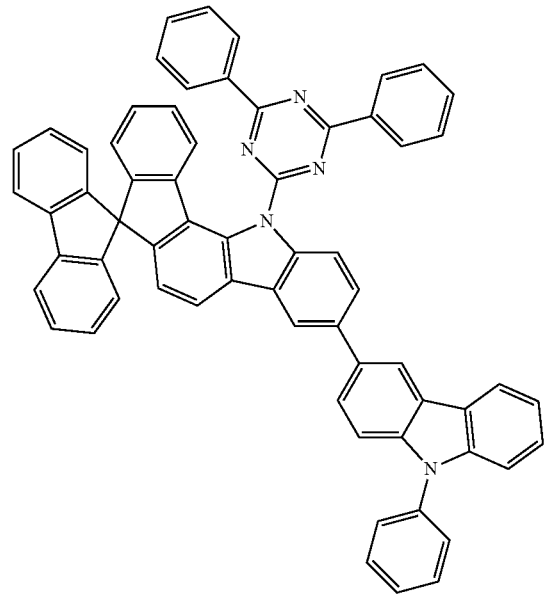
14a
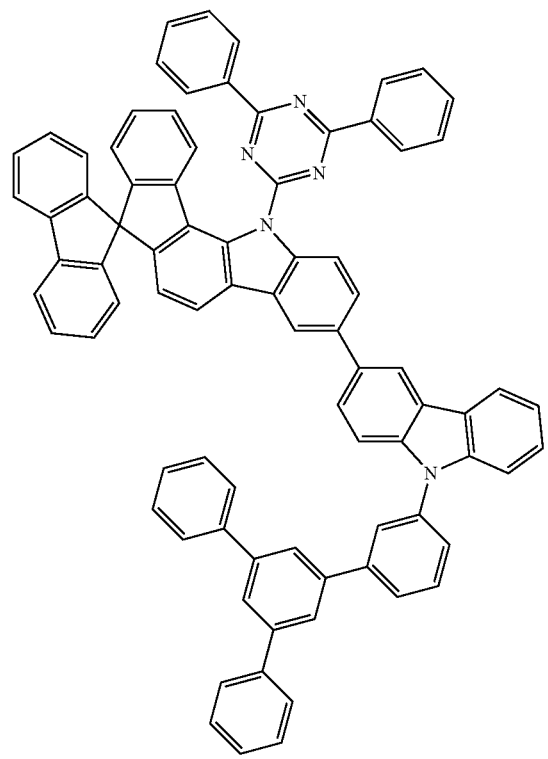
14f TABLE 2-continued
Structures of matrix materials according to the invention and comparative matrices
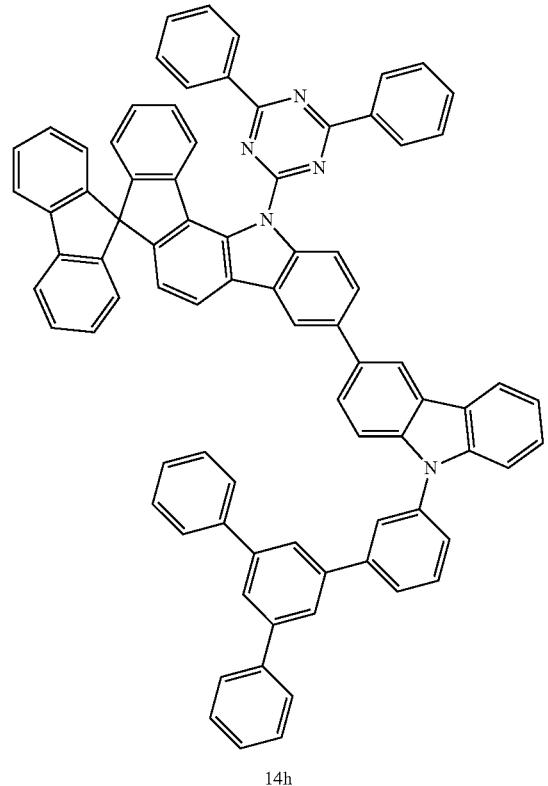 [SMILES: c1ccc(-c2cc(-c3ccccc3)cc(-c3cccc(-n4c5ccccc5c5cc(-c6ccc7c(c6)c6ccc8c(c6n7-c6nc(-c7ccccc7)nc(-c7ccccc7)n6)-c6ccccc6C86c7ccccc7-c7ccccc76)ccc54)c3)c2)cc1]
14h
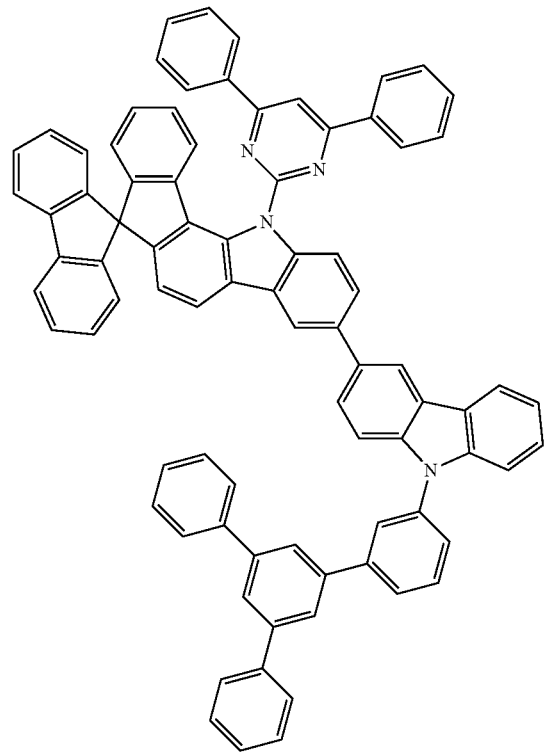
14g TABLE 2-continued
Structures of matrix materials according to the invention and comparative matrices
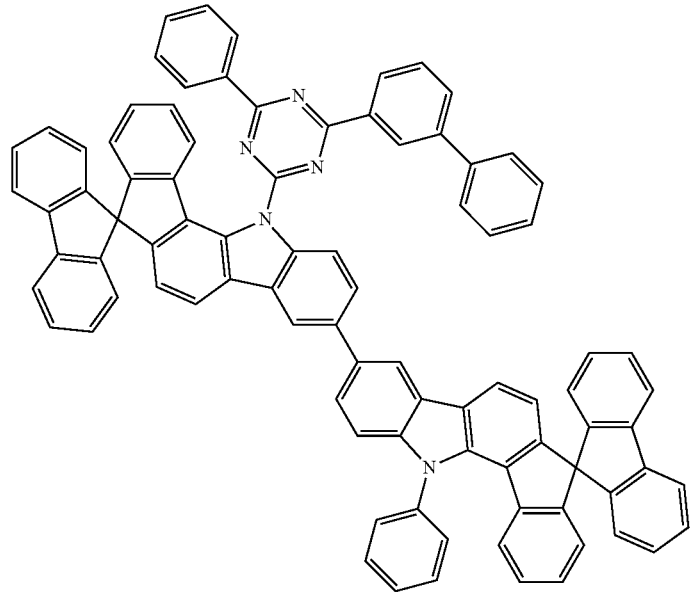
14i
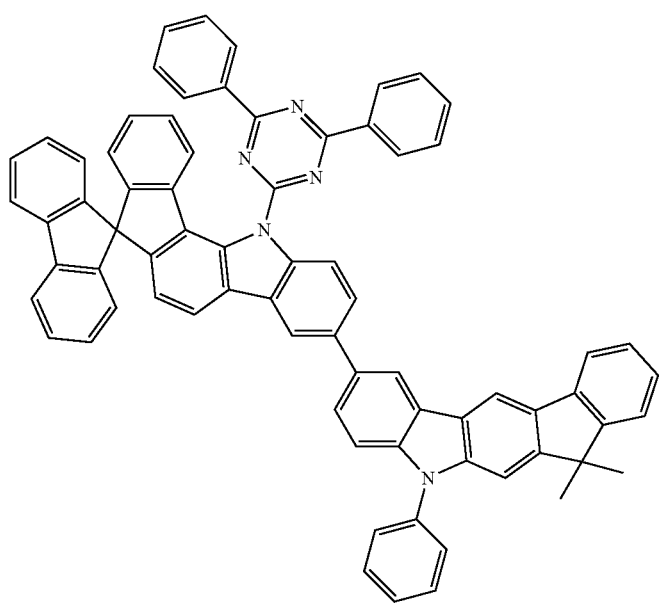
14d TABLE 2-continued
Structures of matrix materials according to the invention and comparative matrices
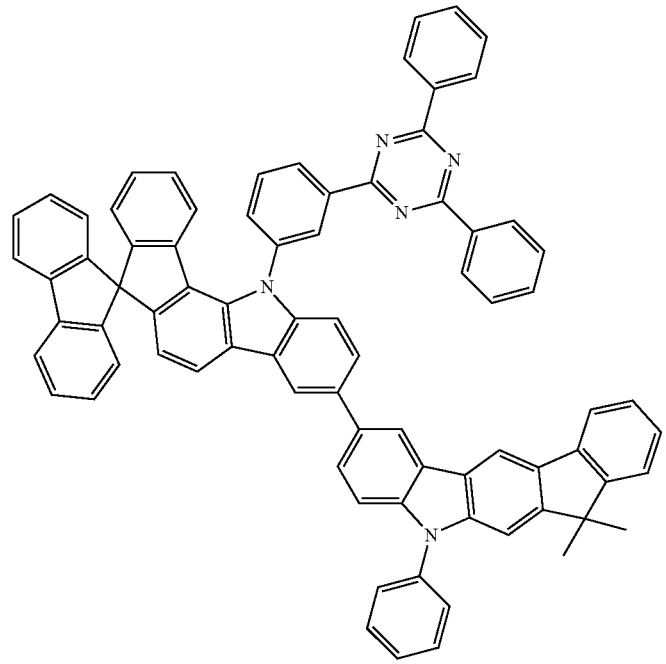
13b
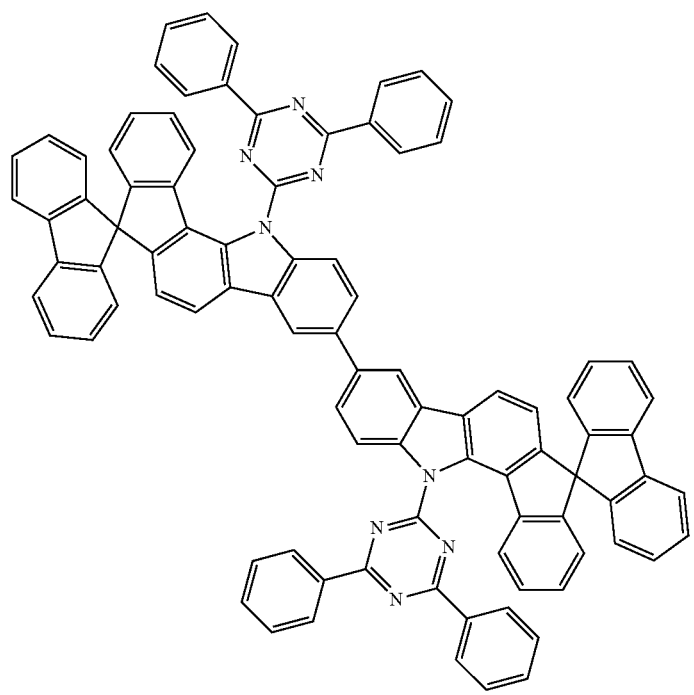
14k TABLE 2-continued
Structures of matrix materials according to the invention and comparative matrices
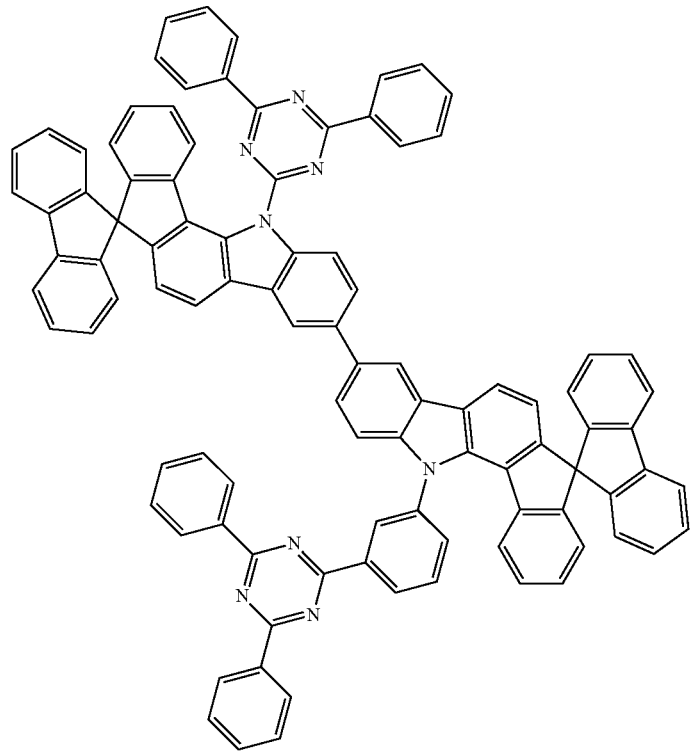
14j
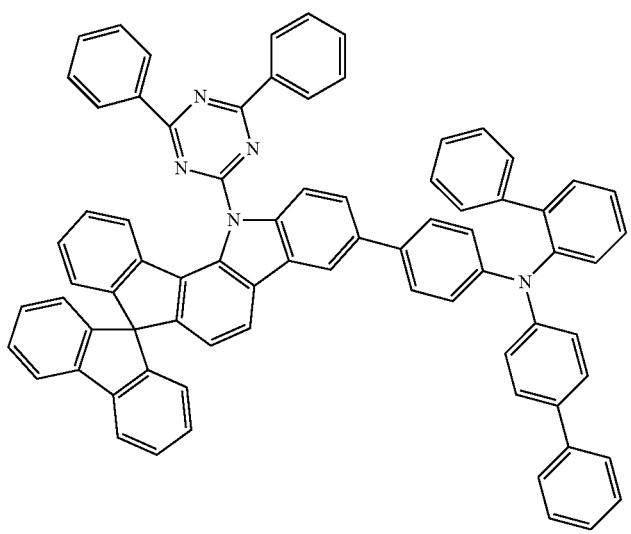
14e TABLE 2-continued
Structures of matrix materials according to the invention and comparative matrices
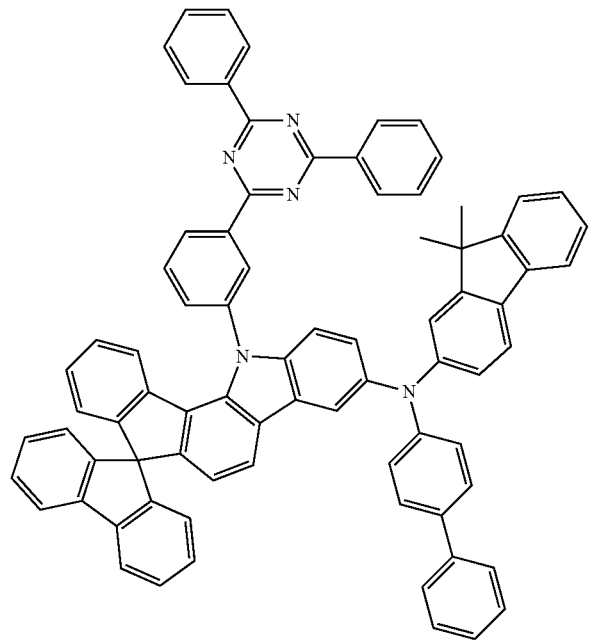
8d
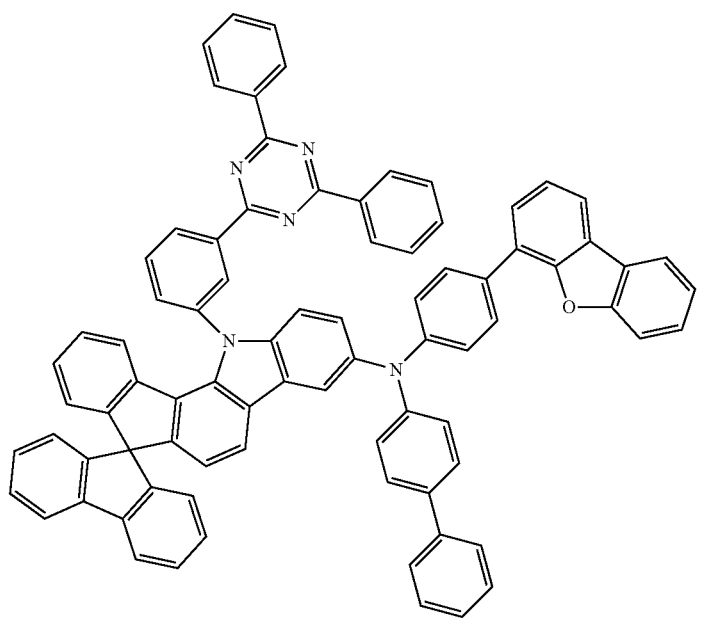
8e TABLE 2-continued
Structures of matrix materials according to the invention and comparative matrices
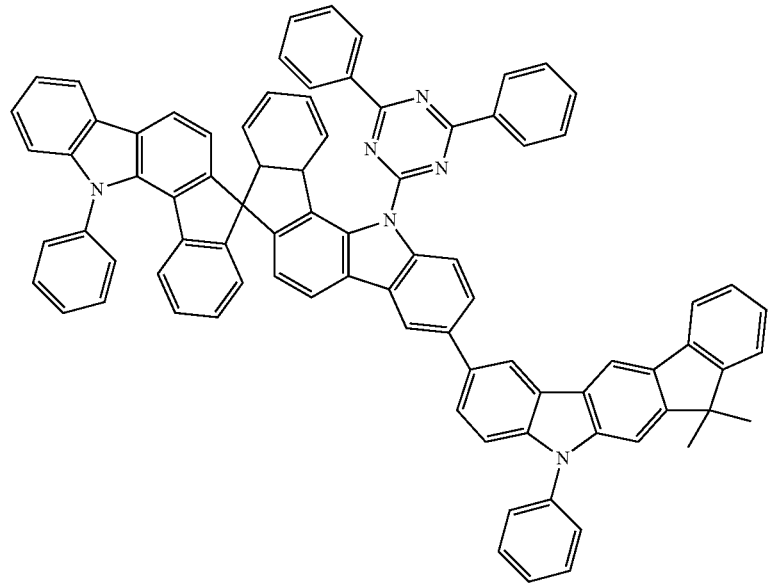
14n
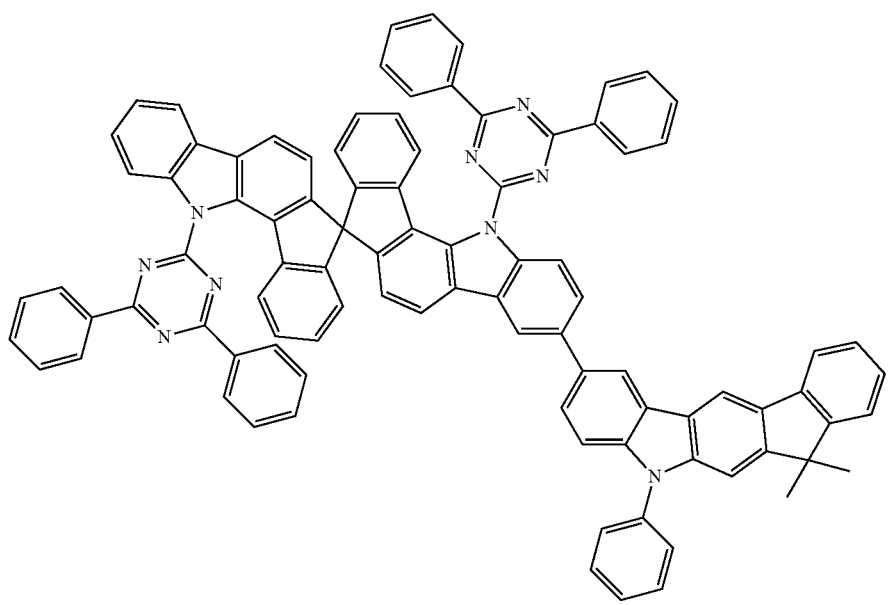
14l TABLE 2-continued
Structures of matrix materials according to the invention and comparative matrices
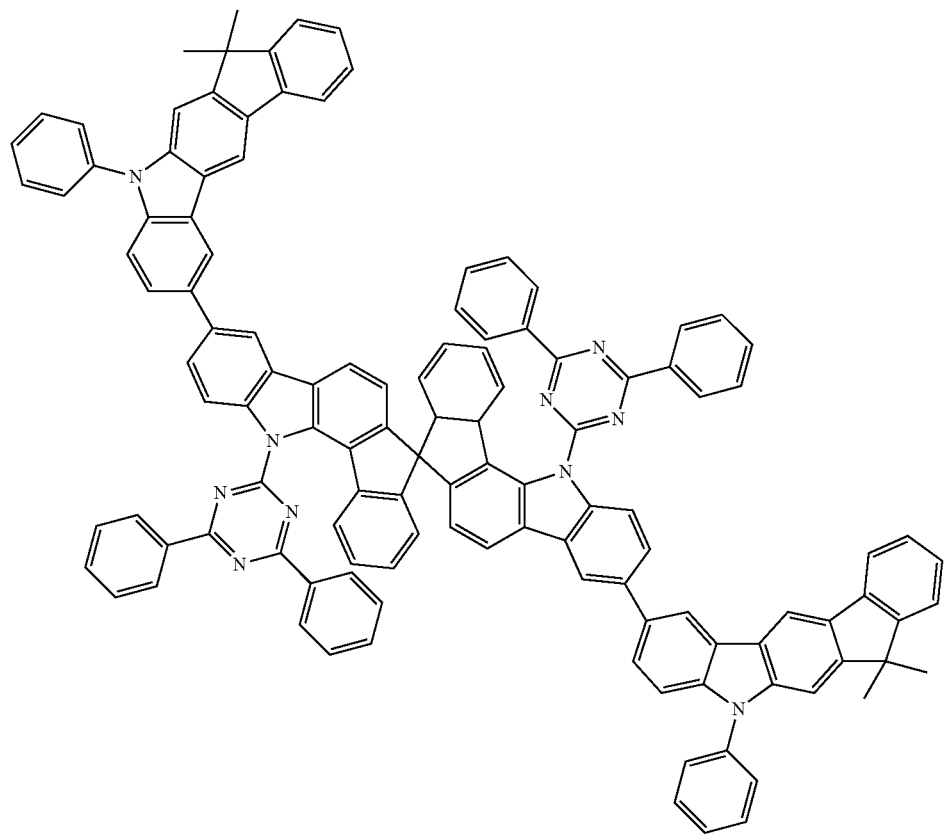
14m
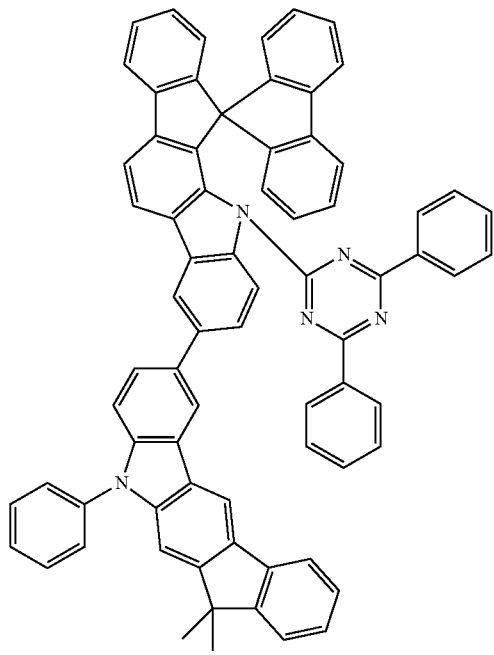
14p TABLE 2-continued
Structures of matrix materials according to the invention and comparative matrices
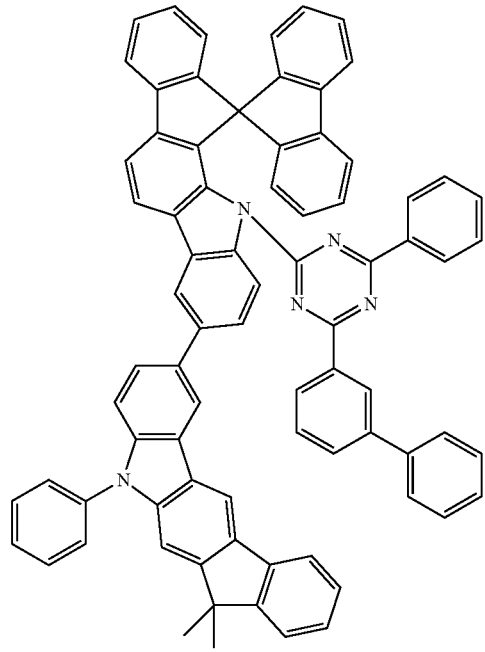
14q
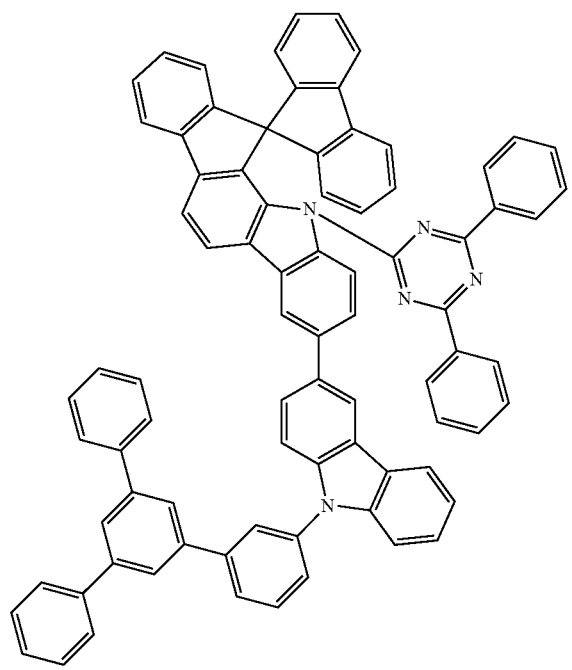
14r TABLE 2-continued
Structures of matrix materials according to the invention and comparative matrices
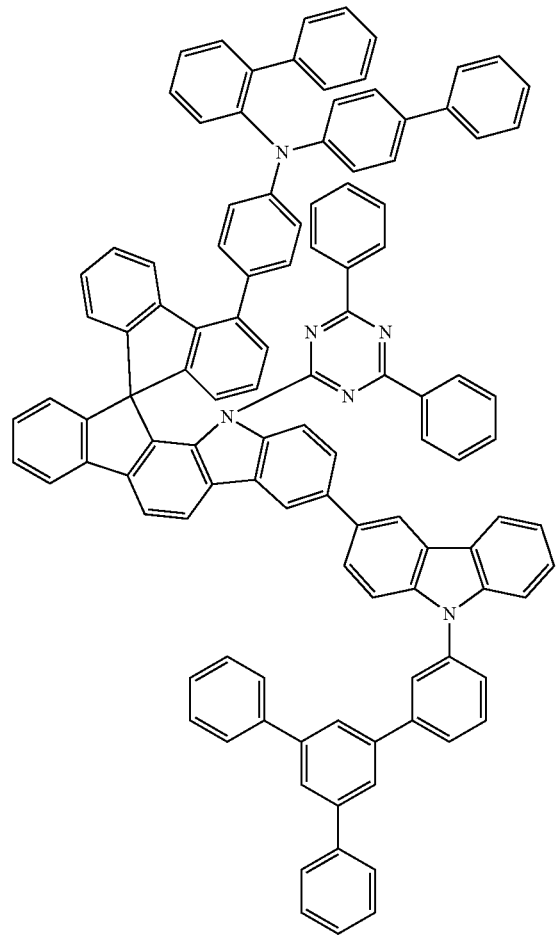
14s
The dopants used in the present case are shown in Table 3.
TABLE 3
Dopants used
TABLE 3-continued
Dopants used
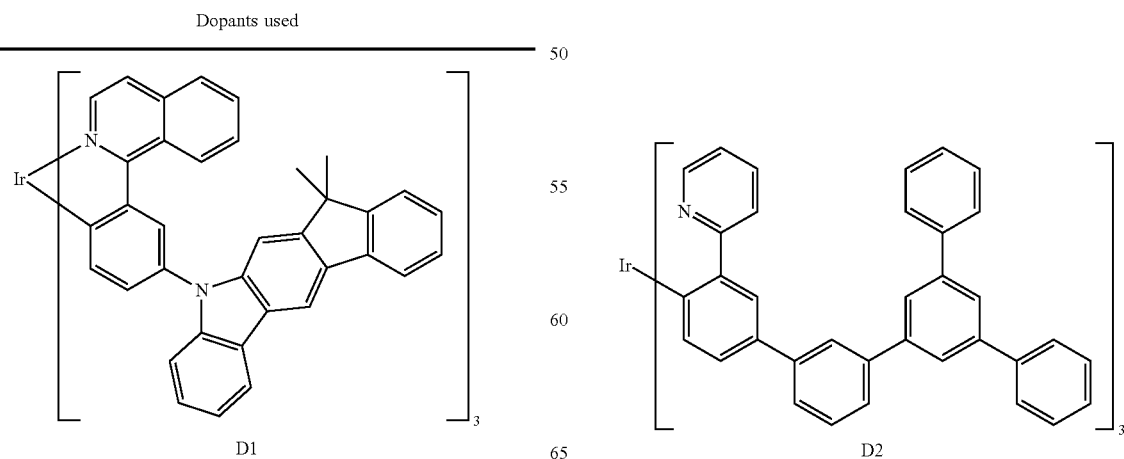
D1
D2

TABLE 3-continued

Dopants used

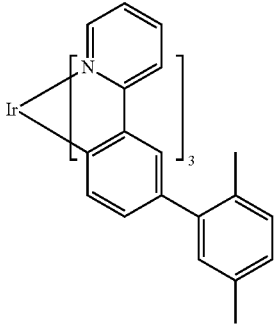

D3

The materials for the hole-blocking layer and electron-transport layer are applied by thermal vapour deposition in a vacuum chamber. The electron-transport layer here may consist, for example, of more than one material which are admixed with one another in a certain proportion by volume by co-evaporation. An expression such as ETM1:ETM2 (50%:50%) here means that materials ETM1 and ETM2 are present in the layer in a proportion by volume of 50% each. The materials used in the present case are shown in Table 4.

TABLE 4

HBL and ETL materials used

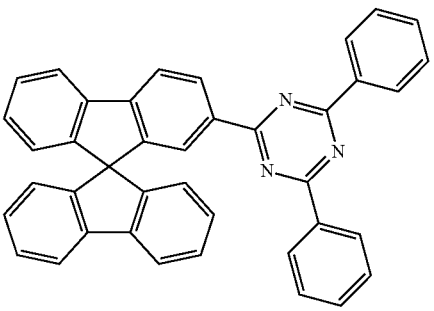

ETM1

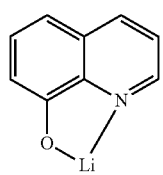

ETM2

The cathode is formed by the thermal vapour deposition of an aluminium layer with a thickness of 100 nm. The OLEDs are characterised by standard methods. For this purpose, the electroluminescence spectra, current/voltage/luminous density characteristic lines (IUL characteristic lines), assuming Lambert emission characteristics, and the (operating) lifetime are determined. The IUL characteristic lines are used to determine characteristic numbers, such as the operating voltage U (in V) and the external quantum efficiency (in %) at a certain luminance. LT80 @ 8000 cd/m$^2$ is the lifetime by which the OLED has dropped to 80% of the initial intensity from an initial luminance of 8000 cd/m$^2$, i.e. to 6400 cd/m$^2$. Correspondingly, LT80 @ 10000 cd/m$^2$ is the lifetime by which the OLED has dropped to 80% of the initial intensity from an initial luminance of 10000 cd/m$^2$, i.e. to 8000 cd/m$^2$.

The data of OLEDs whose EMLs consist of TMM-A, TMM-B and dopant D (in accordance with Table 2 and Table 3) are shown in Table 5. ETM-1 is used as HBL and ETM1:ETM2 (50%:50%) as ETL.

TABLE 5

Results of solution-processed OLEDs comprising EML mixtures of the type x % of TMM-A, (100-x-y) % of TMM-B, y % of dopant D

| Ex. | TMM-A Material | % | TMM-B Material | % | Dopant D Material | % | Efficiency at 1000 cd/m$^2$ % EQE | Voltage at 1000 cd/m$^2$ [V] | LT80 at 8000 cd/m$^2$ [h] |
|---|---|---|---|---|---|---|---|---|---|
| V1 | 12m | 40 | AV2 | 30 | D2 | 30 | 19.0 | 5.5 | 236 |
| 1  | 14b | 40 | AV2 | 30 | D2 | 30 | 19.8 | 5.2 | 289 |
| V2 | 12m | 40 | AV2 | 40 | D2 | 20 | 16.0 | 5.2 | 166 |
| V6 | AV6 | 40 | AV2 | 40 | D2 | 20 | 18.4 | 5.1 | 267 |
| 2  | 14b | 40 | AV2 | 40 | D2 | 20 | 19.4 | 5.1 | 417 |
| 3  | 14c | 40 | AV2 | 40 | D2 | 20 | 19.5 | 4.9 | 410 |
| 4  | 14a | 40 | AV2 | 40 | D2 | 20 | 18.9 | 5.1 | 380 |
| 5  | 14f | 40 | AV2 | 40 | D2 | 20 | 19.5 | 5.0 | 337 |
| 6  | 14h | 40 | AV2 | 40 | D2 | 20 | 17.2 | 5.5 | 293 |
| 7  | 14g | 40 | AV2 | 40 | D2 | 20 | 19.7 | 5.3 | 406 |
| 8  | 14i | 40 | AV2 | 40 | D2 | 20 | 19.5 | 5.0 | 392 |
| 9  | 14d | 40 | AV2 | 40 | D2 | 20 | 19.4 | 5.1 | 364 |
| 10 | 13b | 40 | AV2 | 40 | D2 | 20 | 19.3 | 5.1 | 374 |
| 11 | 14k | 40 | AV2 | 40 | D2 | 20 | 18.4 | 5.4 | 359 |
| 12 | 14j | 40 | AV2 | 40 | D2 | 20 | 18.6 | 5.5 | 344 |
| 13 | 14e | 40 | AV2 | 40 | D2 | 20 | 19.0 | 5.3 | 317 |
| 14 | 8d  | 40 | AV2 | 40 | D2 | 20 | 18.8 | 5.1 | 331 |
| 15 | 8e  | 40 | AV2 | 40 | D2 | 20 | 18.5 | 5.0 | 332 |
| 16 | 14n | 40 | AV2 | 40 | D2 | 20 | 19.5 | 5.1 | 367 |
| 17 | 14l | 40 | AV2 | 40 | D2 | 20 | 19.4 | 5.2 | 350 |
| 18 | 14m | 40 | AV2 | 40 | D2 | 20 | 19.4 | 5.1 | 364 |
| 19 | 14p | 40 | AV2 | 40 | D2 | 20 | 18.8 | 5.2 | 308 |
| 20 | 14q | 40 | AV2 | 40 | D2 | 20 | 19.2 | 5.2 | 324 |
| 21 | 14r | 40 | AV2 | 40 | D2 | 20 | 19.0 | 5.1 | 341 |
| 22 | 14s | 40 | AV2 | 40 | D2 | 20 | 19.4 | 5.0 | 288 |
| V3 | 12m | 20 | AV2 | 60 | D2 | 20 | 18.6 | 5.3 | 240 |
| 23 | 14c | 20 | AV2 | 60 | D2 | 20 | 20.1 | 5.2 | 551 |

The data of OLEDs whose EMLs consist of TMM-A, TMM-B, co-dopant D1 and dopant D (in accordance with Table 2 and Table 3) are shown in Table 6. ETM-1 is used as HBL and ETM1:ETM2 (50%:50%) as ETL here.

TABLE 6

Results of solution-processed OLEDs comprising EML mixtures of the type x % of TMM-A, (100-x-y-z) % of TMM-B, z % of co-dopant C, y % of dopant D

| Ex. | TMM-A Material | % | TMM-B Material | % | Co-dopant C Material | % | Dopant D Material | % | Eff. at 1000 cd/m$^2$ % EQE | U at 1000 cd/m$^2$ [V] | LT80 at 8000 cd/m$^2$ [h] |
|---|---|---|---|---|---|---|---|---|---|---|---|
| V4 | 12m | 39 | AV2 | 45 | D1 | 10 | D3 | 6 | 14.1 | 7.3 | 75 |
| 24 | 14f | 39 | AV2 | 45 | D1 | 10 | D3 | 6 | 14.2 | 6.9 | 178 |
| V5 | 12m | 40 | AV2 | 24 | D1 | 30 | D3 | 6 | 13.2 | 6.7 | 162 |
| 25 | 14f | 40 | AV2 | 24 | D1 | 30 | D3 | 6 | 13.4 | 6.6 | 244 |

Device Example 2: Production of Vacuum-Processed OLEDs

Many of the materials according to the invention can also be applied by vacuum vapour deposition. In the examples discussed below, exclusively layers applied on a vacuum basis are used. The general processes described above are for this purpose adapted to the circumstances described here (layer-thickness variation, materials). The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL) and finally a cathode. The cathode is formed by an aluminium layer with a thickness of 100 nm. The precise structure of the OLEDs and the results obtained are shown in Table 8. The auxiliary materials required for the production of the OLEDs are shown in Table 7; materials according to the invention and comparative materials are shown in Table 2.

TABLE 7

Structures of the auxiliary materials used

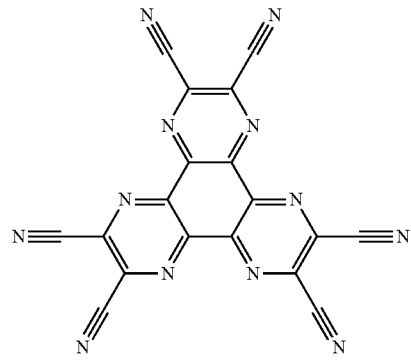

HATCN

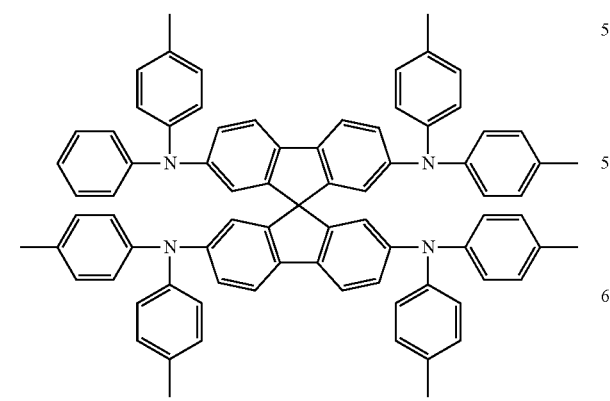

SpA1

TABLE 7-continued

Structures of the auxiliary materials used

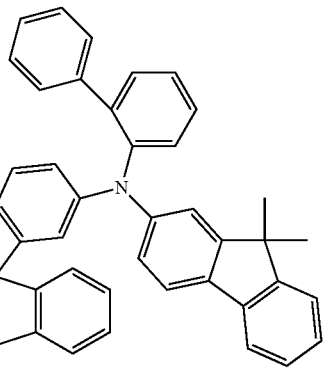

SpMA1

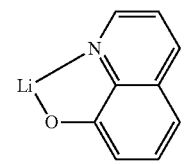

LiQ

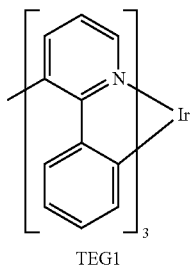

TEG1

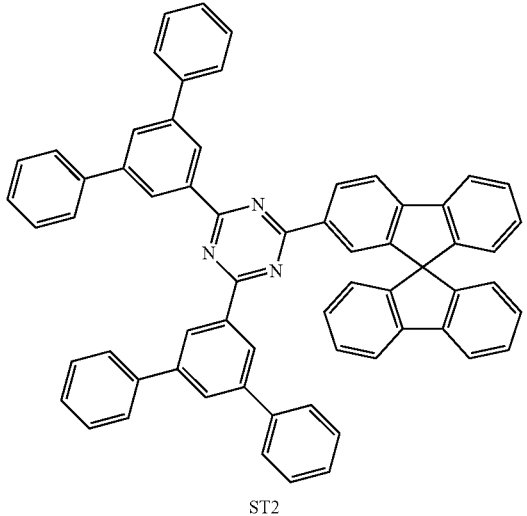 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1 ; "ST2"]

ST2

TABLE 7-continued

Structures of the auxiliary materials used

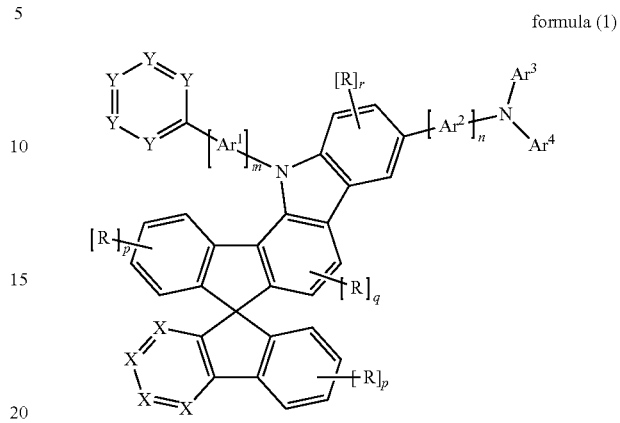

SDT1

TABLE 8

Structure of vacuum-processed OLEDs

| Ex. | HTL Thickness | IL Thickness | EBL Thickness | EML Thickness | HBL Thickness | ETL Thickness |
|---|---|---|---|---|---|---|
| V6 | SpA1 70 nm | HATCN 5 nm | SpMA1 90 nm | 12k:TEG1 (90%:10%) 30 nm | SDT1 10 nm | ST2:LiQ 50%:50% 30 nm |
| 26 | SpA1 70 nm | HATCN 5 nm | SpMA1 90 nm | 14b:TEG1 (90%:10%) 30 nm | SDT1 10 nm | ST2:LiQ (50%:50%) 30 nm |
| 27 | SpA1 70 nm | HATCN 5 nm | SpMA1 90 nm | 12m:14e:TEG1 (58%:30%:12%) 30 nm | SDT1 10 nm | ST2:LiQ (50%:50%) 30 nm |
| 28 | SpA1 70 nm | HATCN 5 nm | SpMA1 90 nm | 14b:AV4:TEG1 (58%:30%:12%) 30 nm | SDT1 10 nm | ST2:LiQ (50%:50%) 30 nm |

TABLE 9

Results of vacuum-processed OLEDs

| Ex. | Efficiency at 1000 cd/m² | Voltage at 1000 cd/m² | LT80 at 20 mA/cm² |
|---|---|---|---|
| V6 | 3.3 | 15.60% | 110 |
| 26 | 3.3 | 15.80% | 145 |
| 27 | 3.0 | 17.90% | 72 |
| 28 | 3.4 | 19.10% | 205 |

The invention claimed is:

1. A compound of the formula (1), formula (1)

where the following applies to the symbols and indices used:

Y is on each occurrence, identically or differently, CR or N, with the proviso that at least one group Y stands for N;

X is on each occurrence, identically or differently, CR or N, where a maximum of two groups X stand for N; or two adjacent X stand for a group of the following formula (3) or (4) and the other groups X stand, identically or differently, for CR or N, formula (3)

formula (4)

where ˆ indicates the corresponding adjacent groups X in formula (1) or formula (2);

V is on each occurrence, identically or differently, NR, $C(R)_2$, O, S, BR, $Si(R)_2$ or C=O;

Z is on each occurrence, identically or differently, CR or N, where a maximum of two groups Z stand for N;

$Ar^1$ is an aromatic or heteroaromatic ring system having 5 to 40 aromatic ring atoms, which may be substituted by one or more radicals R;

$Ar^2$, $Ar^3$, $Ar^4$ are on each occurrence, identically or differently, an aromatic or heteroaromatic ring system having 5 to 40 aromatic ring atoms, which may be substituted by one or more radicals R; $Ar^e$ and $Ar^3$ and/or $Ar^3$ and $Ar^4$ here may also be connected to one another by a single bond or by a group selected from $C(R^1)_2$, $C(R^1)_2$—$C(R^1)_2$, $NR^1$, O or S;

R is selected on each occurrence, identically or differently, from the group consisting of H, D, F, Cl, Br, I, CN, $NO_2$, $N(R^{11})_2$, $C(=O)Ar^5$, $C(=O)R^1$, $P(=O)(Ar^5)_2$, $P(Ar^5)_2$, $B(Ar^5)_2$, $Si(Ar^5)_3$, $Si(R^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C=CR^1$, $C\equiv C$, $Si(R^1)_2$, $C=O$, $C=S$, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, an aromatic or heteroaromatic ring system selected from the group consisting of benzene, naphthalene, anthracene, benzanthracene, phenanthrene, pyrene, chrysene, perylene, fluoranthene, naphthacene, pentacene, benzopyrene, biphenyl, biphenylene, terphenyl, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, di benzofuran, thiophene, benzothiophene, isobenzothio-phene, di benzothiophene, pyrrole, indole, isoindole, carbazole, and a combination of these systems, which may in each case be substituted by one or more radicals $R^1$, an aryloxy or heteroaryloxy group having 5 to 40 aromatic ring atoms, which may be substituted by one or more radicals $R^1$; two adjacent substituents R here may optionally form a monocyclic or polycyclic, aliphatic, aromatic or heteroaromatic ring system, which may be substituted by one or more radicals $R^1$;

$Ar^5$ is on each occurrence, identically or differently, an aromatic or heteroaromatic ring system having 5 to 30 aromatic ring atoms, which may be substituted by one or more non-aromatic radicals $R^1$; two radicals $Ar^5$ here which are bonded to the same N, P, B or Si atom may also be bridged to one another by a single bond or a bridge selected from $N(R^1)$, $C(R^1)_2$, $C(R^1)_2$—$C(R^1)_2$, O or S;

$R^1$ is selected on each occurrence, identically or differently, from the group consisting of H, D, F, CN, an aliphatic hydrocarbon radical having 1 to 20 C atoms, or an aromatic or heteroaromatic ring system having 5 to 30 aromatic ring atoms, in which one or more H atoms may be replaced by D, F, CN or an alkyl group having 1 to 10 C atoms, where two or more adjacent substituents $R^1$ may form a mono- or polycyclic, aliphatic ring system with one another;

$R^{11}$ is selected on each occurrence, identically or differently, from the group consisting of H, D, F, CN, an aliphatic hydrocarbon radical having 1 to 20 C atoms, or an alkyl group having 1 to 10 C atoms;

m is 0 or 1;
n is 0 or 1;
p is on each occurrence, identically or differently, 0, 1, 2, 3 or 4;
q is 0, 1 or 2;
r is 0, 1, 2 or 3;

with the proviso that the following compound is excluded:

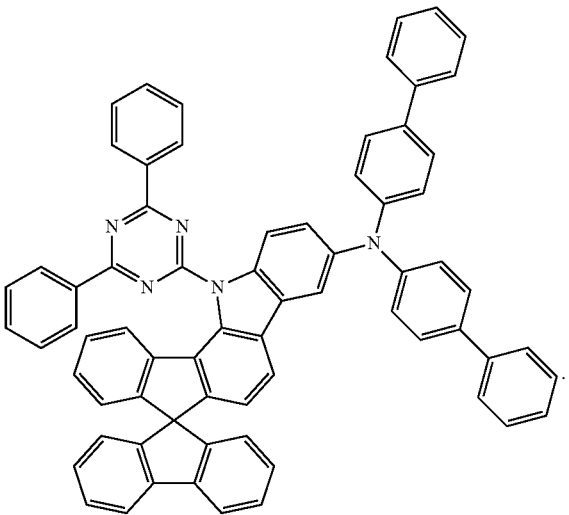 [SMILES: c1ccc(-c2ccc(N(c3ccc(-c4ccccc4)cc3)c3ccc4c(c3)c3ccc5c(c3n4-c3nc(-c4ccccc4)nc(-c4ccccc4)n3)-c3ccccc3C53c4ccccc4-c4ccccc43)cc2)cc1]

2. The compound according to claim 1, wherein X stands, identically or differently on each occurrence, for CR or N, where a maximum of one group X per ring stands for N; or two adjacent groups X stand for a group of the formula (3), where Z stands, identically or differently on each occurrence, for CR and V stands for NR, $C(R)_2$, O or S, and the other X stand for CR.

3. The compound according to claim 1, wherein the compound is selected from the compounds of the formulae (5) to (7), formula (5)

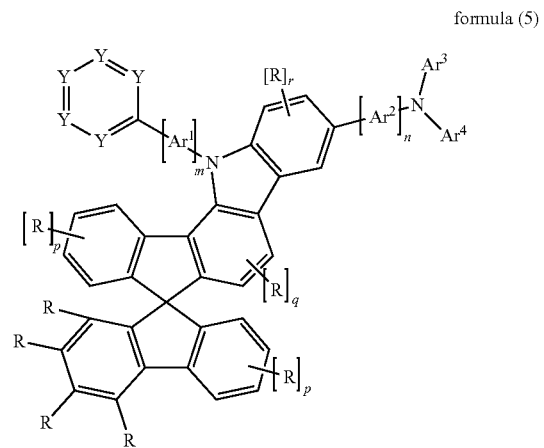

formula (6)

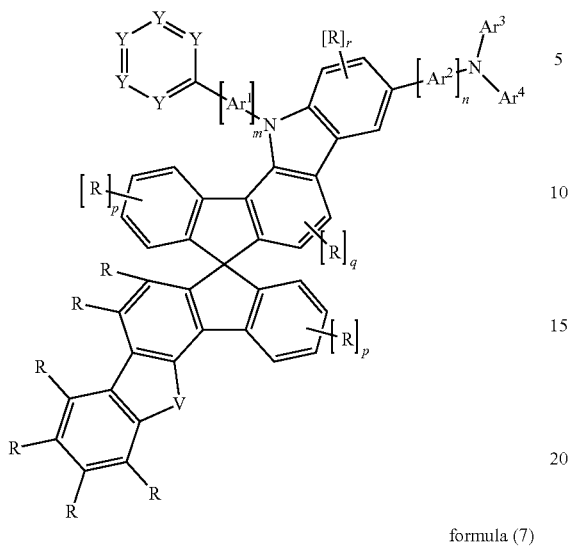

formula (6a)

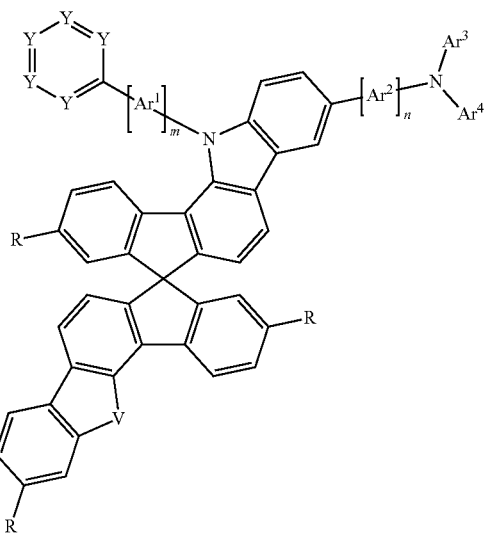

formula (7)

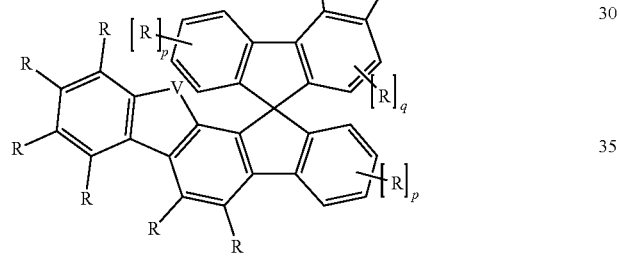

4. The compound according to claim 1, wherein p is on each occurrence, identically or differently, 0, 1 or 2 and in that q is equal to 0 or 1 and in that r is equal to 0 or 1.

5. The compound according to claim 1, wherein the compound is selected from the compounds of the formulae (5a) to (7a), formula (7a)

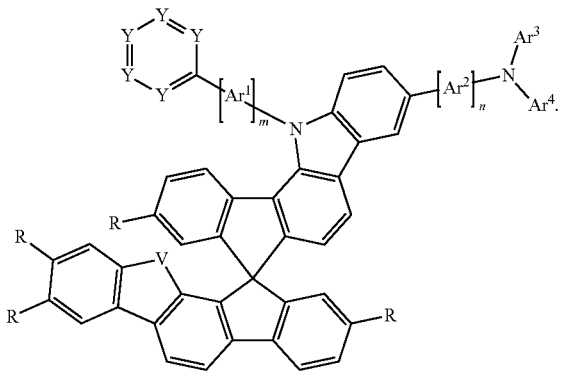

6. The compound according to claim 1, wherein the compounds is selected from the compounds of the formulae (5b) to (7b), formula (5a)

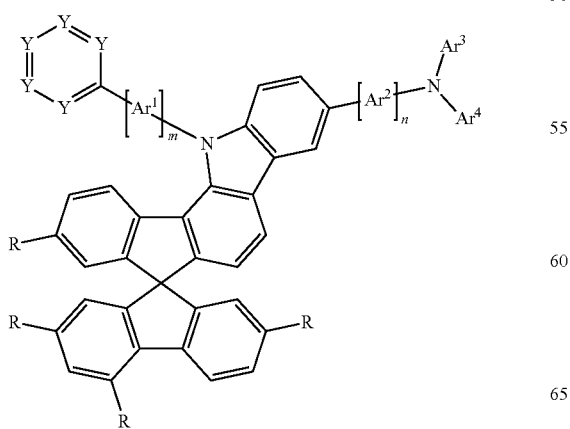

formula (5b)

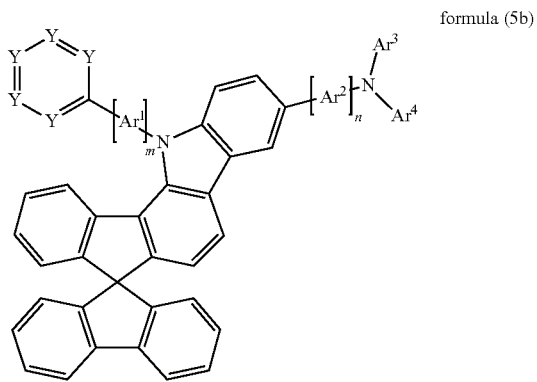

formula (6b)

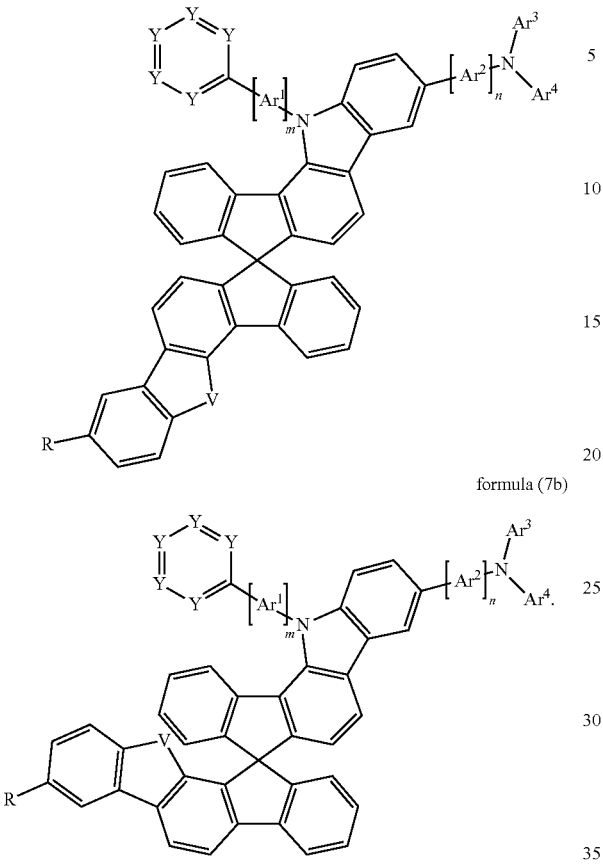

formula (7b)

7. The compound according to claim 1, wherein R is selected, identically or differently on each occurrence, from the group consisting of H, D, F, CN, N(Ar$^5$)$_2$, C(=O)Ar$^5$, P(=O)(Ar$^5$)$_2$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which may be substituted by one or more radicals R$^1$, where one or more non-adjacent CH$_2$ groups may be replaced by O and where one or more H atoms may be replaced by D or F, or an aromatic or heteroaromatic ring system selected from the group consisting of benzene, naphthalene, anthracene, benzanthracene, phenanthrene, pyrene, chrysene, perylene, fluoranthene, naphthacene, pentacene, benzopyrene, biphenyl, biphenylene, terphenyl, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, and a combination of these systems, which may in each case be substituted by one or more radicals R$^1$.

8. The compound according to claim 1, wherein the group

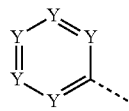

in formula (1) is selected from the group of the formulae (Het-Ar-1) to (Het-Ar-10),

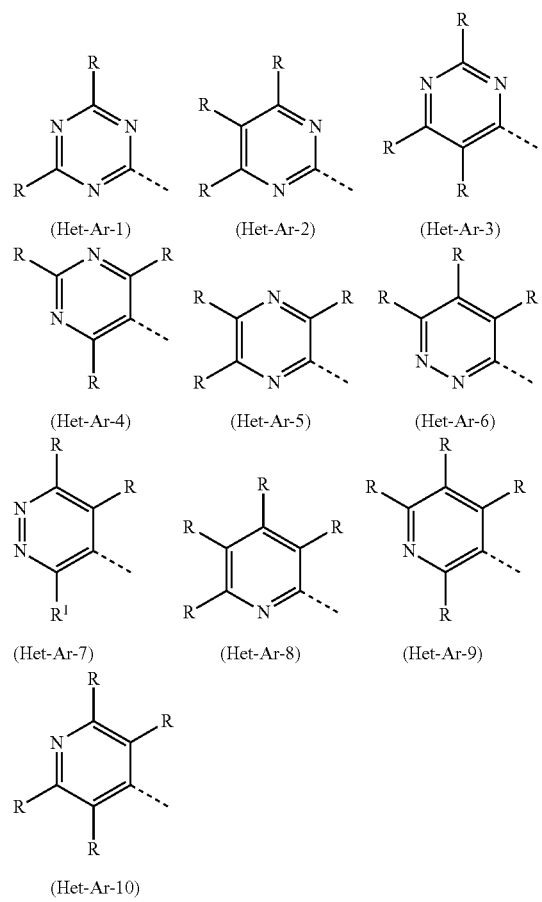

where the dashed bond represents the bond to Ar$^1$ or, for m=0, the bond to the nitrogen and R stands, identically or differently on each occurrence, for H, D or an aromatic or heteroaromatic ring system atoms selected from the group consisting of benzene, naphthalene, anthracene, benzanthracene, phenanthrene, pyrene, chrysene, perylene, fluoranthene, naphthacene, pentacene, benzopyrene, biphenyl, biphenylene, terphenyl, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, and a combination of these systems, which may be substituted by one or more radicals R$^1$.

9. The compound according to claim 1, wherein n=1 and Ar$^2$ and Ar$^3$ are connected to one another by a single bond or in that n=0 or 1 and Ar$^3$ and Ar$^4$ are connected to one another by a single bond or in that n=0 or 1 and none of the groups Ar$^2$, Ar$^3$ and Ar$^4$ are connected to one another.

10. The compound according to claim 1, wherein Ar$^2$ is an aromatic or heteroaromatic ring system having 6 to 24 aromatic ring atoms, which may be substituted by one or more radicals R and in that Ar$^3$ and Ar$^4$ represent, identically or differently on each occurrence, an aromatic or heteroaromatic ring system having 6 to 24 aromatic ring atoms, which may in each case be substituted by one or more radicals R.

11. The compound according to claim 1, wherein the group —[Ar$^2$]$_n$—N(Ar$^3$)(Ar$^4$) in formula (1) or formula (2) is selected from the groups of the formulae (CARB-1) to (CARB-5),

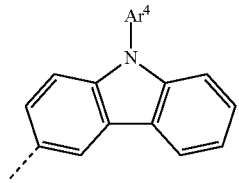

(CARB-1)

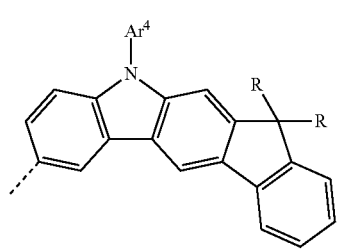

(CARB-2)

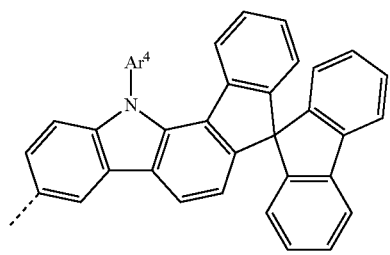

(CARB-3)

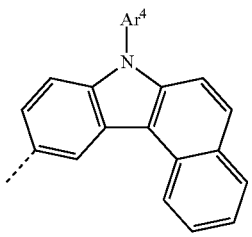

(CARB-4)

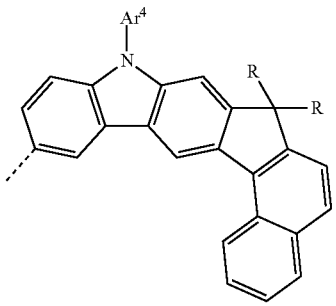

(CARB-5)

where Ar$^4$ has the meanings given in claim 1 and the groups may be substituted by one or more radicals R.

12. A formulation comprising at least one compound according to claim 1 and at least one further compound.

13. An electronic device comprising the formulation according to claim 12.

14. An electronic device comprising at least one compound according to claim 1.

15. An organic electroluminescent device which comprises the compound according to claim 1 is employed as matrix material for phosphorescent emitters in an emitting layer.

16. An organic electroluminescent device which compound according to claim 1 is employed as matrix material for a phosphorescent emitter in combination with a further matrix material.

17. An organic electroluminescent device which compound according to claim 1 is employed as matrix material for a phosphorescent emitter in combination with a further matrix material, where the further matrix material comprises pure hydrocarbon.

18. The compound according to claim 1, wherein Ar$^2$ is a phenylene or biphenyl, each of which may be substituted by one or more radicals R, and in that Ar$^3$ and Ar$^4$ represent, identically or differently on each occurrence, phenyl, biphenyl, terphenyl, quaterphenyl, fluorenyl, spirobifluorenyl, naphthyl, indolyl, benzofuranyl, benzothiophenyl, carbazolyl, dibenzofuranyl, dibenzothiophenyl, indenocarbazolyl, indolocarbazolyl, pyridinyl, pyrimidinyl, pyrazinyl, pyridazinyl, phenanthrenyl, triphenylenyl or combinations of two, three or four of these groups, each of which may be substituted by one or more radicals R.

19. A formulation comprising at least one compound according to claim 1 and at least one solvent.

* * * * *